(12) United States Patent
Kiely

(10) Patent No.: US 11,950,940 B2
(45) Date of Patent: Apr. 9, 2024

(54) SYSTEM AND METHOD FOR DETERMINING RADIATION PARAMETERS

(71) Applicant: DATA INTEGRITY ADVISORS, LLC, Washington, DC (US)

(72) Inventor: Janid Patricia Blanco Kiely, Washington, DC (US)

(73) Assignee: DATA INTEGRITY ADVISORS, LLC, Washington, DC (US)

( * ) Notice: Subject to any disclaimer, the term of this patent is extended or adjusted under 35 U.S.C. 154(b) by 468 days.

(21) Appl. No.: 17/313,372

(22) Filed: May 6, 2021

(65) Prior Publication Data

US 2021/0353244 A1  Nov. 18, 2021

Related U.S. Application Data

(63) Continuation of application No. PCT/US2019/064846, filed on Dec. 6, 2019.
(Continued)

(51) Int. Cl.
*A61B 6/02* (2006.01)
*A61B 6/00* (2006.01)
(Continued)

(52) U.S. Cl.
CPC .............. *A61B 6/025* (2013.01); *A61B 6/027* (2013.01); *A61B 6/4085* (2013.01); *A61B 6/50* (2013.01);
(Continued)

(58) Field of Classification Search
None
See application file for complete search history.

(56) References Cited

U.S. PATENT DOCUMENTS 5,400,378 A * 3/1995 Toth .............. A61B 6/488
                                                378/118
8,233,966 B2 * 7/2012 Wesse ............ A61B 6/032
                                                600/428
(Continued)

FOREIGN PATENT DOCUMENTS

CN  106999127 A *  8/2017  ............... A61B 6/04
JP  H0654916 A    3/1994
(Continued)

OTHER PUBLICATIONS

Data Integrity Advisors, LLC, International Search Report and Written Opinion, PCT/US2019/064846, dated Sep. 1, 2020, 13 pgs.
(Continued)

*Primary Examiner* — Thomas R Artman
(74) *Attorney, Agent, or Firm* — Morgan, Lewis & Bockius LLP

(57) ABSTRACT

A method includes positioning a patient at a first orientation relative to a radiation source. The method further includes using a 3D imaging technique to measure one or more positions of the patient's chest. The method further includes, while using the 3D imaging technique to measure the one or more positions of the patient's chest: generating a model of the patient's chest using the one or more positions of the patient's chest; updating the model of the patient's chest as the patient breathes; and exposing the patient to a dose of radiation using the radiation source, wherein the dose is based on the model of the patient's chest.

28 Claims, 49 Drawing Sheets

Related U.S. Application Data

(60) Provisional application No. 62/943,668, filed on Dec. 4, 2019.

(51) Int. Cl.
| | | |
|---|---|---|
| *A61B 6/40* | (2024.01) | |
| *A61B 6/50* | (2024.01) | |
| *A61N 5/10* | (2006.01) | |
| *G01S 17/894* | (2020.01) | |
| *G06T 5/00* | (2024.01) | |
| *G06T 7/11* | (2017.01) | |
| *G06T 7/187* | (2017.01) | |
| *G06T 7/33* | (2017.01) | |
| *G06T 15/06* | (2011.01) | |

(52) U.S. Cl.
CPC .......... *A61B 6/5205* (2013.01); *A61B 6/5217* (2013.01); *A61B 6/5247* (2013.01); *A61B 6/5258* (2013.01); *A61B 6/541* (2013.01); *A61B 6/544* (2013.01); *A61B 6/547* (2013.01); *A61N 5/1067* (2013.01); *A61N 5/1068* (2013.01); *G01S 17/894* (2020.01); *G06T 5/004* (2013.01); *G06T 7/11* (2017.01); *G06T 7/187* (2017.01); *G06T 7/337* (2017.01); *G06T 15/06* (2013.01); *A61N 2005/1059* (2013.01); *G06T 2207/20192* (2013.01); *G06T 2207/30064* (2013.01)

(56) References Cited

U.S. PATENT DOCUMENTS

| | | | | |
|---|---|---|---|---|
| 9,993,663 | B2 * | 6/2018 | Sabczynski | A61B 5/113 |
| 10,650,585 | B2 * | 5/2020 | Kiely | A61B 5/7292 |
| 10,970,926 | B2 * | 4/2021 | Kiely | A61B 6/584 |
| 11,120,622 | B2 * | 9/2021 | Kiely | A61N 5/1049 |
| 11,295,449 | B2 * | 4/2022 | Feain | A61B 6/032 |
| 11,660,055 | B2 * | 5/2023 | Kiely | A61B 6/50 378/20 |
| 2004/0254492 | A1 | 12/2004 | Zhang et al. | |
| 2007/0027389 | A1 * | 2/2007 | Wesse | A61B 6/032 600/407 |
| 2009/0180589 | A1 | 7/2009 | Wang et al. | |
| 2012/0253178 | A1 | 10/2012 | Mostafavi | |
| 2016/0236009 | A1 * | 8/2016 | Sabczynski | A61N 5/1037 |
| 2017/0322484 | A1 * | 11/2017 | Erhard | A61B 6/467 |
| 2019/0374189 | A1 * | 12/2019 | Kiely | A61N 5/1068 |
| 2019/0374190 | A1 * | 12/2019 | Kiely | A61N 5/1049 |
| 2019/0378329 | A1 * | 12/2019 | Kiely | A61B 6/5288 |
| 2020/0202620 | A1 * | 6/2020 | Kiely | A61B 6/032 |
| 2021/0174511 | A1 * | 6/2021 | Feain | A61N 5/1037 |
| 2021/0298695 | A1 * | 9/2021 | Kiely | A61B 6/04 |
| 2021/0353244 | A1 * | 11/2021 | Kiely | A61B 6/544 |

FOREIGN PATENT DOCUMENTS

| | | | | |
|---|---|---|---|---|
| JP | 2015-526231 A | | 9/2015 | |
| JP | 2019-130275 A | | 8/2019 | |
| WO | WO-2010083415 A1 | * | 7/2010 | .......... A61B 5/1135 |
| WO | WO2012/058615 A1 | | 5/2012 | |
| WO | WO2015/055485 A1 | | 4/2015 | |
| WO | WO2015114834 A1 | | 8/2015 | |
| WO | WO-2018087049 A1 | * | 5/2018 | |
| WO | WO-2021112867 A1 | * | 6/2021 | .......... A61B 6/0492 |

OTHER PUBLICATIONS

Data Integrity Advisors, LLC, International Preliminary Report on Patentability, PCT/US2019/064846, dated May 11, 2022, 8 pgs.

Notice of Reasons for Rejection, JP2022-529883, dated Aug. 30, 2023, 3 pgs.

Office Action of the Taiwan Intellectual Property Office-TW108144832_ dated Jun. 5, 2023, 4 pgs.

* cited by examiner

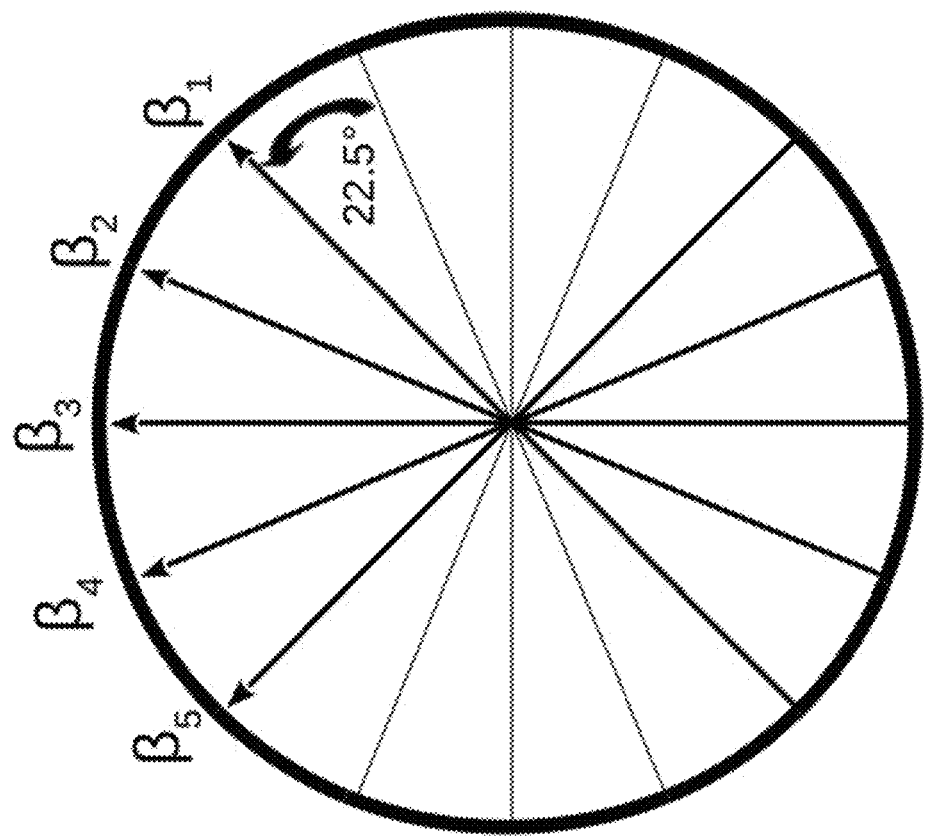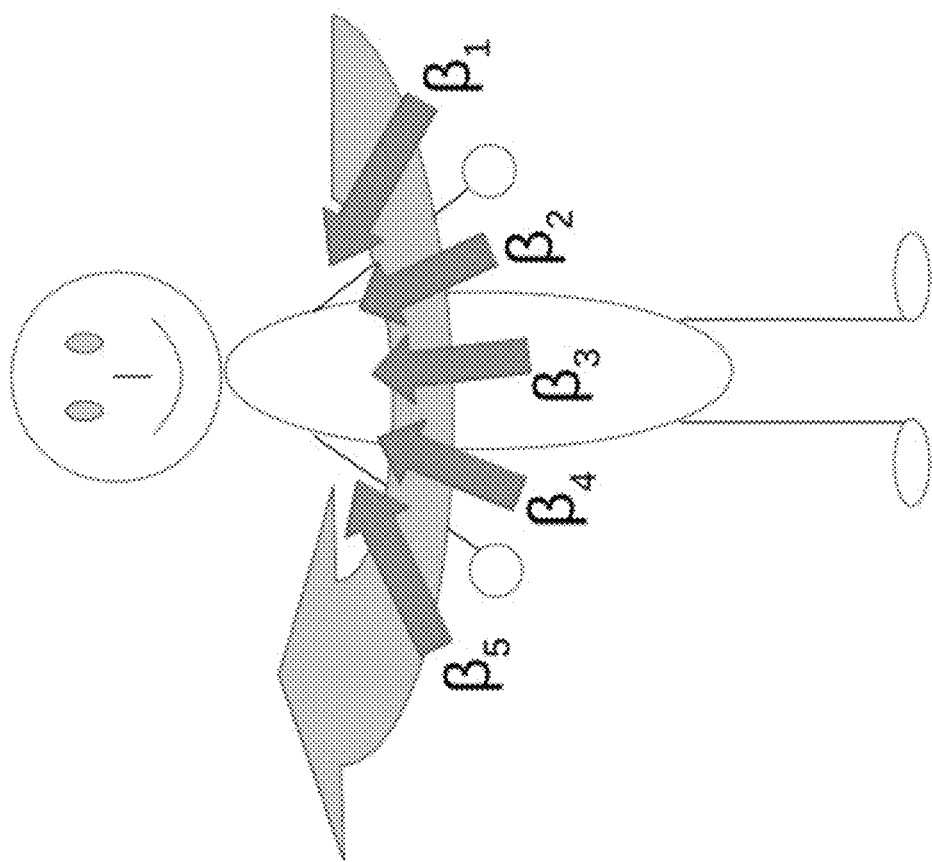
Fig. 20

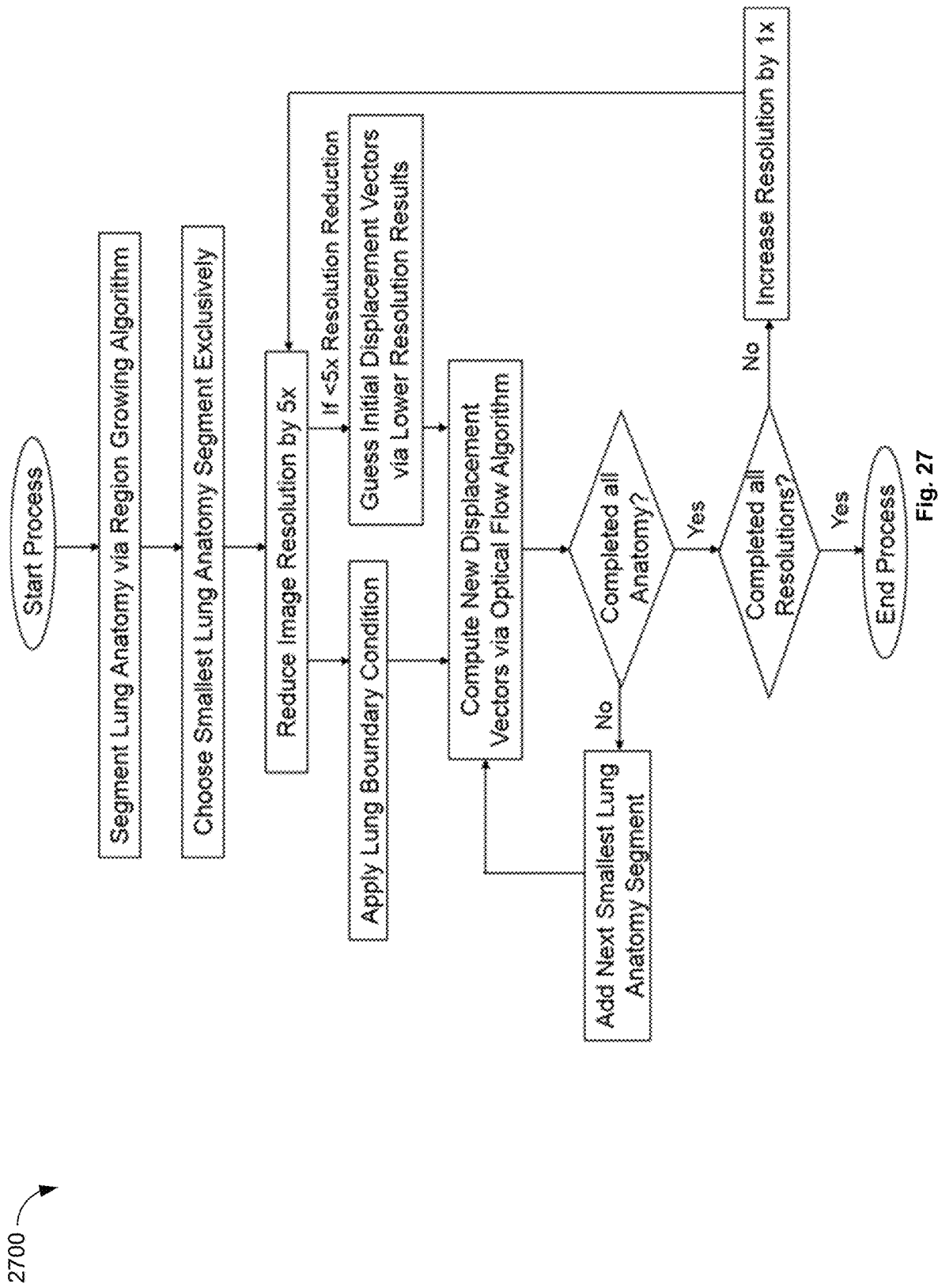

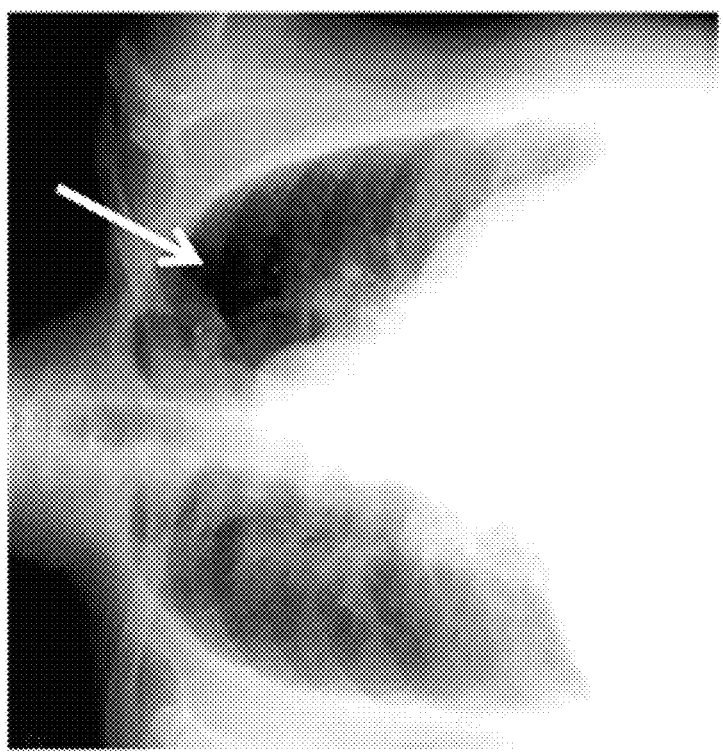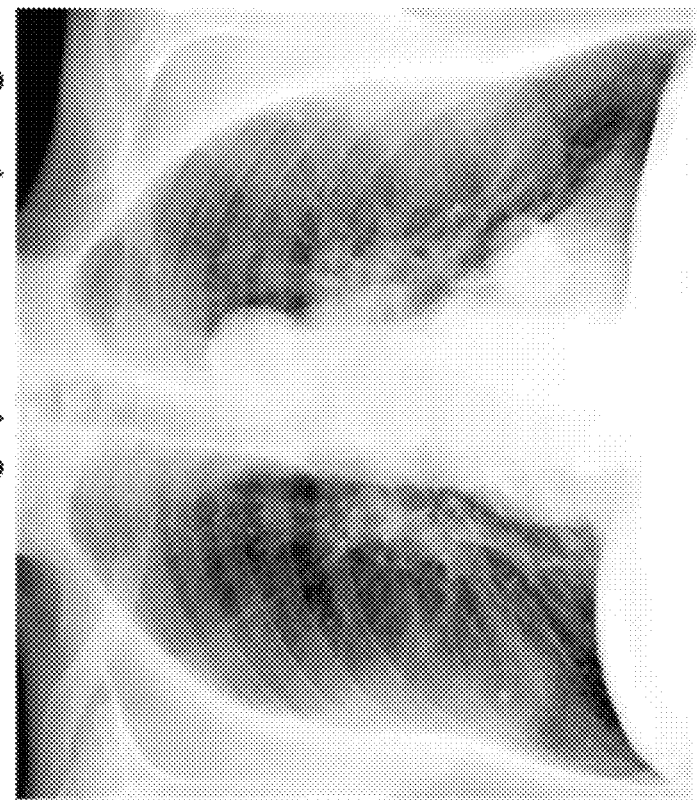
Fig. 29

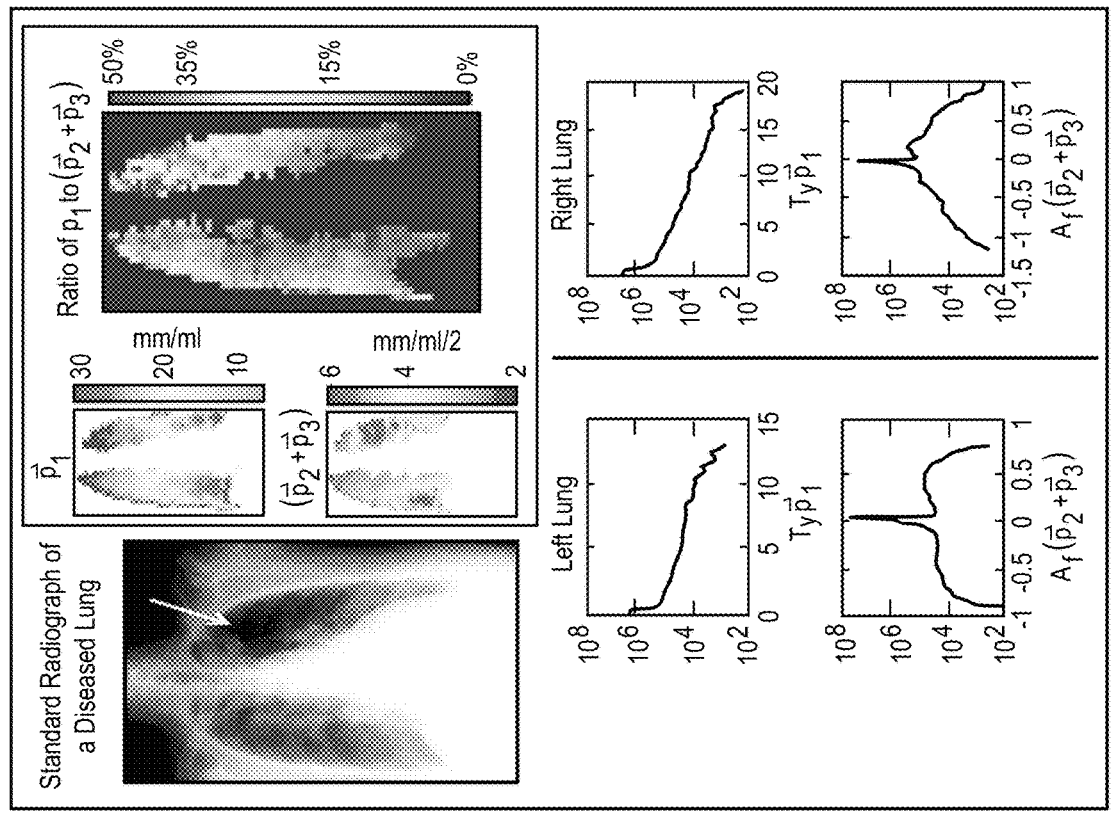
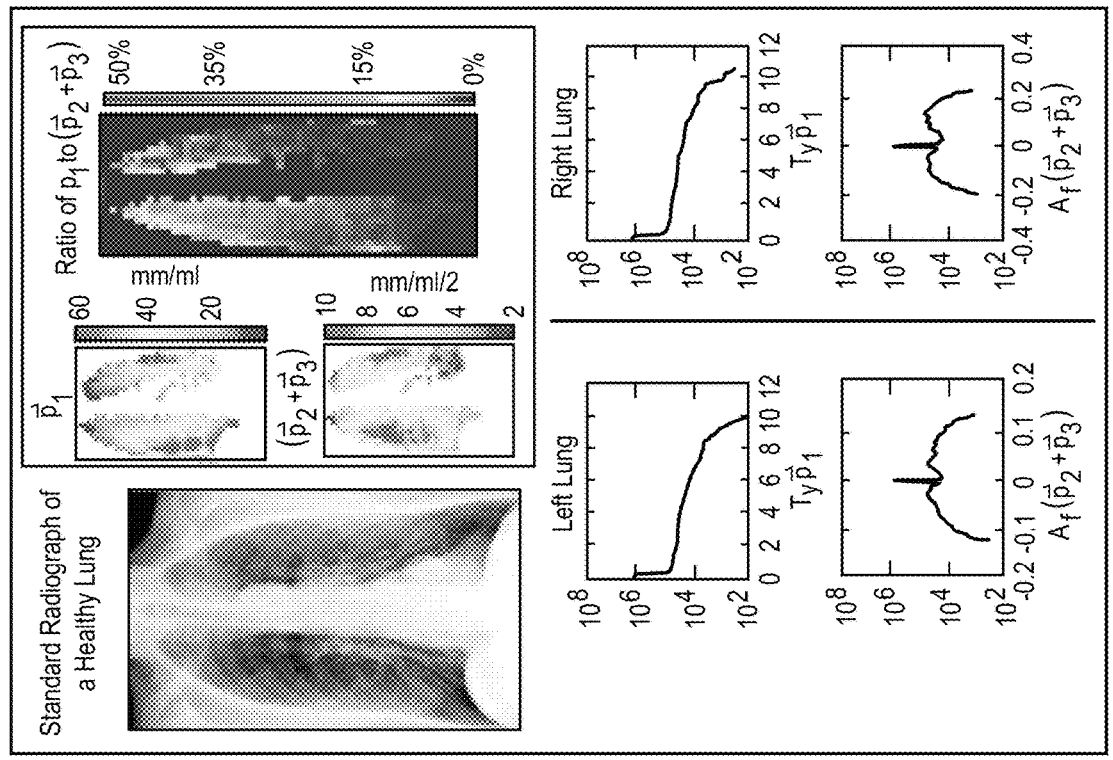
Fig. 30A
Fig. 30B

While the patient is positioned at the first orientation relative to the radiation source and while obtaining the measurement of the patient's breathing: ~ 3212

Before gating the radiation source to expose the patient to radiation: Obtain measurements of the patient's cardiac function from a plurality of cardiac cycles of the patient.
Using the measurements of the patient's cardiac function from the plurality of cardiac cycles, determine an average interval between a predefined cardiac phase and a beginning of the predefined window of the cardiac cycle. ~ 3218

The measurements from the plurality of cardiac cycles of the patient are waveform measurements of the plurality of cardiac cycles.
Validate, as statistically stable, the waveform measurements of the plurality of cardiac cycles. ~ 3220

Gate the radiation source to expose the patient to radiation based on a determination that the breathing phase of the patient matches a predefined breathing phase and a determination that the cardiac phase of the patient matches a predefined window of the cardiac cycle. ~ 3222

Gating the radiation source to expose the patient to radiation comprises gating the x-ray imaging apparatus to produce an x-ray projection of the patient's lung. ~ 3224

Gating the radiation source to expose the patient to radiation comprises gating the radiation therapy source to irradiate a region of the patient's lung at a therapeutic dose. ~ 3226

Determining that the cardiac phase of the patient matches the predefined window of the cardiac cycle includes:
In real-time, detecting the predefined cardiac phase and waiting a length of time corresponding to the average interval between the predefined cardiac phase and the beginning of the predefined window of the cardiac cycle. ~ 3228

Extract multiple displacement fields of lung tissue from multiple x-ray measurements corresponding to different breathing phases of a lung of a patient. Each displacement field represents movement of the lung tissue from a first breathing phase to a second breathing phase. Each breathing phase has a corresponding set of biometric parameters. — 3302

One or more sensors are used for measuring biometric signals of the patient as one or more sequences of time series, including one or more of a 3D spatial position localizer, a breathing phase sensor, and a cardiac phase sensor. — 3304

The 3D spatial position localizer is configured for measuring the patient's real-time body movement caused by respiration and heartbeats and outputting them as time series. — 3306

The breathing phase sensor is configured for measuring one or more physiologic metrics related to the patient's breathing, including a tidal volume and its first-order time derivative. — 3308

The cardiac phase sensor is configured for measuring periodic and stationary electrical signals generated by the patient's heart. — 3310

The biometric signals of the patient measured by the one or more sensors are used for triggering an x-ray unit to acquire an x-ray image of the patient at a specific breathing and cardiac phases. — 3312

The x-ray unit includes a clock. The biometric signals of the patient measured by the one or more sensors are synchronized with the x-ray unit's clock. Respective values of the biometric signals are recorded to be associated with the acquired x-ray image. — 3314

The biometric signals of the patient measured during a training window are used for building an optimized breathing prediction model for predicting a desired breathing phase at which an x-ray unit is triggered to capture a x-ray image of the patient. — 3316

- One or more sensors are used for measuring biometric signals of the patient as one or more sequences of time series, including one or more of a 3D spatial position localizer, a breathing phase sensor, and a cardiac phase sensor. — 3402

- Identify a cardiac phase gating window using one or more cardiac phase sensor measurements.
    Predict a breathing phase using one or more breathing phase sensor measurements.
    Identifying a coincidence between the cardiac phase gating window and the predicted breathing phase for generating an x-ray imaging pulse.
    Tag an x-ray image corresponding to the x-ray imaging pulse with the breathing phase, the cardiac phase, and 3D spatial position localizer measurements. — 3406

- The 3D spatial position localizer is configured for measuring the patient's real-time body movement caused by respiration and heartbeats and outputting them as time series. — 3408

- The breathing phase sensor is configured for measuring one or more physiologic metrics related to the patient's breathing, including a tidal volume and its first-order time derivative. — 3410

- The cardiac phase sensor is configured for measuring periodic and stationary electrical signal generated by the patient's heart, with characteristic features that correspond to the cardiac phase. — 3412

- Two distinct filters are used to remove signal drift and noise from biometric signals of the patient after being synchronized with an x-ray unit's clock. — 3414

- The biometric signals of the patient measured by the one or more sensors are used for triggering an x-ray unit to acquire an x-ray image of the patient at a specific breathing and cardiac phase. — 3416

- The x-ray unit includes a clock. The biometric signals of the patient measured by the one or more sensors are synchronized with the x-ray unit's clock and the respective values of the biometric signals are recorded to be associated with the acquired x-ray image. — 3418

FIGURE 34A

SYSTEM AND METHOD FOR DETERMINING RADIATION PARAMETERS

PRIORITY APPLICATIONS

This application is a continuation of International Application PCT/US19/64846, filed Dec. 6, 2019, which claims priority to U.S. Provisional Application 62/943,668, filed Dec. 4, 2019, each of which is hereby incorporated by reference in its entirety.

TECHNICAL FIELD

Some embodiments of the present disclosure relate to radiation imaging and therapy, and more particularly to systems and methods for determining radiation parameters (e.g., dose) from a radiation source (e.g., an x-ray imaging apparatus or a radiation therapy apparatus).

BACKGROUND

A computed tomography (CT) scan makes use of computer-processed combinations of many x-ray measurements taken from different angles to produce cross-sectional (tomographic) images (virtual "slices") of specific areas of a scanned object, allowing the medical professionals to see inside the object (e.g., a patient) without surgery. One important parameter for CT scans is the dose (e.g., the number of photons) delivered for each measurements. Typically, the dose from an x-ray tube is controlled by setting an amount of current flowing through a thermionic filament. If the dose is too low, too many photons are attenuated in the object being imaged and the image's signal-to-noise ratio will be poor. If the dose is too high, the patient is exposed to an unwarranted amount of potentially harmful radiation.

Thus, for many CT scanners, a set of reconnaissance images is taken to calibrate the dose. During the reconnaissance protocol, the CT scanner positions a rotating gantry at a vertical position (e.g., 0 degrees). The patient is instructed to hold his or her breath and the couch is moved rapidly through the bore. Next, the gantry is parked at a lateral position (e.g., 90 degrees), the patient holds his or her breath again, and the couch is moved rapidly through the bore again. During the imaging protocol, the gantry spins while the couch steps through the bore. The x-ray tube current changes (based on information obtained by the reconnaissance images) as the gantry completes a 360 degree rotation and moves to the next adjacent couch position.

SUMMARY

One major shortcoming of the reconnaissance protocol discussed above is that, since the calibration images are obtained while the patient holds his or her breath, the images acquired during the imaging protocol must also be obtained while the patient holds his or her breath. However, as discussed in further detail through this disclosure, a wealth of information can be garnered from obtaining x-ray images at different breathing phases. Thus, there is a need for systems and methods for determining radiation parameters (e.g., dose) of an x-ray imaging apparatus while the patient breathes. In some circumstances, these same principles can be applied to radiation therapy.

To that end, embodiments of the present disclosure provide a method for determining radiation parameters, performed at a radiation source (e.g., an x-ray imaging apparatus or a radiation therapy source). The method includes positioning a patient at a first orientation relative to a radiation source. The method further includes using a 3D imaging technique to measure one or more positions of the patient's chest. The method further includes, while using the 3D imaging technique to measure the one or more positions of the patient's chest, generating a model of the patient's chest using the one or more positions of the patient's chest, updating the model of the patient's chest as the patient breathes and exposing the patient to a dose of radiation using the radiation source, wherein the dose is based on the model of the patient's chest.

Further, some embodiments provide a non-transitory computer-readable storage medium storing instructions, which, when executed by a system that includes one or more processors, cause the one or more processors to perform a set of operations. The set of operations includes positioning a patient at a first orientation relative to a radiation source. The set of operations further includes using a 3D imaging technique to measure one or more positions of the patient's chest. The set of operations further includes, while using the 3D imaging technique to measure the one or more positions of the patient's chest: generating a model of the patient's chest using the one or more positions of the patient's chest; updating the model of the patient's chest as the patient breathes; and exposing the patient to a dose of radiation using the radiation source, wherein the dose is based on the model of the patient's chest.

BRIEF DESCRIPTION OF THE DRAWINGS

In order to describe embodiments of the present disclosure or technical solutions in the prior art more clearly, the drawings necessary in the descriptions of the embodiments or the prior art will be briefly explained. Obviously, the drawings in the following description are just some embodiments of the present disclosure. To those skilled in the art, in the premise of no creative labor, other drawings can also be obtained according to structures illustrated in these drawings.

FIG. 20 is an exemplary illustration of the β imaging angle position relative to the three primary imaging planes (left) and relative to the imaging isocenter of the GREX imaging system in a top-down viewing orientation (right) according to some embodiments of the present disclosure.

FIG. 27 is a schematic flow chart of a multi-resolution 3D optical flow algorithm according to some embodiments of the present disclosure.

FIG. 29 depicts an example of a healthy patient's standard radiograph and a standard radiograph for a sick patient with a stage 1b left upper lung tumor (indicated with the arrow).

FIGS. 30A-30B depict examples of GREX parameter maps showing indicators of the healthy patient's situation GREX parameter maps showing indicators of the sick patient's health situation according to some embodiments of the present disclosure.

FIGS. 32A-32B are flow diagrams for a method of gating a radiation source according to some embodiments of the present disclosure.

FIGS. 33A-33C are flow diagrams for a method of determining a biophysical model for a lung of a patient according to some embodiments of the present disclosure.

FIGS. 34A-34C are flow diagrams for a method of generating a 3D x-ray image cube movie according to some embodiments of the present disclosure.

DETAILED DESCRIPTION

Figure 1:
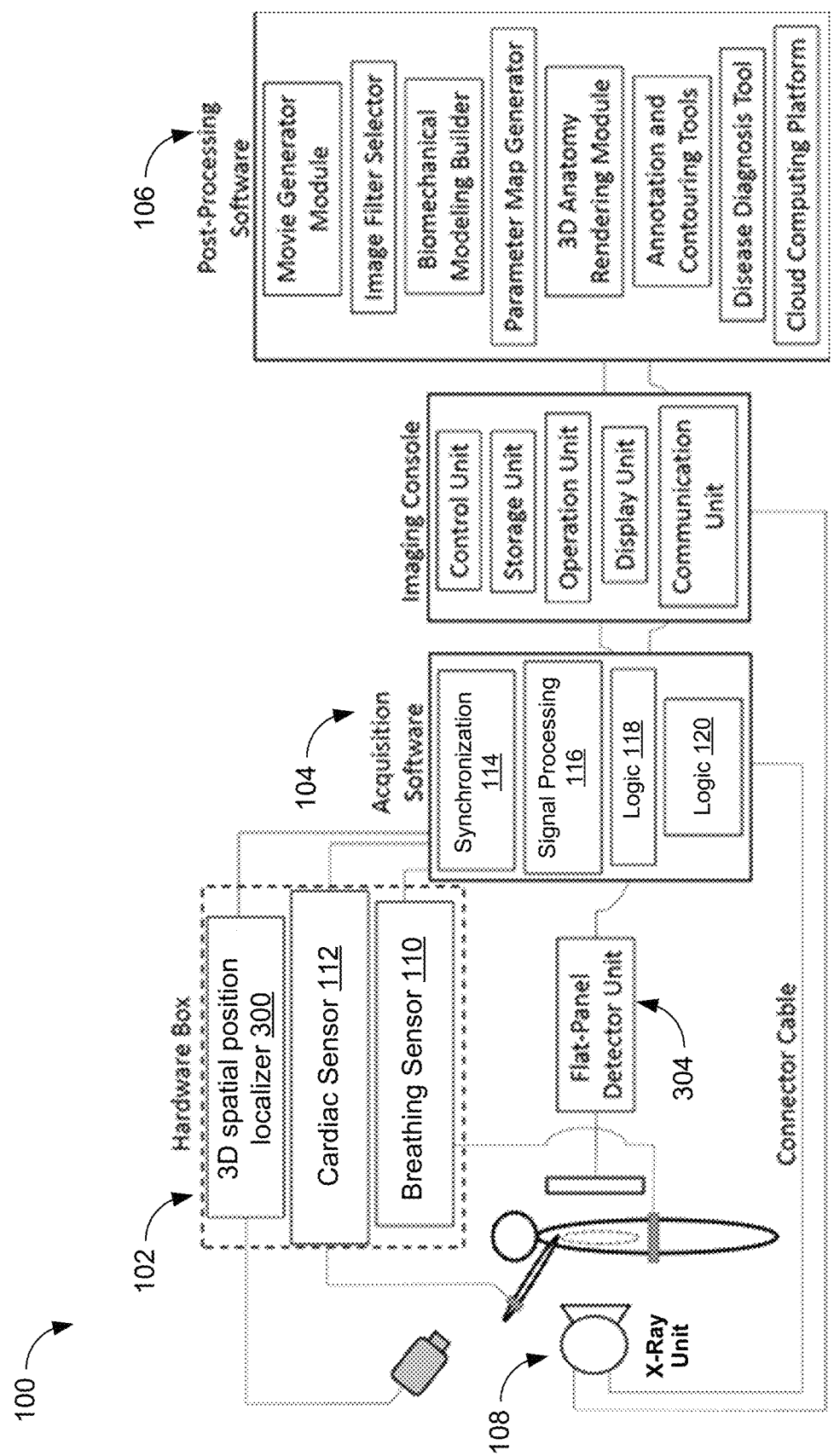
FIG. 1 is a schematic block diagram of the GREX imaging system including a hardware box, acquisition software, and post-processing software according to some embodiments of the present disclosure.

Reference will be made in detail to embodiments of the present disclosure. The same or similar elements and the elements having same or similar functions are denoted by like reference numerals throughout the descriptions. The embodiments described herein with reference to drawings are explanatory, illustrative, and used to generally understand the present disclosure. The embodiments shall not be construed to limit the present disclosure.

In the specification, unless specified or limited otherwise, relative terms such as "central", "longitudinal", "lateral", "front", "rear", "right", "left", "inner", "outer", "lower", "upper", "horizontal", "vertical", "above", "below", "up", "top", "bottom" as well as derivative thereof (e.g., "horizontally", "downwardly", "upwardly", etc.) should be construed to refer to the orientation as then described or as shown in the drawings under discussion. These relative terms are for convenience of description and do not require that the present disclosure be constructed or operated in a particular orientation.

In the present invention, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

In the present invention, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed therebetween. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

FIG. 1 is a schematic block diagram of the GREX imaging system 100 including a hardware box 102, acquisition software 104 (e.g., stored in non-transitory memory), and post-processing software 106 (e.g., stored in non-transitory memory) according to some embodiments of the present disclosure.

There are three measurement sensors in the hardware box 102 (e.g., 3D spatial position localizer 300, breathing phase sensor 110, and heart phase sensor 112) that independently collect biometric signals of a patient as time series, and the collected time series serve as the inputs into the acquisition software 104. The acquisition software 104 processes and filters the biometric time series measurements to generate an imaging trigger signal (e.g., that gets x-ray unit 108). The imaging trigger signal targets a specific breathing phase and, optionally, a cardiac phase of the patient. The breathing phase and cardiac phase are each defined by their respective biometric time series measurements. A connector cable transmits the imaging trigger signal from the acquisition software 104 to the x-ray unit 108, which acquires breathing and cardiac phase radiographic images at the targeted phases. Once acquired, a series of breathing and cardiac phase targeted images, which define a complete breathing cycle, are input into the post-processing software 106. The post-processing software builds a biomechanical model of lung motion from the breathing and cardiac phase targeted images. The biomechanical model is then used to generate other diagnosis results in the post-processing software. Although this application uses x-ray image as an example, it would be apparent to those skilled in the art that the approaches disclosed in this application can be adapted to be applied to other types of medical images with little (if any) effort. For example, the process of building the biomechanical model is not limited to the use of x-ray images and can use other types of medical images (e.g., CT-Scan, MRI, etc.).

Figure 2:
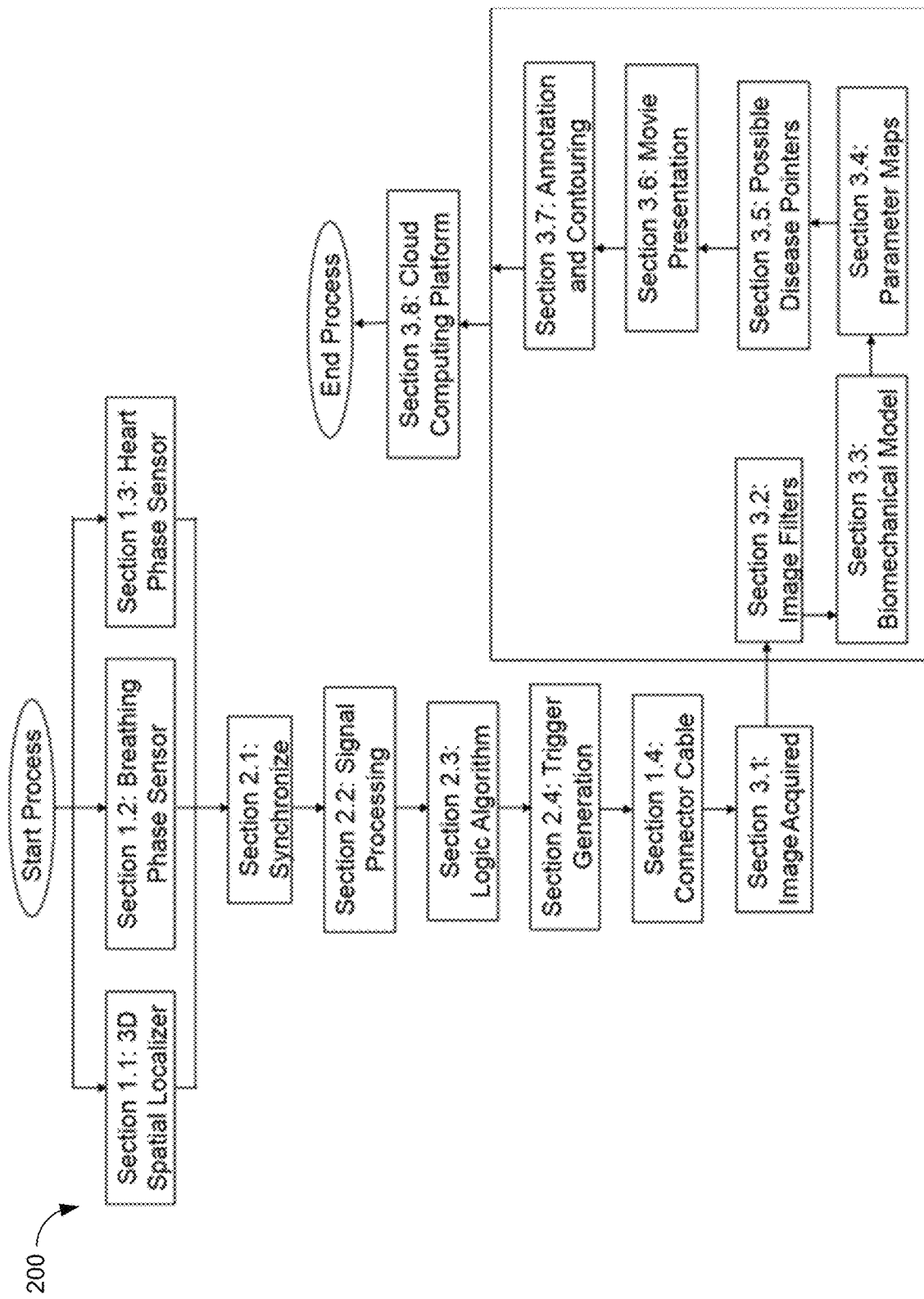
FIG. 2 is a schematic flow chart of the GREX image acquisition process according to some embodiments of the present disclosure.

FIG. 2 is a schematic flow chart of the GREX image acquisition process 200 according to some embodiments of the present disclosure (e.g., performed by acquisition software 104, FIG. 1). Specifically, the acquisition software 104 synchronizes and processes the time series measurements from the hardware box 102 in order to remove potential signal drift and noise. The acquisition software 104 then implements a phase prediction algorithm that predicts the breathing and cardiac phase from the synchronized, drift-free and noise-free time series inputs. Based on the breathing and cardiac phase prediction results, the acquisition software 104 uses a logic algorithm 118 to search for targeted breathing and cardiac phase coincidences. The targeted breathing and cardiac phase coincidences define the conditions that prompt the image trigger generation and the resulting image acquisitions by the x-ray unit 108. Once the GREX images are acquired, the post-processing software performs new lung disease diagnosis using the GREX images that was previously unavailable to healthcare professionals. For example, the acquired GREX images are used to build a biomechanical model that defines the chest geometry as a function of the breathing and cardiac phase without explicitly including a time parameter.

In this document, a GREX-based imaging system is divided into three sections. Section 1 describes embodiments of the hardware box 102. Section 2 describes embodiments of the acquisition software 104. Section 3 describes embodiments of the post-processing software 106. Each section describes, in greater detail, the components and functions that constitute the hardware box 102, the acquisition software 104, and the post-processing software 106 as shown in FIG. 1.

Section 1. Hardware Box 102

In some embodiments, the hardware box 102 has at least two responsibilities. The first is to collect biometric signals that define the chest's anatomic geometry. The second is to communicate with the digital diagnostic x-ray unit (e.g., x-ray unit 108).

The biometric signal inputs that define the chest's anatomic geometry include: the chest dimensions (measured via the 3D Spatial Localizer 300, FIG. 3), the breathing phase (measured via the breathing phase sensor 110), and the cardiac phase (measured via the ECG monitor). Within the hardware box 102, the biometric signals are sampled in real-time, at 100 Hz, in order to create time series curves for each signal input. The outputs of the hardware box 102, namely the time series curves, are then passed to the acquisition software.

Figure 3:
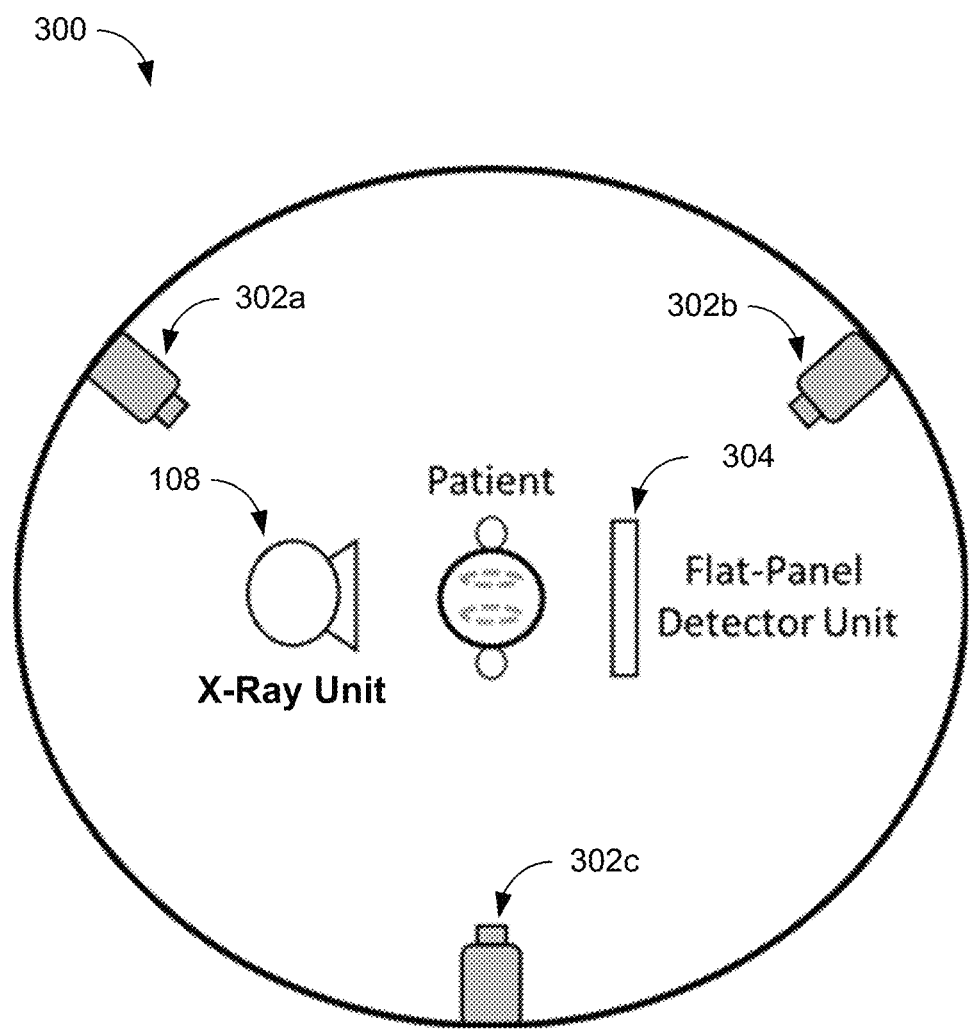
FIG. 3 is a schematic block diagram depicting a top-down view of a 3D spatial position localizer of the GREX imaging system according to some embodiments of the present disclosure.

FIG. 3 is a schematic block diagram depicting a top-down view of a 3D spatial position localizer 300 of the GREX imaging system 100 according to some embodiments of the present disclosure.

Section 1.1—3D Spatial Position Localizer 300

The 3D spatial position localizer 300 measures the patient's real-time body movement caused by respiration and heartbeats and outputs them as a time series in a coordinate space (e.g., Cartesian, polar, hyper, etc.). As shown in FIG. 3, the 3D spatial position localizer 300 includes three separate 3D detectors (e.g., detectors 302a through 302c) that are fixed to a balanced circular tract on the room's ceiling. There are 120° angular increments separating the system's three 3D detectors 302a from one another. The patient is located between the x-ray unit 108 and the x-ray detector panel 304, such that the patient is located at the center of the ceiling-mounted 3D spatial position localizer 300. The system measures the patient's chest expansion (e.g., rise and fall) in a predefined coordinate space. Each 3D detector 302 has an unobstructed view of the patient's torso and one of the x-ray unit 108 and the detector panel 304. Note that, in some embodiments, there may be more than three 3D detectors 302 are employed, whereas, in some embodiments fewer than three 3D detectors 302 are employed. In some embodiments, the detectors are cameras (e.g., the 3D imaging technique uses photogrammetry and/or structured light). In some embodiments, the detectors are LIDAR detectors (e.g., the 3D imaging technique uses time of flight).

Using real-time depth maps, each 3D detector 302 creates a surface rendering of the patient. Simultaneous information from all three 3D detector 302 is combined to form a volumetric skin surface position measurement (e.g., using a ray-casting technique) that changes, in real-time, based on the patient's breathing and cardiac phase. The 3D spatial position localizer 300 uses the volumetric skin surface position measurements in at least two ways: (i) defining the spatial boundary of the patient and (ii) determining the tissue location of the patient. Based on the assumptions such as skin thickness, rib thickness, muscular thickness, and skeletal position, which are derived from the canonical Medical Internal Radiation Dose (MIRD) Anatomic Database, the 3D spatial position localizer 300 approximates the lung's real-time, spatial position inside the patient. The 3D spatial position localizer 300 uses the MIRD data to calculate the lung's spatial boundary conditions, which are then made available to the post-processing software 106. For example, the 3D spatial position localizer 300's estimation of the lung's spatial boundary condition creates an initial chest geometry that the post-processing software 106 uses to simulate the cumulative tissue density along a ray that originates at the x-ray unit 108.

Section 1.2—Breathing Phase Sensor 110

The breathing phase sensor 110 in the hardware box 102 measures key physiologic metrics related to breathing, namely the tidal volume and its first-order time derivative (e.g., the rate of tidal volume changes over time or airflow). There are two methods to measure tidal volume: direct tidal volume measurement and indirect tidal volume measurement. Direct tidal volume measurement is performed with a mouth spirometer, which is comprised of a turbine within a tube that spins at a rate proportional to the volume of air that the patient inhales or exhales. Indirect tidal volume measurement is performed with an abdominal belt (or any other geometric measurement of the patient's chest, as described herein) that measures the patient's abdominal circumference changes during breathing (as shown in FIG. 1). Greater abdominal circumference means inhalation, and less abdominal circumference means exhalation. An abdominal belt does not directly measure the tidal volume. To convert changes in abdominal circumference into a physiologically meaningful quantity, the hardware box 102 associates the abdominal circumference changes with the estimated lung volume determined via the 3D spatial position localizer 300. For example, chest expansion is proportional to abdominal expansion during respiration. When used together, measurements by the abdominal belt and 3D spatial position localizer 300 can be used to estimate the lung's air content.

The term tidal volume, as used herein, means a difference between a current lung volume and a predefined baseline (e.g., a volume during maximum exhalation of a normal breath without extra effort applied, a volume during maximum inhalation of a normal breath without extra effort applied, or any other suitable fiducial volume). Based on the ideal gas law, differences in air density between room air and internal air lead to air in the lung expanding 11% more than the tidal volume. To conserve mass, the body expands 11% more volumetrically than the volume of air inhaled. Therefore, the lung's tidal volume can thus be calculated by using an external measurement of the body that is calibrated to internal air content. Moreover, the 3D spatial position localizer 300 provides a secondary check of both the air content and the accuracy of the tidal volume measurement by identifying the patient's volumetric expansion during breathing. The volumetric expansion of the body is compared with estimates for the volume of air in the trachea, lungs, and bronchi from the x-ray images.

Section 1.3—Heart Phase Sensor 112

As shown in FIG. 1, cardiac phase is measured (e.g., by heart phase sensor 112) with either an electrocardiographic (ECG) monitor or a blood volume pressure device. For example, using the ECG monitor, a clinician places leads on each of the patient's arms and places a ground lead on the patient's lower left side of the abdomen (away from the diaphragm and the abdominal belt). The human heart generates a periodic and stationary electrical signal, with characteristic features that correspond to the heartbeat phase. A stationary signal is one that is a stochastic process whose joint probability distribution does not change in time. The blood volume pressure device uses a light source and a photo sensor to measure light attenuation in a patient's finger. Circulating blood volume, which is driven by the heartbeat, results in varying light attenuation magnitudes in the patient's finger. The light attenuation magnitude is directly proportional to the cardiac phase.

Typically, the digital diagnostic x-ray unit (e.g., x-ray unit 108) is turned on with an analog plunger that attaches to a plug port. The plug port is uniquely configured to accept a plunger with a specific pin configuration. In every pin configuration, there is an "acquisition pin," which accepts the voltage signal that turns on (e.g., gates) the x-ray unit. When an end-user depresses a plunger, the plunger sends a voltage pulse to the digital diagnostic x-ray unit, which activates the imaging beam through the patient's body.

As shown in FIG. 1, the hardware box 102 uses a connector cable to communicate the same voltage pulse (e.g., gating signal) from the acquisition software to the digital diagnostic x-ray unit 108. The voltage pulse signal turns the digital diagnostic x-ray beam on (e.g., gates the x-ray beam) when the voltage pulse signal surpasses a predefined voltage threshold, and it turns the x-ray unit 108 off when the voltage pulse signal on the pin becomes less than the predefined voltage threshold. In some embodiments, the hardware box 102 creates a square wave signal with a pulse height greater than the predefined voltage threshold and maintains the pulse height for the duration of the image exposure. This is to say that a square pulse with Y voltage that lasts for X seconds is generated for the x-ray unit 108 to take an x-ray image of the patient. Sub-threshold voltages less than Y do not trigger the scanner, such that the value of Y must be greater than the predefined voltage threshold to initiate the x-ray image. Pulse duration X is the amount of the image's exposure time, beginning the moment that voltage Y exceeds the predefined voltage threshold and ending when the voltage drops below the predefined voltage threshold. The voltage's dropping below the predefined voltage threshold turns the x-ray unit 108 off. The pulse duration is defined by the manufacturer's specifications but is generally in the order of a few milliseconds.

Section 2. Acquisition Software 104

The acquisition software 104 is designed to collect the hardware box 102's measured spatial, heart and lung time series and determine when to trigger the x-ray unit 108 to acquire an x-ray image at a specific breathing and cardiac phase. The acquisition software 104 then accurately overlays (e.g., synchronizes) the measured heart and lung phases, processes (e.g., filters) the collected biometric time series, identifies appropriate imaging times, and creates an electronic trigger signal for the digital diagnostic x-ray unit 108. The electronic trigger signal (e.g., gate signal) turns the x-ray unit 108 on, acquiring a snapshot image of the chest geometry. The spatial, heart, and lung values that are associated with the snapshot are recorded to define the chest's surface geometry when the image was taken. The entire process is automated and is user-input-independent. As shown in FIGS. 1 and 2, the process implemented by the acquisition software 104 includes four subsidiary components: Section 2.1 (Synchronization Module 114), Section 2.2 (Signal Processing Module 116), Section 2.3 (Logic Algorithm 118), and Section 2.4 (Trigger Generation Module 120).

Section 2.1—Synchronization Module 114

Inputs to the synchronization module 114, including 3D spatial position localizer 300's signal, breathing phase sensor 110's signal, and heart phase sensor 112's signal are synchronized with the x-ray unit 108's clock by the synchronization module 114. Note that the physiological biometric signals are asynchronously collected, and therefore require synchronization. One source of asynchronicity is that the breathing cycle is slower than, and completely independent from, the cardiac cycle. As explained previously, the breathing cycle and the cardiac cycle are measured separately with different sensors. The synchronization module 114 is configured to synchronize the breathing and heart phase sensors with the acquired images. When an image is taken, the image displays the chest's anatomic geometry at a moment in time. That moment in time is recorded using the x-ray unit 108's native timing system, which is not necessarily synchronized with the breathing and heart sensor biometric time series.

Figure 4:
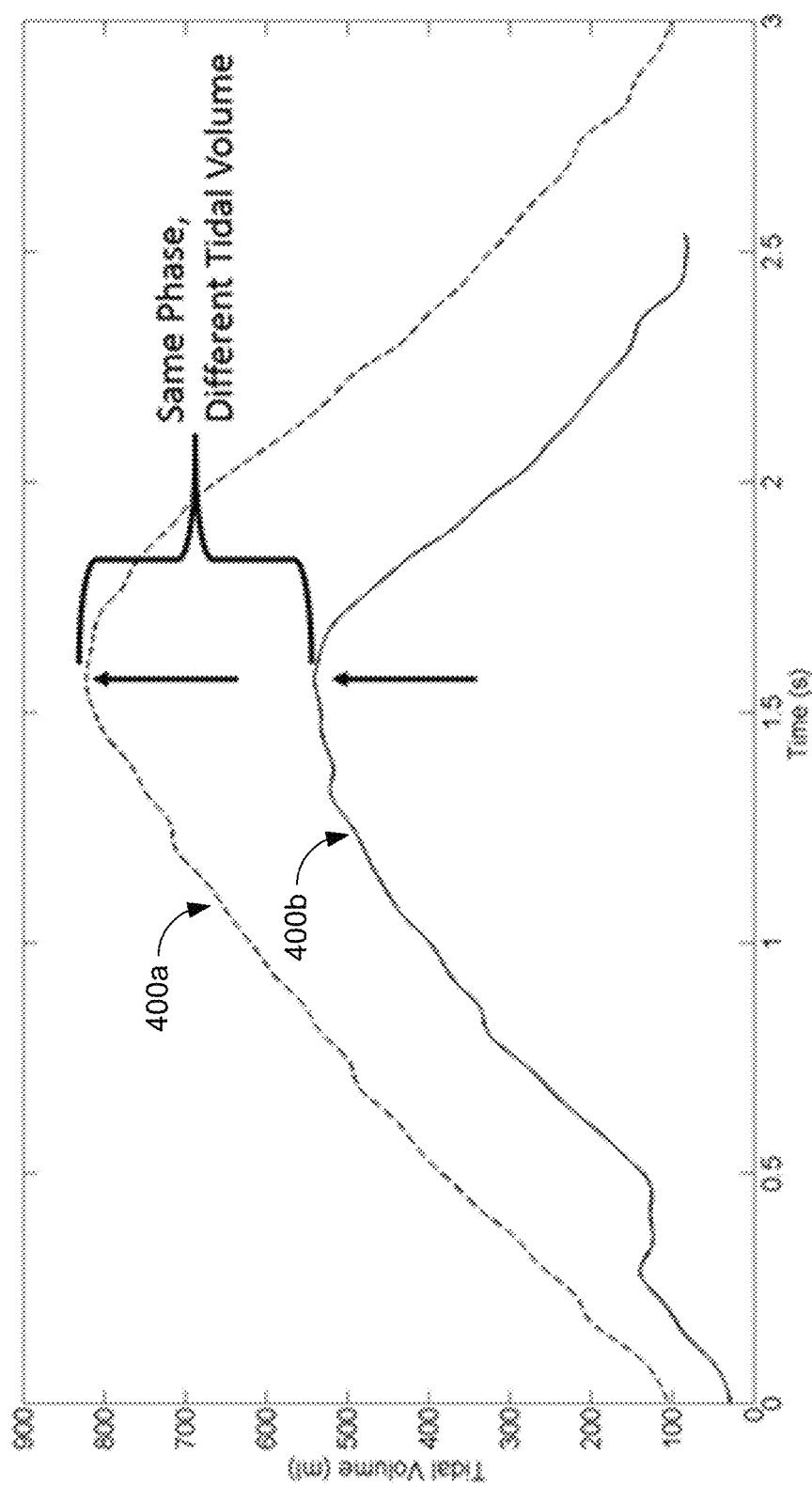
FIG. 4 depicts examples of two breaths sharing the same maximum inhalation phase in time but with radically different tidal volumes according to some embodiments of the present disclosure.

It should be noted that time alone does not differentiate between time periods of irregular breathing versus time periods of regular breathing. In other words, if time is the sole defining dimension of breathing phase, an image taken during a normal breath and an image taken during an abnormal breath (like a cough) are computationally indistinguishable from one another. FIG. 4 depicts examples of two breaths 400 (e.g., 400a and 400b) from the same individual sharing the same maximum inhalation phase in time but with radically different tidal volumes according to some embodiments of the present disclosure. When superimposed on one another, despite having a similar maximum inhalation phase, the two breaths 400 are in fact dissimilar because they have different tidal volume magnitudes. In some embodiments, tidal volume refers to a value of a volume (e.g., in ml) measured relative to a baseline volume. For example, the baseline volume represents the minimum volume of the lung (e.g., at maximum exhalation) during a normal breath of the patient (e.g., without extra effort or force to exhale). In some embodiments, the baseline volume changes for each patient. In some embodiments, the baseline volume is represented as 0. In some embodiments, the tidal volume is measured at a point in time. A representation of changes in the tidal volume over a period of time is shown in FIG. 4.

To overcome the issue with the time dimension, the GREX imaging system 100 defines the breathing phase by the physiologic values that are acquired from the various physiologic sensors in the hardware box 102, which are more informative breathing phase dimensions compared to time. The synchronization module 114 serves primarily to allow a seamless transition between the x-ray unit 108 and the GREX imaging system 100. In some embodiments, the acquisition software 104 uses a 30-second long training window, discussed in detail below within Section 2.2, during which the collected tidal volume time series observations are used to calculate tidal volume percentiles. The acquisition software 104 uses the tidal volume percentiles to define the breathing phase rather than the peak-to-peak time interval of a periodic cosine wave. The acquisition software 104's tidal volume percentiles are a more informative method of defining the lung geometry compared to the peak-to-peak periodic cosine curves because of breath-to-breath tidal volume variations.

Figure 5:
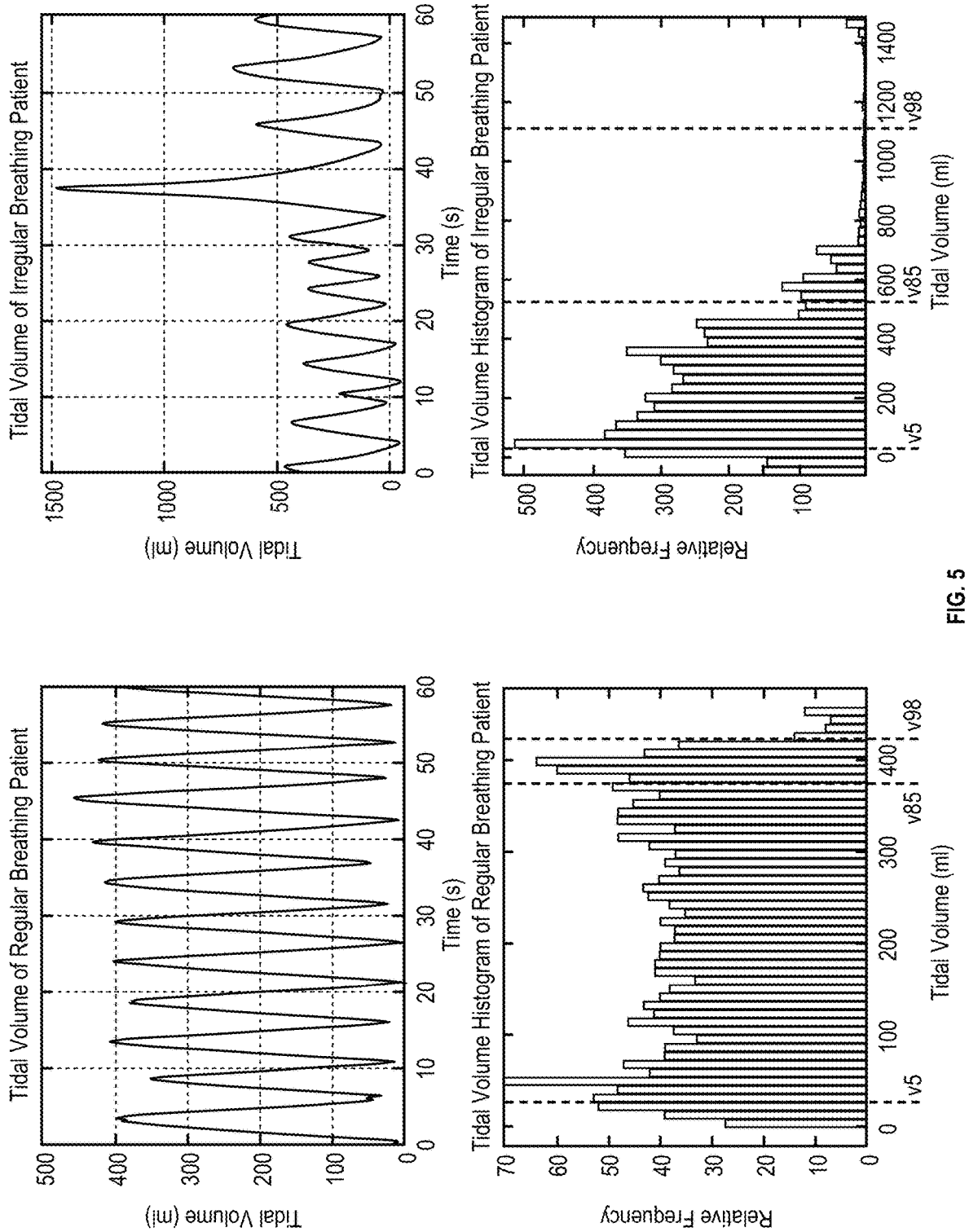
FIG. 5 depicts examples of tidal volume percentiles (two bottom subplots) for a regular breathing patient (upper left subplot) and for an irregular breathing patient (upper right subplot), respectively, according to some embodiments of the present disclosure.

FIG. 5 depicts examples of tidal volume percentiles (two bottom subplots) for a regular breathing patient (upper left subplot) and for an irregular breathing patient (upper right subplot), respectively, according to some embodiments of the present disclosure. To quantitatively assess the tidal volume histograms for irregular breathing, a ratio between normal inhalation tidal volumes and extreme inhalation tidal volumes is used as a metric of the breathing phase. The ratio has thresholds that define the probability of the patient having breathed irregularly. As shown in the two bottom subplots of FIG. 5, vertical lines show where the 85th, 90th, 95th, and 98th percentile tidal volumes are located in the tidal volume histograms. In the regular breathing case (lower left-side subplot of FIG. 5), the more normal tidal volume percentile values (85th and 90th) are located closer to the extreme tidal volume percentile values (95th and 98th) than in the irregular breathing case (lower right-side subplot of FIG. 5).

Figure 6:
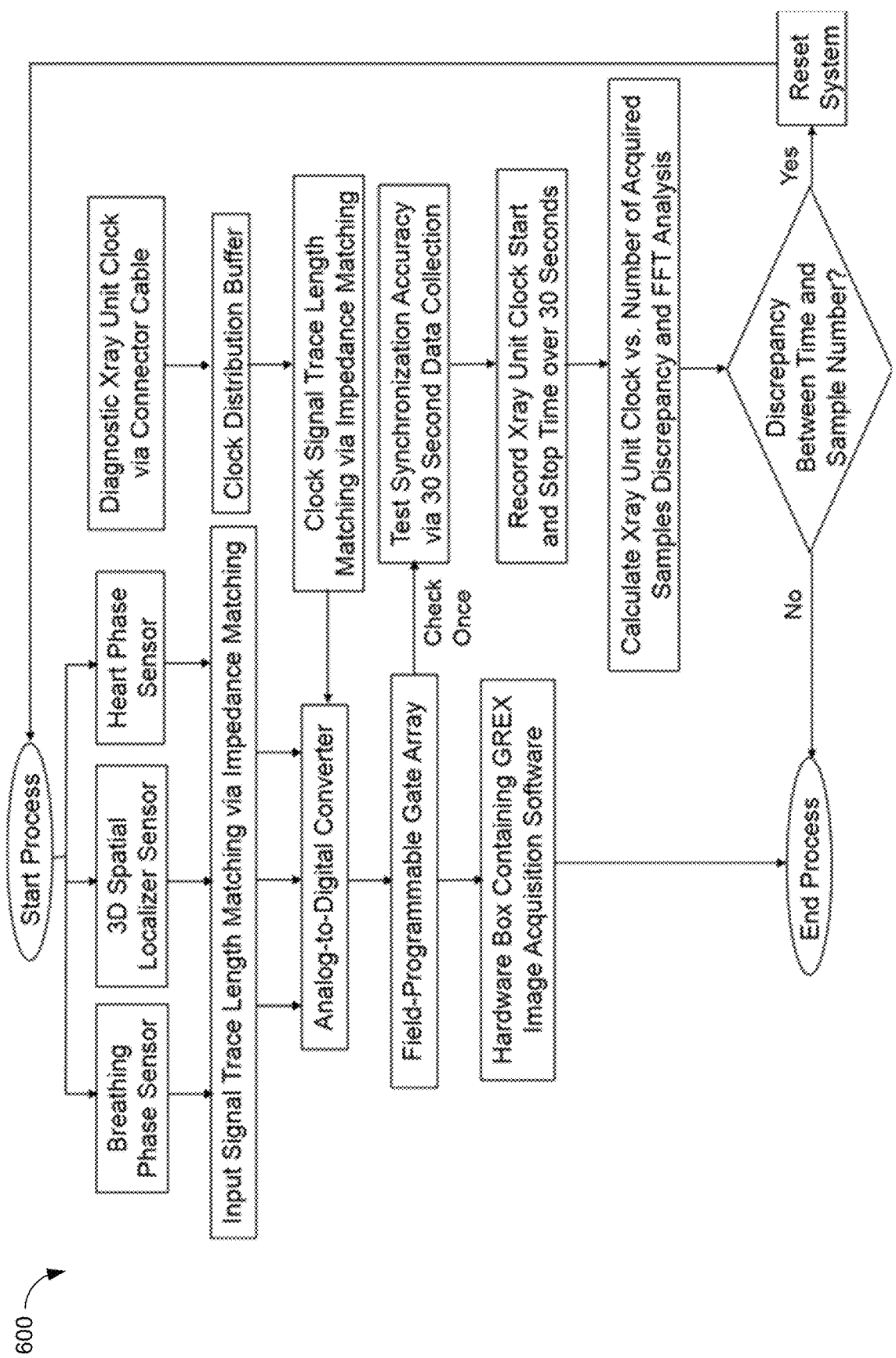
FIG. 6 is a schematic flow chart of a synchronization process according to some embodiments of the present disclosure.
Figure 7:
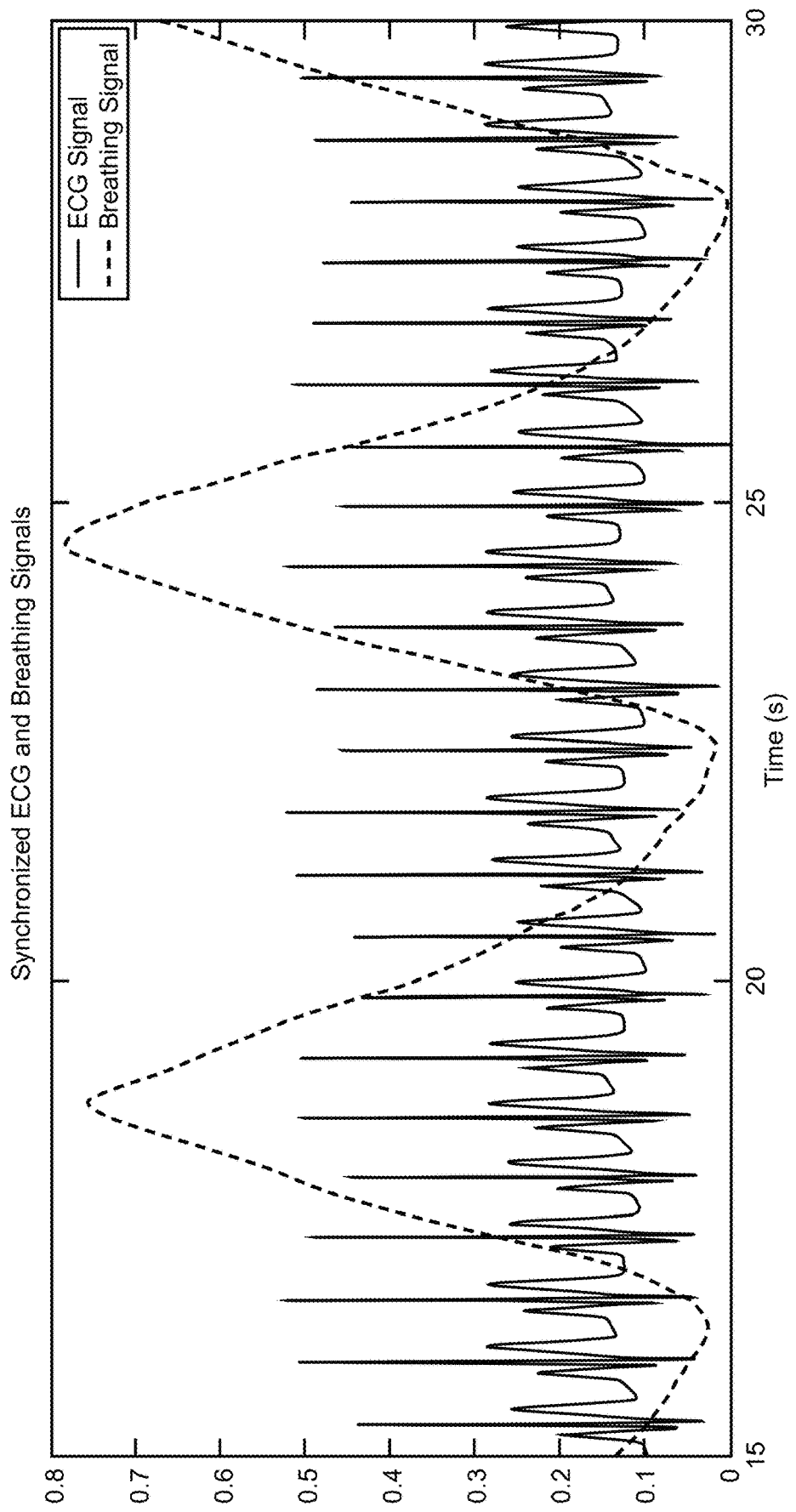
FIG. 7 depicts a synchronized heart electrocardiogram (ECG) signal and a lung breathing signal according to some embodiments of the present disclosure.

FIG. 6 is a schematic flow chart of a synchronization process 600 between different sensors in the hardware box 102 and the diagnostic x-ray unit 108 according to some embodiments of the present disclosure. Note that the hardware box 102 continuously collects the tidal volume percentile-defined breathing phases, the ECG-defined cardiac phases, and the 3D spatial position localizer 300 defined coordinates of the chest geometry. The sensor signals supporting these measurements need to be synchronized with one other before being synchronized with the x-ray unit 108. To do so, measurement channel differences and cable electrical resistivity differences between different sensors are also corrected by matching trace lengths using impedance matching in a digital-to-analog converter. Because the x-ray unit 108's clock (e.g., timing system) is usually not synchronized with the hardware box 102's clock, the connector cable is configured to connect to the data acquisition board and interface it with the x-ray unit 108's clock. The x-ray unit 108's clock passes through a distribution buffer and is trace-matched for each channel in the analog-to-digital converter. The converted digital signals are passed into a field-programmable gate array where the synchronization across all signals is ensured. When the acquisition software 104 properly synchronizes the breathing and heart phase sensor signals, the result should be similar to the example shown in FIG. 7.

To avoid the unwanted radiation exposure for the patient, the acquisition software 104 does not send any triggering signals to activate the x-ray unit 108 via the connector cable without appropriate synchronization between different components of the GREX imaging system 100. In some embodiments, the 30-second training window is used for verifying the synchronization between the hardware box 102's clock and the x-ray unit 108's clock. Therefore, the 30-second training window should contain 30 seconds worth of samples. If every sensor in the hardware box 102 as well as the x-ray unit 108's clock do not show exactly 30 seconds worth of samples, then synchronicity has failed to occur. To that end, if this aforementioned checking procedure contains a discrepancy, the synchronization system will restart to correct the discrepancy. It should be noted that the 30-second training window is for illustrative purpose and one skilled in the art would understand that the length of the training window varies as long as there is sufficient data for performing the synchronization process.

Section 2.2—Signal Processing Module 116

After the spatial position, breathing phase, and cardiac phase signals are synchronized, the acquisition software 104 processes the sensor signals to remove noise and ultimately predicts accurate tidal volume of the patient. Noise in the measured lung and heart time series comes from the sensor electronics, the electrodes, as well as from background electrical signals. A suite of filters that specifically maintains temporal accuracy removes the noise from the measured lung and heart time series such that the biometric time series maintain temporal accuracy after being filtered by the suite of filters.

Figure 8:
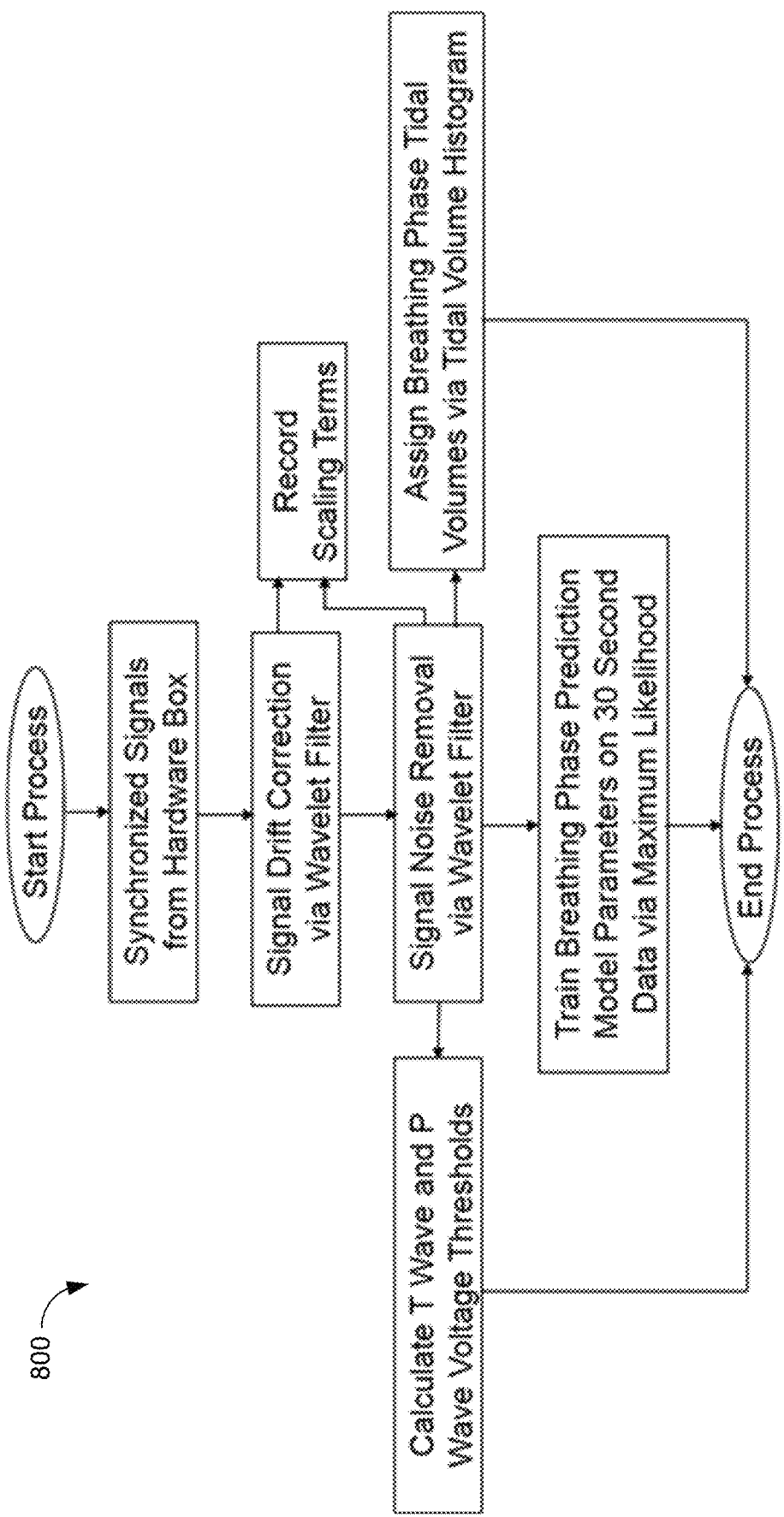
FIG. 8 is a schematic flow chart of a drift and signal noise removal process according to some embodiments of the present disclosure.

In some embodiments, two distinct filters (e.g., wavelet filters) are used to remove signal drift and noise from the biometric time series. Signal drift skews measurements taken over time so that measurements at the beginning of the data collection are not consistent with measurements taken at the end of the data collection. Signal noise is not physiologic in nature and causes serious problems when calculating the patient's airflow from tidal volume measurements. FIG. 8 is a schematic flow chart of a drift and signal noise removal process 800 according to some embodiments of the present disclosure.

Figure 9:
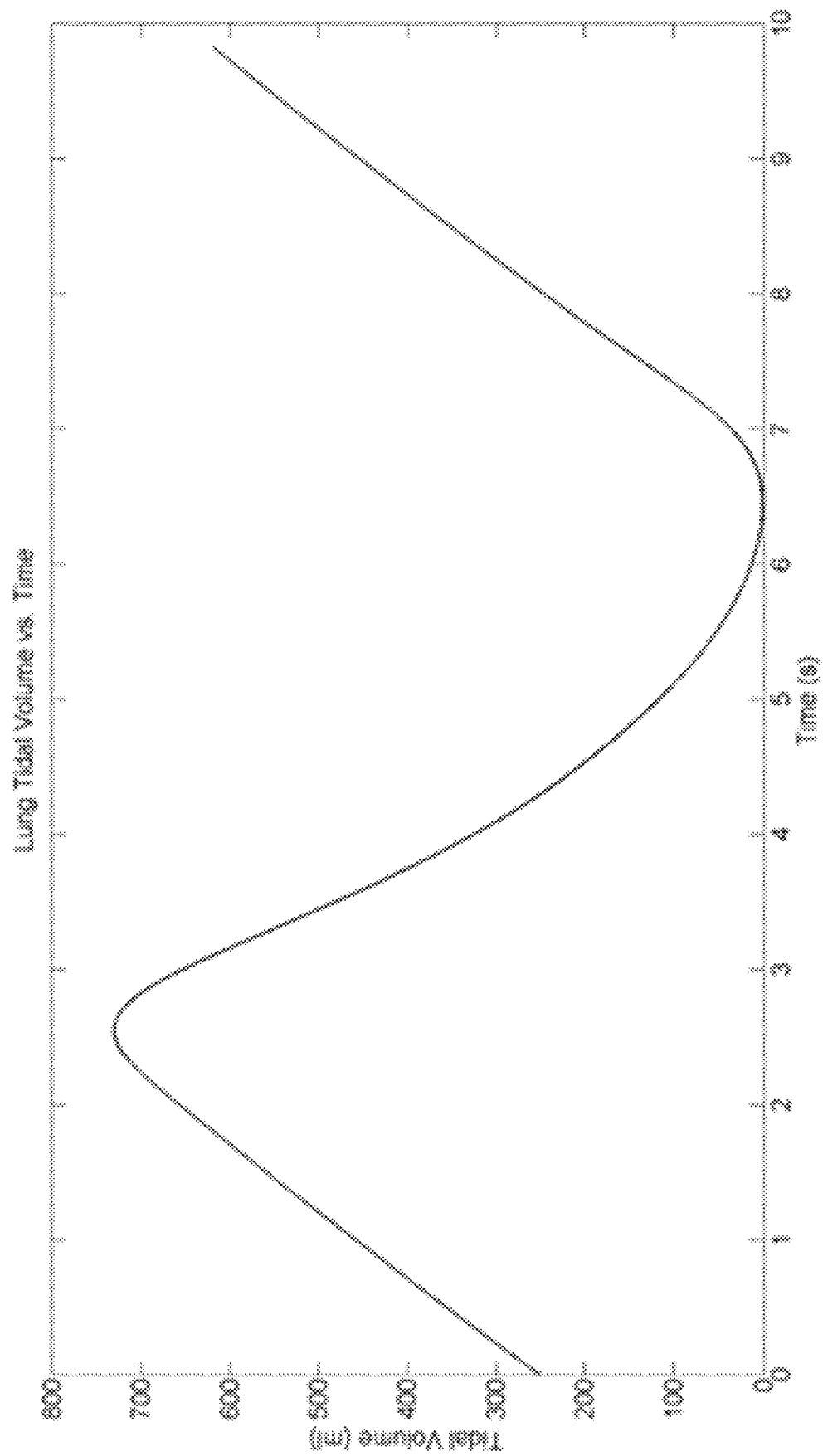
FIG. 9 depicts an exemplary breath plotted as tidal volume versus time according to some embodiments of the present disclosure.
Figure 10:
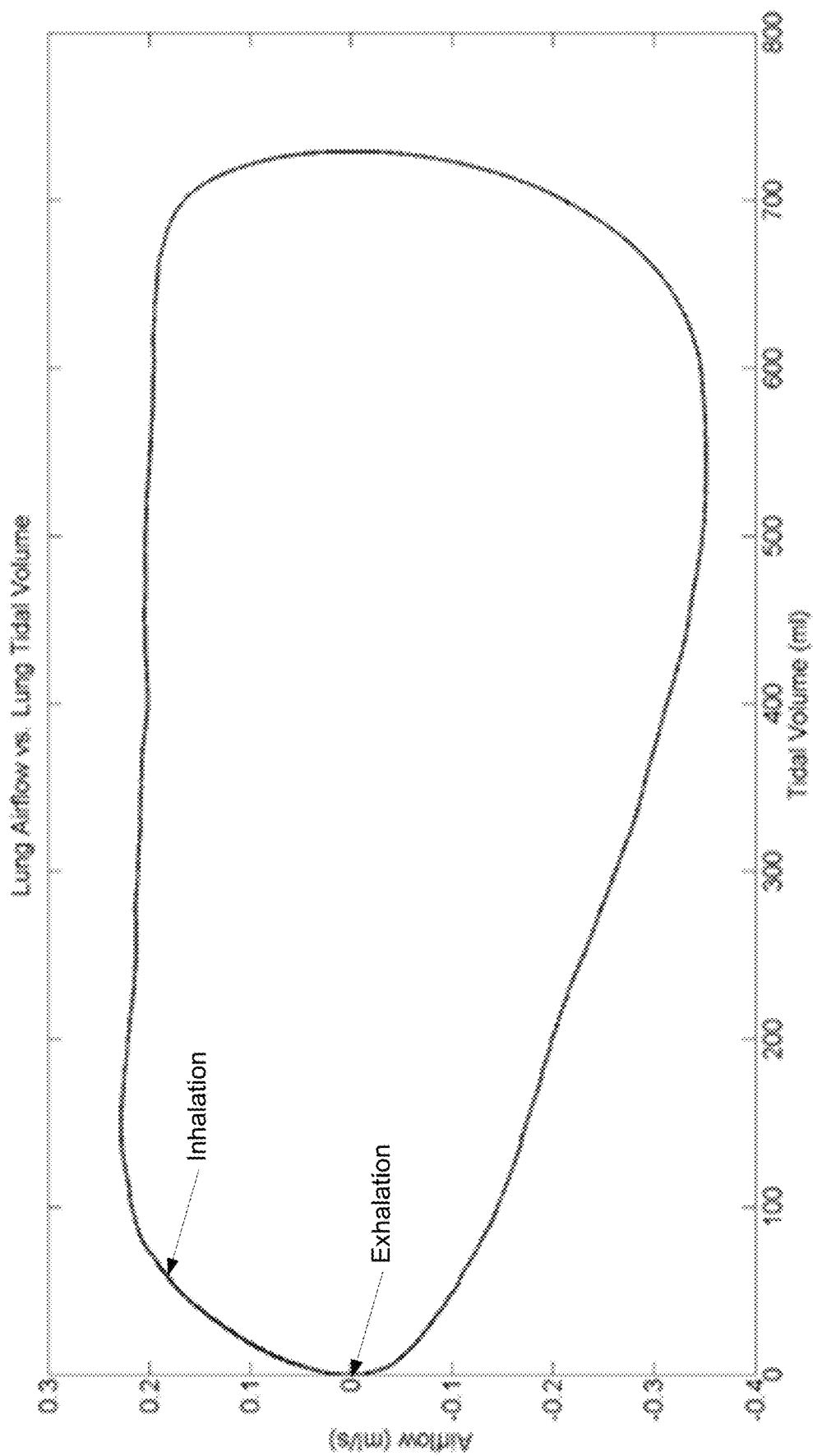
FIG. 10 depicts the same breath shown in FIG. 9 plotted as airflow versus tidal volume according to some embodiments of the present disclosure.

The acquisition software 104 needs smooth tidal volume time series to compute the first order time derivative of the tidal volume, e.g., airflow. If the tidal volume time series were not smooth, the first order time derivative of the tidal volume would not yield a smooth curve; rather, the curve would contain discontinuities that violate the biophysical realities of breathing. FIG. 9 depicts an exemplary breath plotted as tidal volume versus time according to some embodiments of the present disclosure. FIG. 10 depicts the same breath shown in FIG. 9 plotted as airflow versus tidal volume according to some embodiments of the present disclosure, which is a continuous closed loop used by the post-processing software 106 for biomechanical modeling (described in Section 3.1).

Figure 11:
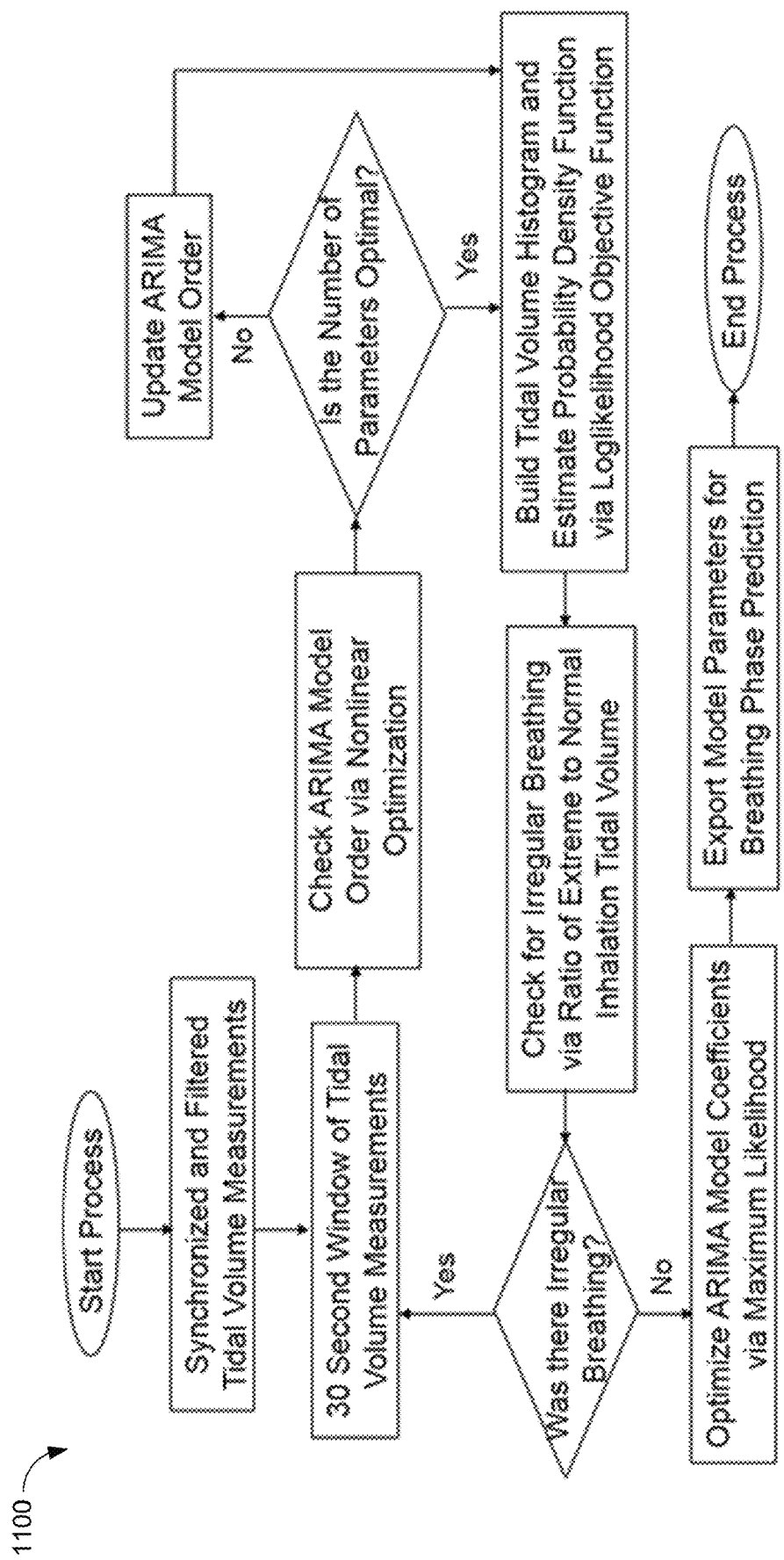
FIG. 11 is a schematic flow chart of a breathing phase prediction process according to some embodiments of the present disclosure.

The acquisition software 104 performs two distinct functions using the filtered and temporally accurate time series curves. The acquisition software 104's first function is to generate a breathing phase prediction using a short prediction horizon. FIG. 11 is a schematic flow chart of the breathing phase prediction process 1100 according to some embodiments of the present disclosure. The short prediction horizon is the prediction algorithm's "look ahead time." The prediction algorithm predicts the future moment in time at which the desired tidal volume and airflow (e.g., breathing phase) will occur. The "desired" breathing phase is targeted so that the diagnostic x-ray unit 108 can be triggered to acquire the desired chest geometry.

A short prediction horizon also mitigates another source of inaccuracy in breathing prediction, e.g., breath-to-breath variations in breathing amplitude and breathing period. As the limit of prediction horizon approaches zero, the change in the lung geometry approaches zero (e.g., the lung geometry is deemed to be virtually constant). In other words, the lung geometry is very unlikely to change dramatically during a short prediction horizon. The short prediction horizon therefore reduces the impact of human breathing variation on the breathing motion model's predictive accuracy.

Temporally accurate, filtered tidal volume time series serve as input values for the breathing prediction algorithm. The breathing prediction algorithm provides a fast, real-time, and accurate forecast of the breathing phase. For example, the breathing prediction algorithm is based on an autoregressive integrated moving average (ARIMA). ARIMA is appropriate for breathing prediction because ARIMA models do not assume that input values are stationary, and is comprised of polynomials. The polynomial coefficients of the ARIMA model are estimated during the 30-second training window taken at the start of the imaging study. The number of polynomial coefficients of the ARIMA model, e.g., model order, is checked with nonlinear optimization that seeks to minimize an information criteria search function to reduce or eliminate overfitting. If the model order is optimal for the collected training data, then builds a tidal volume histogram (discussed in Section 2.1) and calculates the probability density function using a log-likelihood objective function. The tidal volume distribution is to check for irregular breathing as discussed in Section 2.1. If irregular breathing was detected, the training data is discarded and reacquired. If irregular breathing was not detected, the training data and probability density function is used to estimate the ARIMA model coefficients with a maximum likelihood approach. The 30-second training window also serves as an equipment check prior to imaging. FIG. 11 shows the flowchart for predicting the breathing phase.

The acquisition software 104's second function is to identify the cardiac phase so that the heart is in the same phase in each desired chest geometry. The prediction horizon's duration is a crucial parameter in the acquisition software 104's endeavor to accurately predict human breathing because human breathing is a quasi-random function (because each breath has some unique aspect of its own). In some embodiments, the prediction horizon's duration is longer than the sum of the digital diagnostic x-ray unit 108's latency time and the x-ray imaging's exposure time. The sum of the digital diagnostic x-ray unit 108's latency time and the x-ray imaging's exposure time is very short, on the order of 10 milliseconds. As a result, the prediction horizon's duration is also short (on the order of 1-2 sensor measurement samples at an operating frequency of 100-1000 Hz).

When the acquisition software 104 looks for coincidence between the cardiac and breathing phases, the probability of having phases represented by a single point in each time series align is low. As a result, an imaging method that looks for single-point coincidences takes a longer time to complete since the acquisition software 104 has to wait for low probability coincidences to occur. In contrast, the cardiac gating window extends the size of the coincidence window so that the imaging study takes less time.

Figure 12:
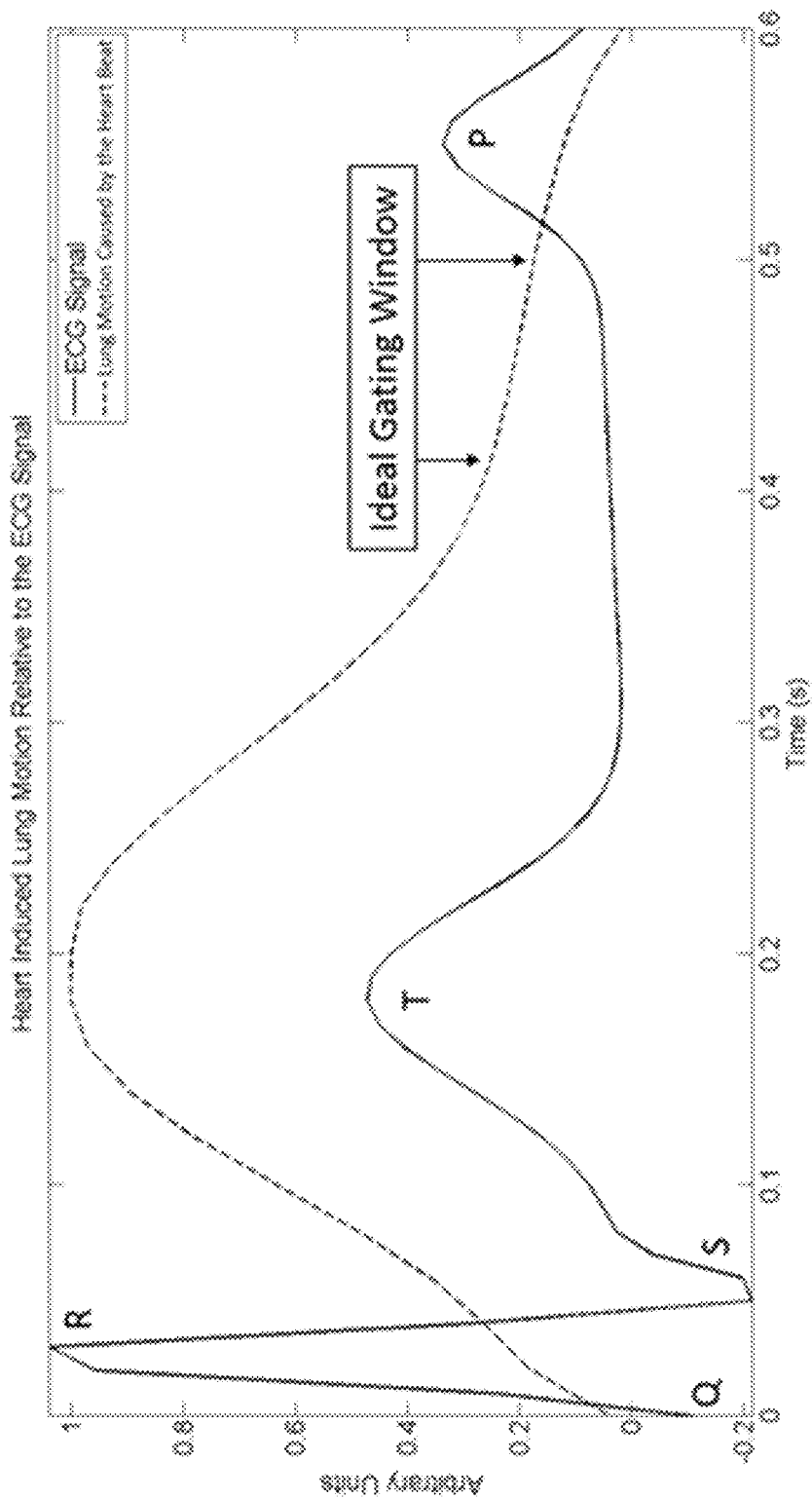
FIG. 12 depicts an exemplary gating window in time chosen based on the locations of T wave and P wave in the ECG signal such that the heart induced lung motion is changing slowly according to some embodiments of the present disclosure.

To further reduce computation time in the signal processing software, the signal processing software does not predict cardiac phase. Instead, the signal processing software targets a specific gating window in which the heart is not rapidly displacing the lung. FIG. 12 depicts an exemplary gating window in time chosen based on the locations of T wave and P wave in the ECG signal such that the heart induced lung motion is changing slowly according to some embodiments of the present disclosure. The dotted line is heartbeat-induced lung motion. Lung motion rate of change (e.g., velocity) is the slope of the dotted line. When the dotted line's slope is small, the rate of change is also small, making the corresponding cardiac phase an ideal gating window. FIG. 12 shows that the gating window occurs (consistently) between the T wave and P wave, more skewed toward the P wave. There is minimal lung motion caused by the heart beat in the gating window.

The preceding paragraph discusses how to identify the ideal cardiac gating window that would minimize the heart's physical effect on the lungs while still maintaining a window of opportunity for the targeted breathing phase to coincide with the desired cardiac phase. In some other embodiments, the GREX imaging system 100 predicts rather than gates the cardiac phase based on a signal processing difference that distinguishes the cardiac phase from the breathing phase, e.g., the cardiac phase is periodic and stable. Because the cardiac phase is periodic and stable, an unsupervised multi-layer perceptron using a backpropagation approach can be used to predict the next heart beat based on the pattern extraction rather than a time series prediction process.

Figure 13:
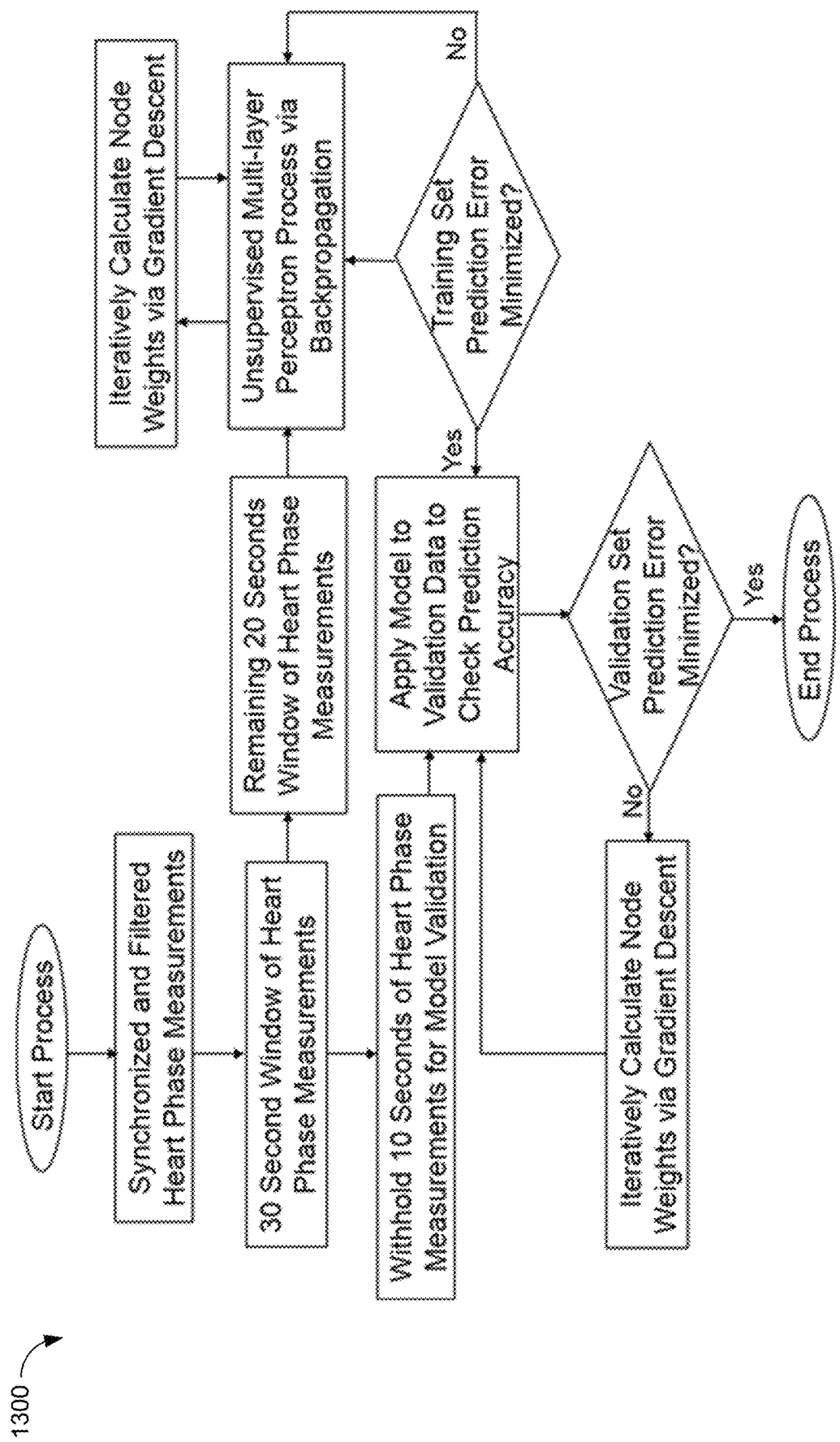
FIG. 13 is a schematic flow chart of another GREX procedure using cardiac phase prediction instead of real-time identification of a cardiac gating window according to some embodiments of the present disclosure.

FIG. 13 is a schematic flow chart of another GREX process 1300 using the cardiac phase prediction instead of real-time identification of a cardiac gating window according to some embodiments of the present disclosure. In this case, twenty seconds of the training window (20-22 heartbeats) is used for training the algorithm while the remaining ten seconds (10-11 heartbeats) is used for validating the multi-layer perceptron node weights. Node weights are iteratively determined through gradient-descent optimization until the model error in the training set is minimized. The trained model is applied to the 10-second validation data and node weights are recalculated if the multi-layer perceptron provided poor prediction of the cardiac phase in the validation data.

Section 2.3—Logic Algorithm 118

There are known medical algorithms and systems for identifying an ECG's T wave and P wave within a cardiac cycle. Because the heart phase sensor 112 takes continuous measurements of the cardiac cycle, the time interval between the T wave and the subsequent P wave (which is equal to a constant fraction of the cardiac cycle, and is thus proportional to the heart rate) is also known. The ECG features within the time interval can be used by the logic algorithm 118 to introduce a short time lag before initiating the gating window such that the gating window may start, e.g., halfway between the T and P waves and close after the logic algorithm 118 identifies the P wave.

Figure 14:
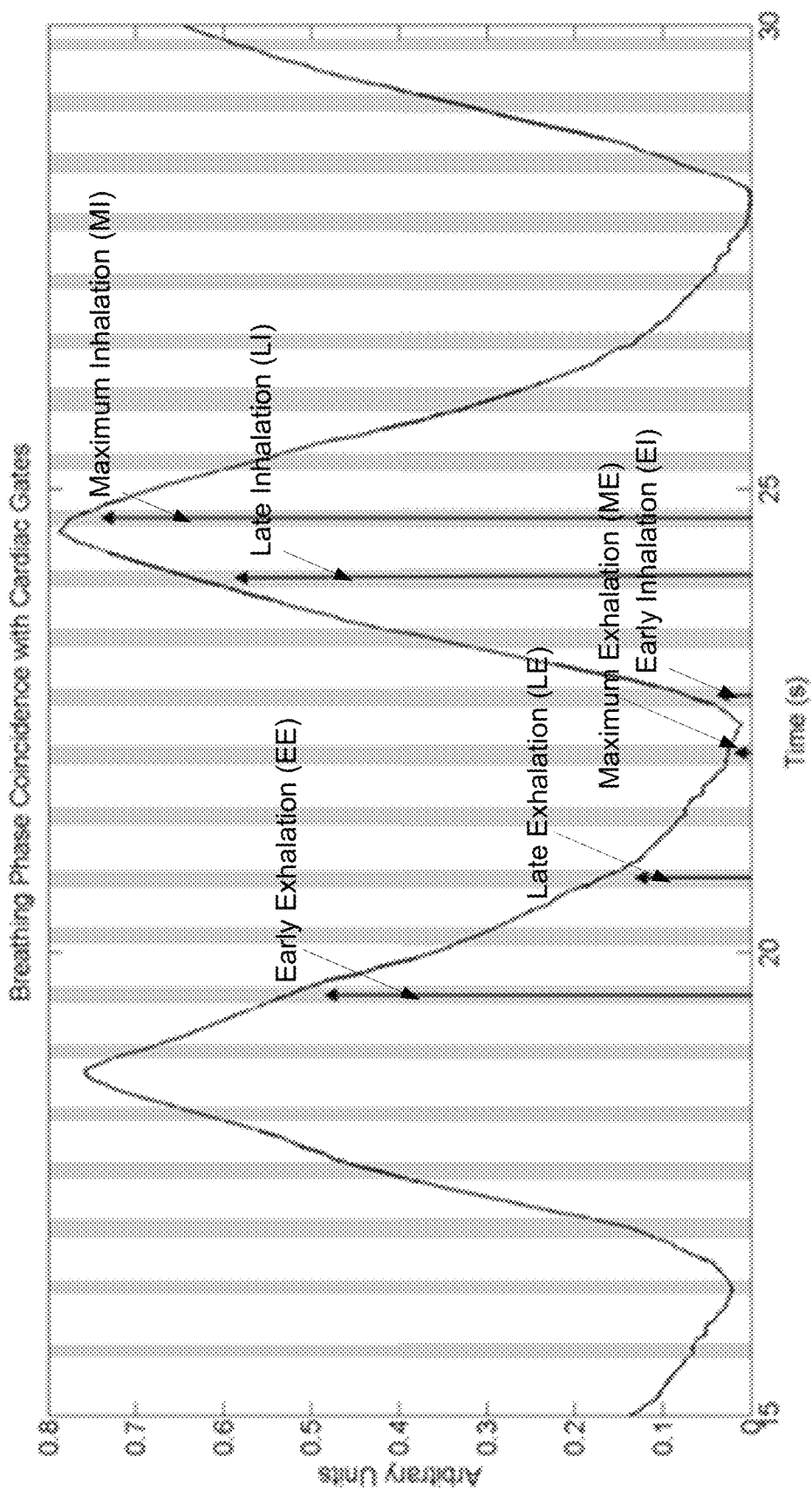
FIG. 14 depicts an example of triggered images, from left to right, at early exhalation, late exhalation, maximum exhalation, early inhalation, late inhalation, maximum inhalation of a breathing phase according to some embodiments of the present disclosure.

FIG. 14 depicts an example of triggered x-ray image capturing windows corresponding to different breathing phases of a breathing cycle, from left to right, early exhalation, late exhalation, maximum exhalation, early inhalation, late inhalation, maximum inhalation of a breathing cycle according to some embodiments of the present disclosure. In this example, the acquisition software 104 identifies a minimum of six breathing phases that represent a single breath cycle. During the training period, the acquisition software 104 generates a distribution of samples and the logic algorithm 118 computes the tidal volume percentiles that will define the logic algorithm 118's targeted breathing phases. The arrows shown in FIG. 14 denote the six cardiac gating windows that coincide with the targeted breathing phases for which the logic algorithm 118 would create an imaging trigger signal. Once the acquisition software 104 acquires a breathing phase, it creates an automated check that prevents future redundant imaging of the same breathing phase.

Figure 15:
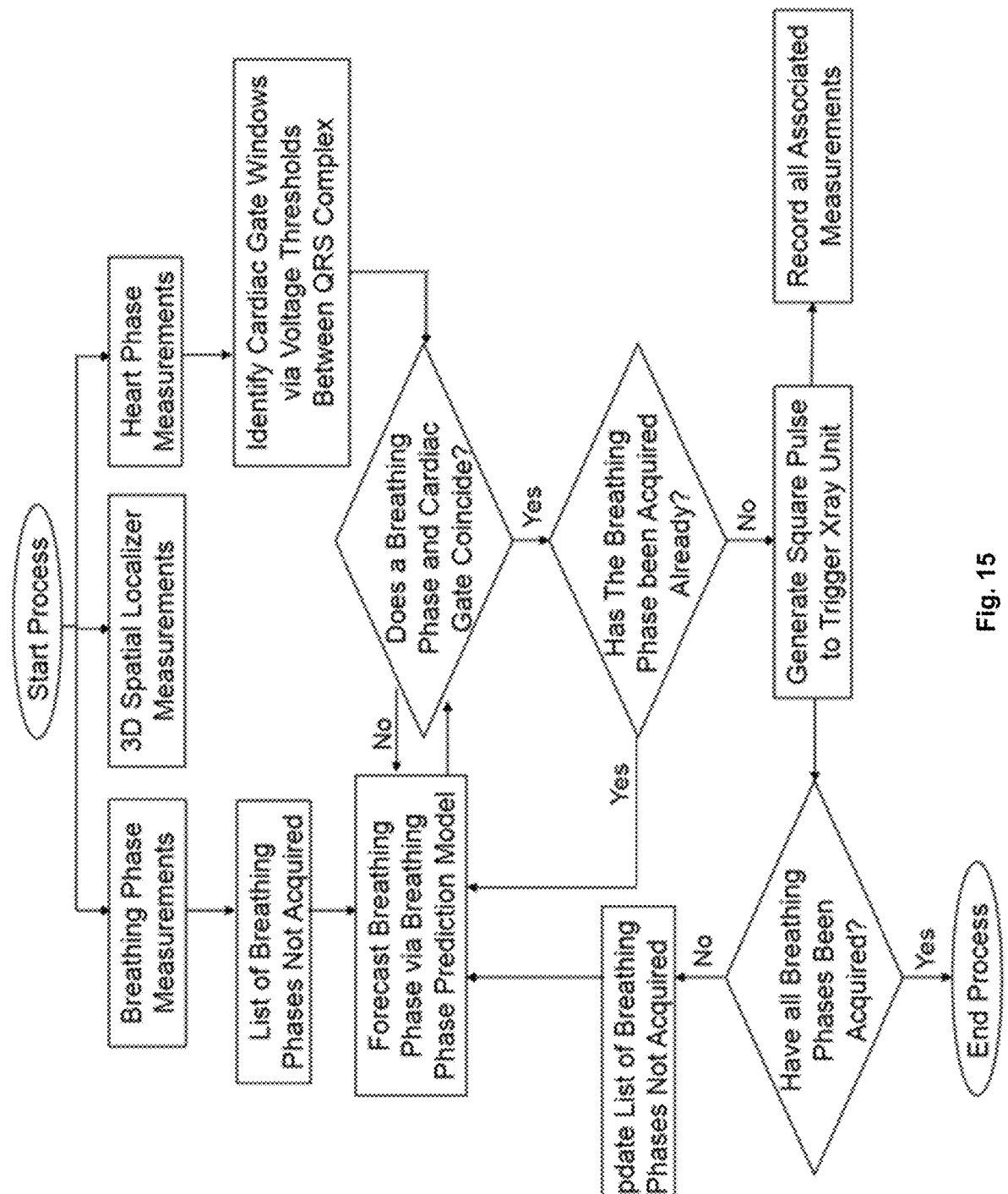
FIG. 15 is a schematic flow chart of an image acquisition triggering process according to some embodiments of the present disclosure.

FIG. 15 is a schematic flow chart of an image acquisition triggering process 1500 according to some embodiments of the present disclosure. The cardiac phase sensor measurements are used to identify the cardiac gating window as previously described in connection with FIG. 12. The breathing phase sensor 110's measurements are used to forecast the breathing phase as previously described in connection with FIG. 11. The logic algorithm 118 identifies coincidence between the cardiac phase gating window and predicted breathing phases. When a coincidence is found, a list of breathing phases is checked to determine if the breathing phase has already been acquired or not. If the breathing phase was previously acquired, an imaging trigger pulse is not created. If the breathing phase was not previously acquired, an imaging trigger pulse is created, which takes a snapshot of the patient anatomy. The breathing phase, cardiac phase, and 3D spatial position localizer 300 measurements are recorded and tagged with the image. If all breathing phases have been acquired, the breathing phase list is updated to prevent redundant images from being taken.

Section 2.4—Trigger Generation (Gating)

X-ray unit 108 has a port that contains a series of electrical pins. One of those pins accepts an electrical impulse that defines the radiation exposure timing and duration. Based on the logic algorithm 118's identified breathing phases within a cardiac gating window, the trigger generator generates a square wave trigger as an electrical impulse. A fiber optic cable with a vendor-specific plug attachment carries the generated trigger signal to the x-ray unit 108.

Section 3. Post-Processing Software

The biometrically-informed imaging trigger identified by the hardware box 102 (Section 1) and acquisition software 104 (Section 2) provides better quality inputs (and remove poor quality inputs) to the image reconstruction algorithm. Specifically, the quality enhancement arises from the fact that image reconstruction and image post-processing techniques are enhanced through the process of acquiring biometrically targeted images during normal breathing. The act of biometrically targeting images during the normal breathing allows for more accurate association of multiple images of the same patient's anatomic geometry taken from different angles and at different times (e.g., different breaths) because the fundamental assumptions of the underlying radiology mathematics assume anatomical equivalence across the various probed imaging angles. The enhanced images serve as observations and the biometric signals serve as inputs for a complex biomechanical model of the chest geometry.

Section 3.1—Digital Tomosynthesis-Based GREX Image Acquisition

Multiple imaging angles are needed to reconstruct a 3D volume. In the context of the GREX imaging, each angle needs to be acquired for each breathing phase. The acquisition software 104 (Section 2) creates a trigger signal that allows the x-ray unit 108 to repeatedly image the chest in a specific geometry. Identical geometries imaged at different imaging angles and different breaths constitute a set of 2D projection images that are used to reconstruct the 3D volume. There are many known methods of reconstructing a 3D volume from the multiple 2D projection images. One such exemplary method is a convolution-back-projection algorithm for direct reconstruction of a 3D density function using a set of 2D projections called "FDK image reconstruction algorithm" disclosed in Feldkamp, L. A., Davis, L. C., Kress, J. W. "Practical cone beam algorithm". *J Opt Soc Am* 1, 612-619 (1984).

Figure 16:
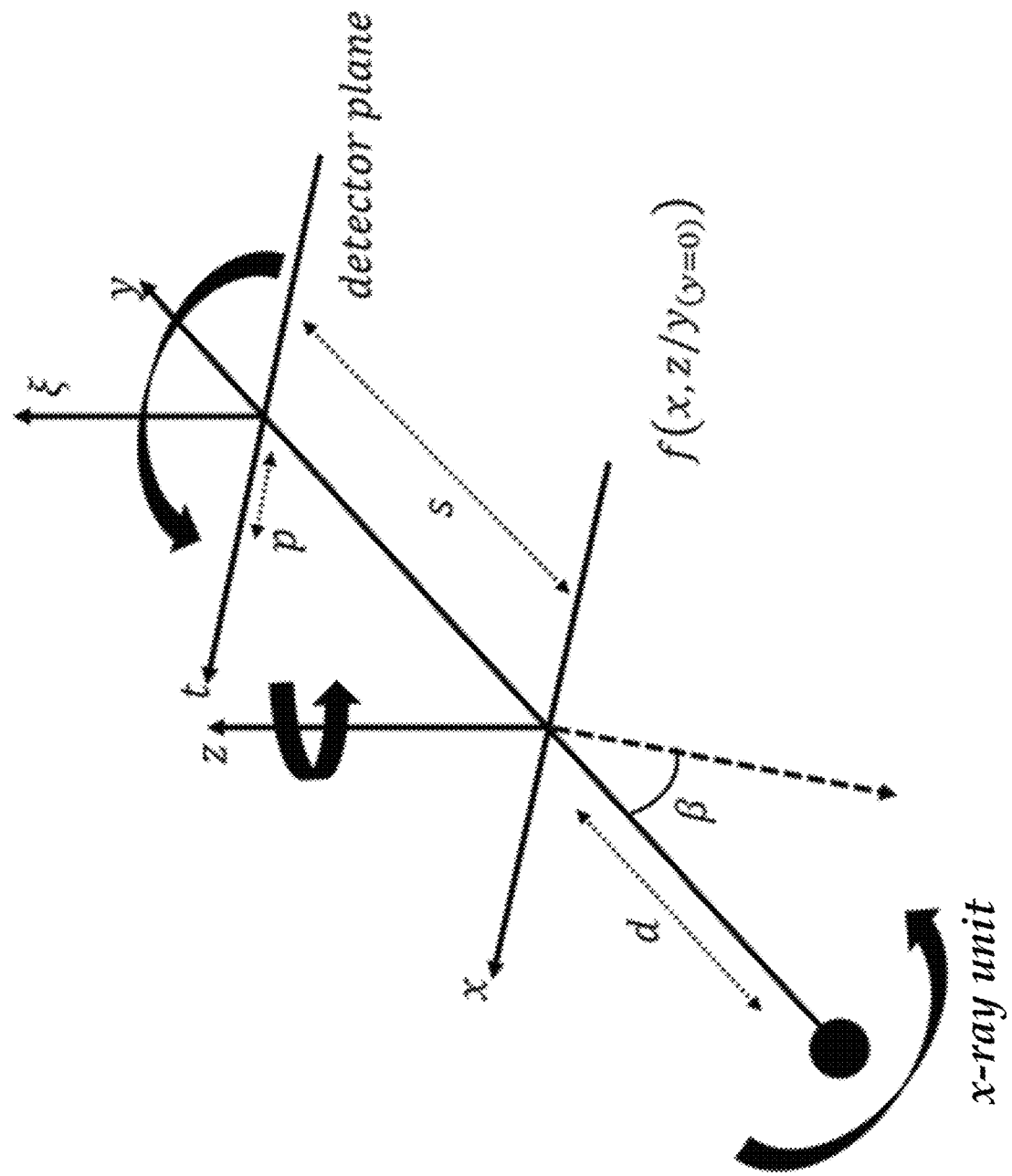
FIG. 16 is a schematic block diagram of variables used in an exemplary GREX image reconstruction algorithm according to some embodiments of the present disclosure.
Figure 17:
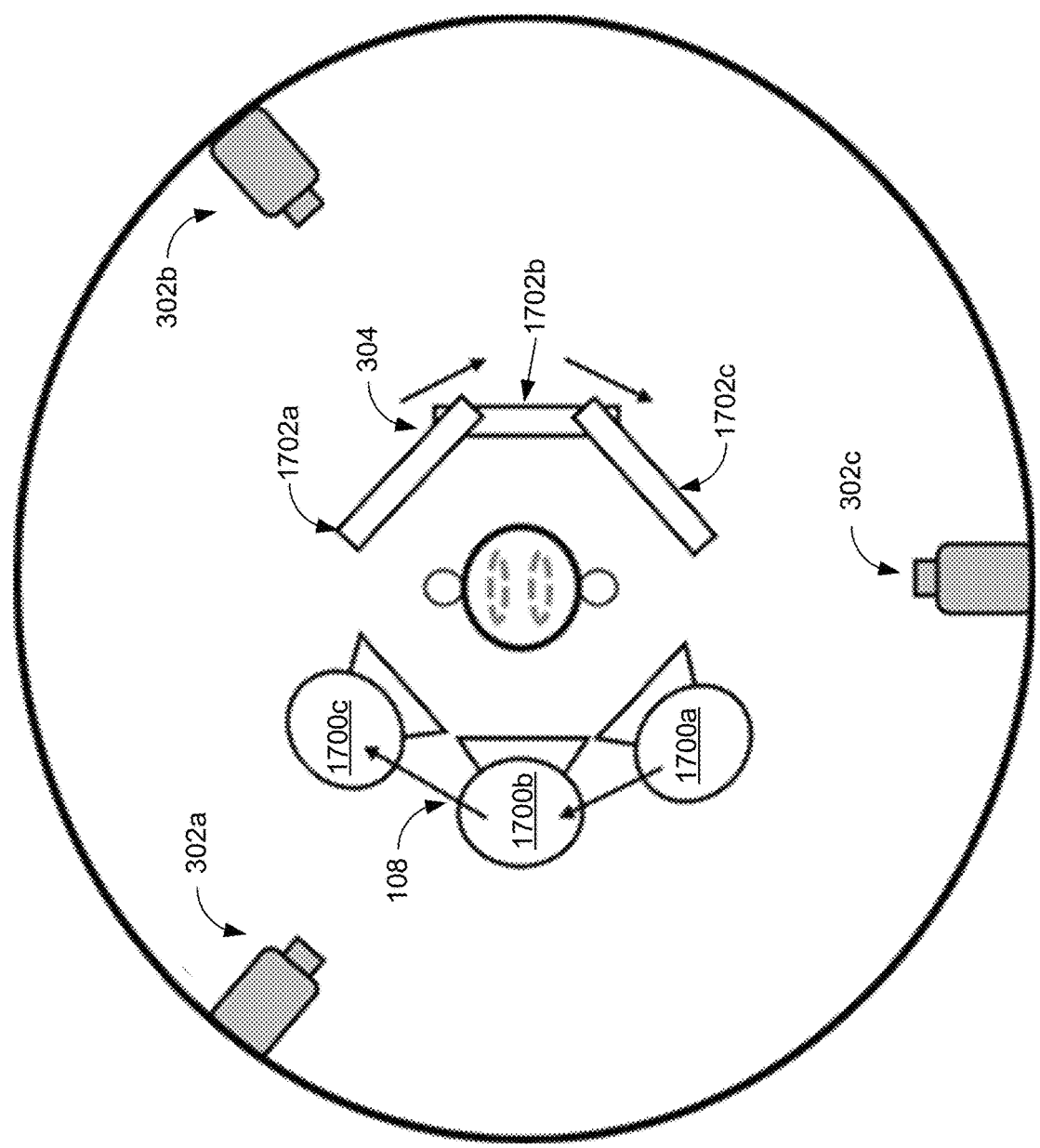
FIG. 17 is a schematic block diagram of operating components of the GREX imaging system during an imaging procedure according to some embodiments of the present disclosure.

FIG. 16 is a schematic block diagram of variables used in the image reconstruction algorithm according to some embodiments of the present disclosure. Once a single projection is acquired, the x-ray unit 108 moves an angle β and the detector plane moves to stay perpendicular to the x-ray unit 108. In some embodiments, a patient is moved and the x-ray unit 108 remains in a same position between acquired projections. FIG. 17 schematically shows an example of how the x-ray unit 108 and detector panel 304 from FIG. 3 move to acquire multiple imaging angles. For example, x-ray unit 108 moves from position 1700a to position 1700b to position 1700c. Detector panel 304 moves from position 1702a to position 1702b to position 1702c. The detector plane is rotating around the axis parallel to the detector plane, and the imaging plane rotates around its parallel axis, z. The position of a pixel in the detector plane and a corresponding pixel in the imaging plane is separated by a distance, s. Anatomic information (f(x,z/y)) in the image plane ((x, z) plane), at an arbitrary depth y is calculated by Equation (1).

$$f(x, z/y) = \frac{1}{N_0} \int_{min\beta}^{max\beta} \frac{d^2}{(d-s)^2}$$

$$\int_{-\infty}^{\infty} \frac{d}{\sqrt{d^2 + p^2 + \xi^2}} \times R(\beta, p, \xi) h\left(\frac{d \cdot t}{d-s} - p\right) W(p) dp d \quad (1)$$

In Equation (1), $N_0$ is the total number of projections, β is the angle of each projection, d is the source-to-image plane distance, s is the pixel-to-detector distance, p is the detector axis perpendicular to the rotation axis, ξ is the detector axis parallel to the rotation axis, R(β, p, ξ) corresponds to cone beam projection data (e.g., the function R is the detector readout for a given angle, p coordinate, and ξ coordinate), h is the convolution filter, and W(p) is a weighting function. Basically, Equation (1) represents a combination of convolution, back-projection, and weighting steps.

Information at points that lie in the mid-plane is calculated from the projection data along the intersection of the detector plane and the mid-plane (y=0). Projections that intersect the detector plane along a line parallel to the mid-plane, but not in it (constant, nonzero y), themselves define a plane. This plane is treated as if it were the mid-plane of another, tilted arrangement. If a complete set of projections are acquired (note that "complete" denotes the case where all rotation angles about the normal are acquired) the tilted plane's density is reconstructed using the Radon transform. Acquiring a complete set of projections requires a 360° rotation of the source around the imaging object along a circle in the tilted plane; In CT imaging, for example, a full 360° rotation around the imaged object occurs. Note that the bolded words "the imaging object" imply—more accurately, the bolded words explicitly communicate and define—the fundamental assumption of the Radon transform (folded into Equation (1)'s R(β, p, ξ) term) that, if violated, stymies the reconstruction's representativeness of the underlying ground truth anatomy that was imaged: "The imaging object" implies that Radon transform inputs are assumed to be different angular probes of one single, fixed, non-moving and non-changing in time and space, stationary object of anatomy. The GREX imaging's biometric targeting (indeed "pre-selection") of only the accurate (the geometrically identical breathing phases that are identical despite occurring in different breaths) Radon transform inputs adheres to the transform's fundamental assumption definitionally and practically, since breathing phase (that is: changing in the time domain) is for GREX defined strictly geometrically and anatomically and physically (e.g., a definitionally correct formulation) and also practically with GREX imaging's uniquely short prediction horizon and prospective biometric targeting.

Figure 18:
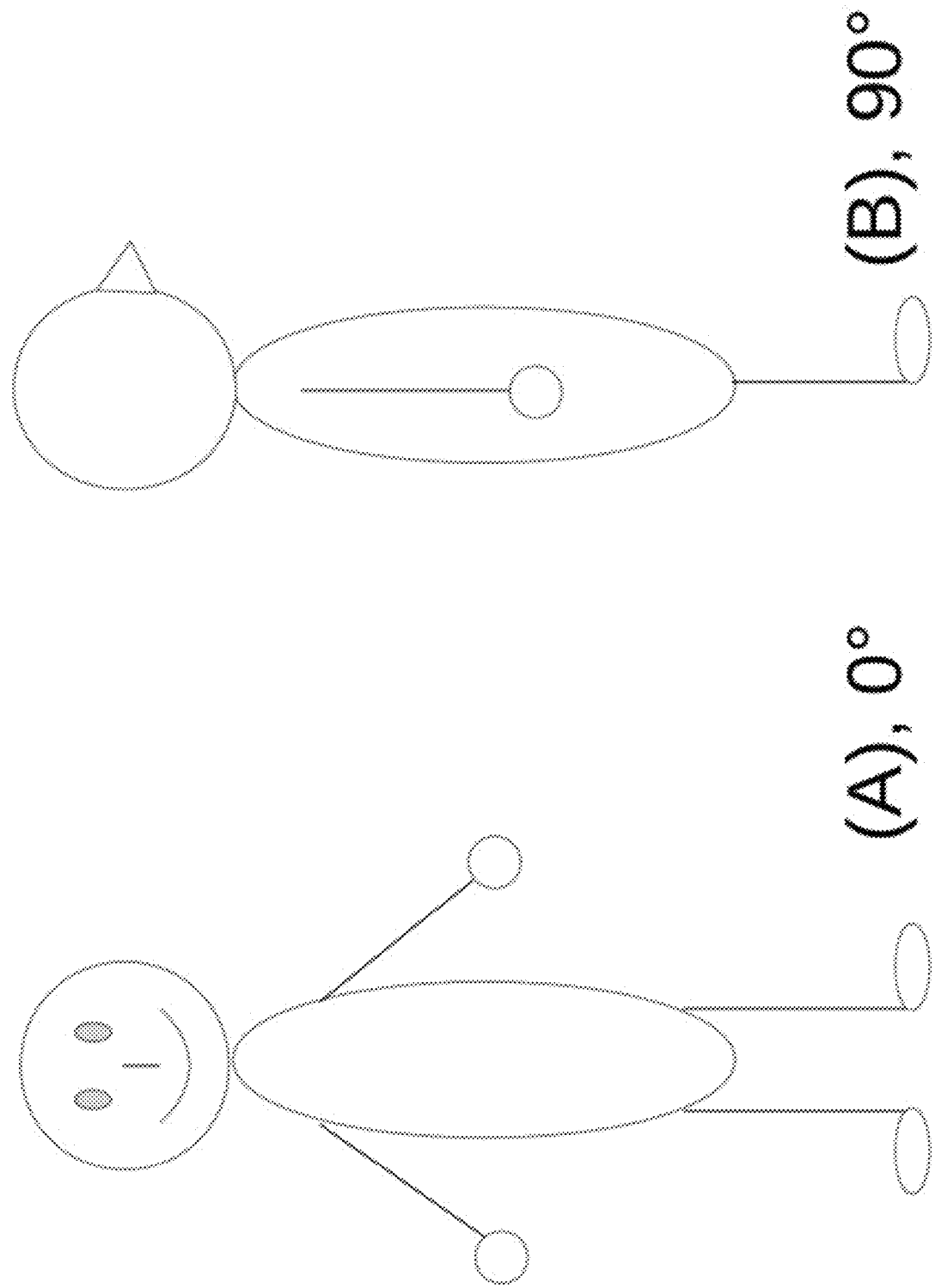
FIG. 18 is an exemplary depiction of the tissue depth a 0° (A) and 90° (B) x-ray projection traverse according to some embodiments of the present disclosure.

Note that 360° rotation is not practical for GREX imaging because the high number of projections needed to reconstruct the torso's 3D volume increase clinical procedure time and increase patient dose of radiation. Instead, GREX imaging may use projection angles ranging up to 90° between −45°≤β≤45° or 0°≤β<90°. One skilled in the art would understand that experimental testing may identify more optimal projection angle ranges, but the theoretical projection angle ranges does not exceed 90°. In some cases, the −45°≤β≤45° is likely preferable to the 0°≤β<90° because the −45°≤β≤45° keeps the radiation dose from the imaging procedure as low as reasonably achievable. The x-ray photons traverse less human tissue in the −45°≤β≤45° projection angle range compared to the 0°≤β≤90° projection angle range, and therefore can be lower energy photons thereby depositing less dose, as shown in FIGS. 18A and 18B.

To produce a high quality 2D image without delivering excessive radiation dose, photon energy must be high enough to partially penetrate the patient's body but not too high so that the photons totally penetrate the patient. Thicker patients require higher photon energy than thinner patients. When |B|>45°, the human body is substantially thicker than when |B|<45°. In general, as β→0° the photon energy decreases. In some embodiments, the GREX imaging system 100 acquires six breathing phases at five distinct projection angles for a total of 30 projections although other different numbers of projections may be possible depending on the specific application of the GREX imaging technology. For example, in breast tomosynthesis, the symmetric curvature of the breast means that the breast surface is essentially equidistant from the source at all projection angles, meaning that tomosynthesis is well suited for breast. Furthermore, the breasts do not move when placed in a cradle, a typical clinical tomosynthesis approach that could be analogized to breath-hold lung imaging.

With the lung and heart motion challenge resolved by the GREX-based geometric definition of breathing phase plus GREX-based highly accurate and fast prospective targeting prediction algorithm (Section 2.1 and 2.2, respectively), the GREX imaging system 100 can handle the varying torso curvature with the biometric surface information gathered by 3D Spatial Positioning Localizer (Section 1.1). Biometric surface information also assists in the image post-processing to account for attenuating tissue density in the imaging field, thus quantifying previously neglected sources of attenuation and ultimately resulting in higher fidelity image reconstruction. In sum, the GREX imaging technology makes it possible for the digital tomosynthesis to work for non-breath-hold ("dynamic") lung and heart imaging.

GREX-based approach to 3D volume reconstruction can be either patient-specific (personalized medicine, with a personalized number of discrete angles and arc subtended) or used as a "universal minimum procedure time and universal minimum delivered dose" (in the neighborhood of 5 discrete angles, plus or minus 3 angles depending on the statistical reconstruction methods used and number of prior GREX-based datasets available for the person).

Figure 19:
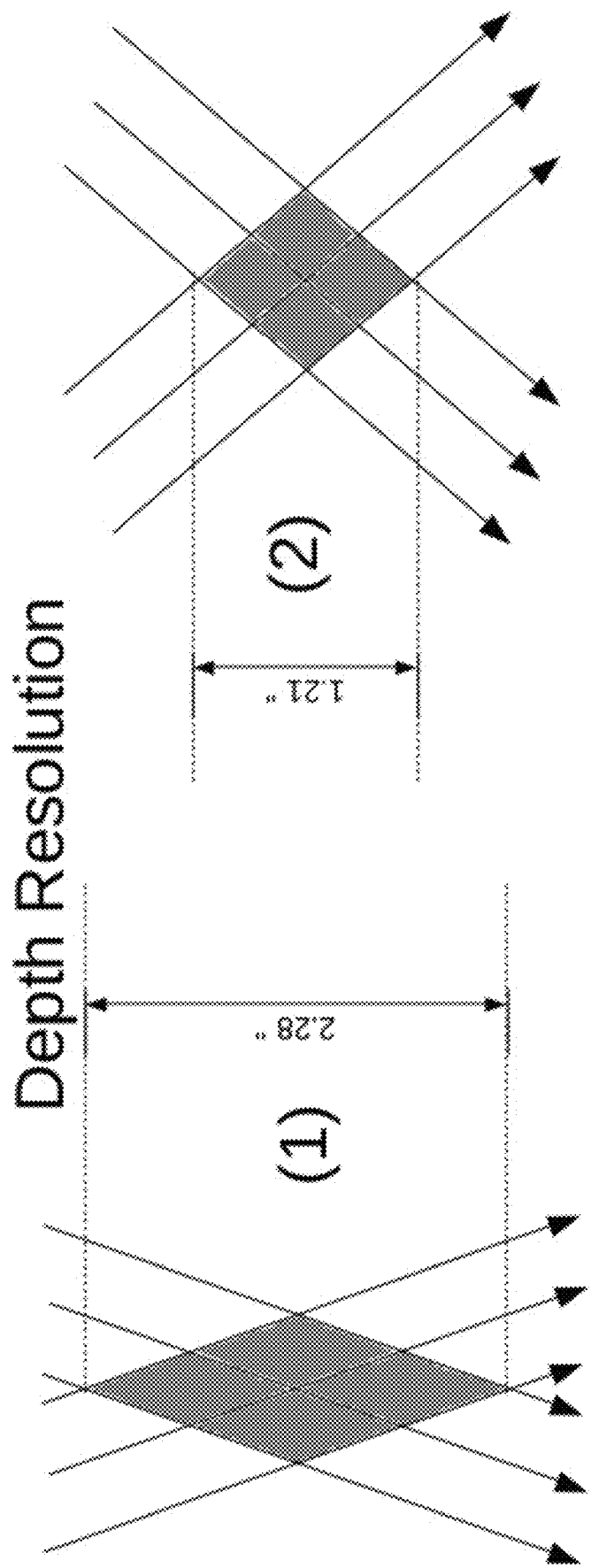
FIG. 19 is an exemplary depiction of depth resolution from a narrow projection angle range (1) and a wide projection angle range (2) according to some embodiments of the present disclosure.

As shown in FIG. 19, when the rotation of the x-ray unit 108 subtends a small range of angles, the depth resolution is lower than when the rotation of the x-ray unit 108 subtends a wider range of angles. Any motion, no matter how small, causes image artifacts in the reconstructed image which commonly leads to false-positive cancer detection. But the GREX imaging system 100's unique hardware box 102 (Section 1) collects biometric signals that inform the acquisition software 104 (Section 2) when to take an image so that the chest geometry is clinically identical, thereby making smart chest digital tomosynthesis possible.

In some embodiments, the GREX imaging technology allows the projection angle to vary during one breathing phase whereas multiple projection angles captured at different time points (as defined by GREX imaging's quantitative definition of "breathing phase") still all correspond to the same breathing phase because they are deemed to be all capturing one chest geometry. Moreover, the GREX-based tomosynthesis approach allows the acquisition of depth information because the detector's final photon count numbers across all pixels and the distribution of photon counts in space at the detector surface are reflective of a single chest geometry that has been probed at multiple angles.

Note that the GREX imaging technology allows the x-ray unit 108 and detector panel 304 to be mounted on unmotorized arms or stands. The manual arm's role in an exemplary GREX imaging procedure is described and illustrated in FIG. 20 as follows:

1. At the $\beta_1$ position, all the requisite 6 chest geometries (a.k.a. "GREX's quantitatively defined breathing phases") are imaged.
2. Then the clinician physically reorients the x-ray unit 108 and the detector panel 304 to image the patient at position $\beta_2$.
3. The orientation of the x-ray unit 108 and detector panel 304 relative to the patient is verified by the 3D Spatial Localizer, which allows imaging to take place at $\beta_2$.
4. Now at $\beta_2$: If only 4 out of the 6 required chest geometry images are acquired during the first breath, the patient simply continues breathing as normal at position $\beta_2$ for subsequent breaths until the remaining 2 chest geometry images are acquired.
5. Now that all 6 breathing geometries have been acquired at $\beta_1$ and at $\beta_2$, the x-ray arm can now be relocated to acquire each imaging angle in turn from ($\beta_2 \rightarrow \beta_3$; $\beta_3 \rightarrow \beta_4$; $\beta_4 \rightarrow \beta_5$).
6. By the end of the procedure, the x-ray arm only moves a total of 4 times, as denoted by the → arrow in the workflow ($\beta_1 \rightarrow \beta_2$; $\beta_2 \rightarrow \beta_3$; $\beta_3 \rightarrow \beta_4$; $\beta_4 \rightarrow \beta_5$).

By moving the arm only 4 times during the procedure, the GREX imaging technology minimizes the length of the procedure, the extent of clinician-equipment interaction during the procedure, and the extent of wear-and-tear to the x-ray arm because the clinician is not interacting with the x-ray arm as much as moving the arm from β1 through β5 for all 6 breathing phases (e.g., performing 30 x-ray equipment reorientations).

In some embodiments, the 3D Spatial Positioning Localizer allows for a-priori position checks and safety interlocks of three individual elements separately—namely the patient's posture and position, the x-ray unit 108's position, and detector's position in space—as well as the collective consistency of each element's position/alignment upon an axis & relative to the position of the other elements. This a-priori position check and safety interlocks result from GREX imaging's defining the breathing phase geometrically. Therefore, the GREX imaging system 100 (via the prospective breathing phase prediction algorithm) is inherently suitable for giving users software-based safety and quality assurance control capabilities that (in the case of a safety interlock) prevent the triggering algorithm from initiating "beam on" if either (or both) the x-ray arm or detector or patient posture were incorrectly positioned in space (or inconsistent) for a specific angle, β.

In some embodiments, since the 3D Spatial Positioning Localizer records the coordinates of all equipment during a procedure, image reconstruction techniques can benefit from the (a-posteriori) quantification of each β angle and its associated uncertainty.

Figure 21A:
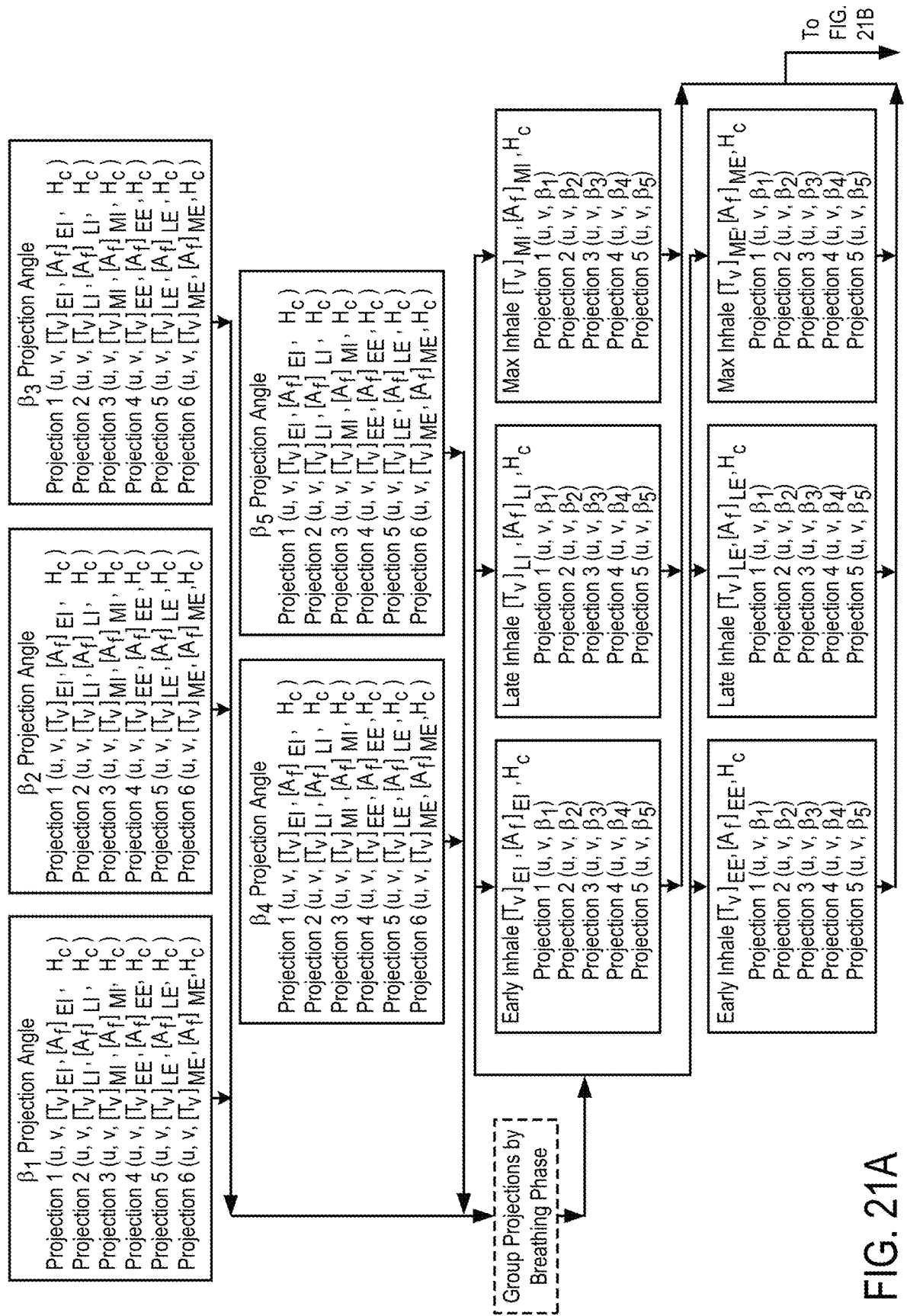
FIGS. 21A and 21B are an exemplary block diagram illustrating how the GREX imaging system transfers 2D x-ray projections into static image cubes and ultimately to an image cube movie according to some embodiments of the present disclosure.
Figure 21B:
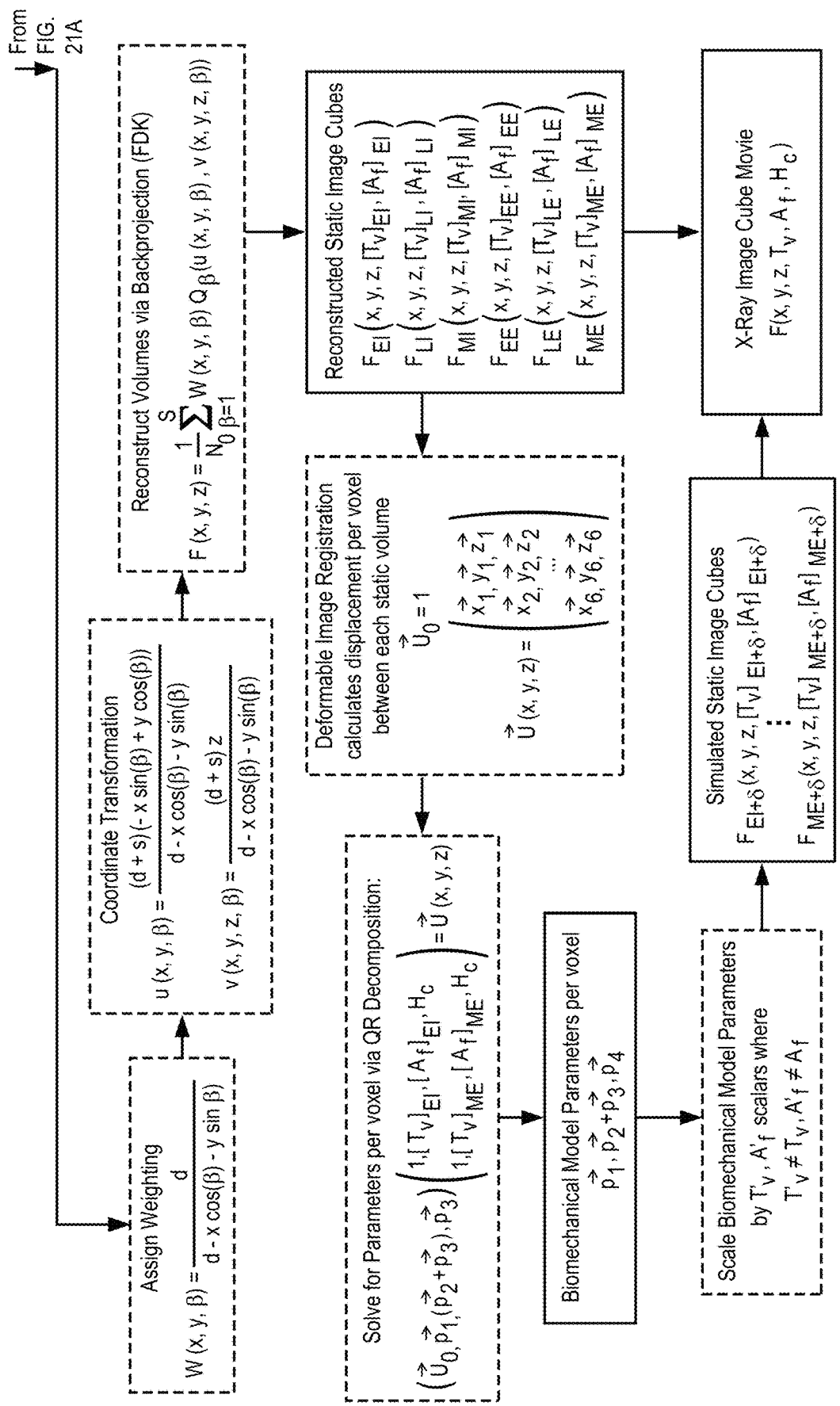

FIGS. 21A and 21B are an exemplary block diagram illustrating how the GREX imaging system 100 reconstructs static image cubes from the 2D projection data taken from each imaging angle position according to some embodiments of the present disclosure. Specifically, FIGS. 21A and 21B illustrates an exemplary GREX imaging case where the coronal and sagittal views themselves form the outer limit/boundary of the imaging angle positions (e.g., projection angles). The $i^{th}$ plane x-ray projection is taken at a single imaging angle position ($\beta_i$) for each of the 6 breathing geometries. The sum of the i=1 through i=n Plane Projections then inform reconstruction (Equation 1) of depth information in (x,y,z) of the ($v_1, f_1$) geometry that has been probed using the i=1 through i=n Projections, each of which has a plane of focus at a unique (compared to the other projections) depth.

2D projection data is acquired six times (for early inhale (EI), late inhale (LI), max inhale (MI), early exhale (EE), late exhale (LE), and max exhale (ME) at each projection angle (β). For simplicity, the projection angles range from 0° to 90°. The x-ray unit 108 will move to the next projection angles only when all breathing phases are acquired at the prior projection angle. The 2D projections are sorted according to breathing phase so that a static image cube is reconstructed (e.g., from the $\beta_i$=1 to the $\beta_i$=n projection angles that probed the chest geometry at (v1,f1)) to represent the chest volume at each breathing phase. The static image cubes are then temporally interpolated using the methods discussed in Section 3.3 below.

Figure 22:
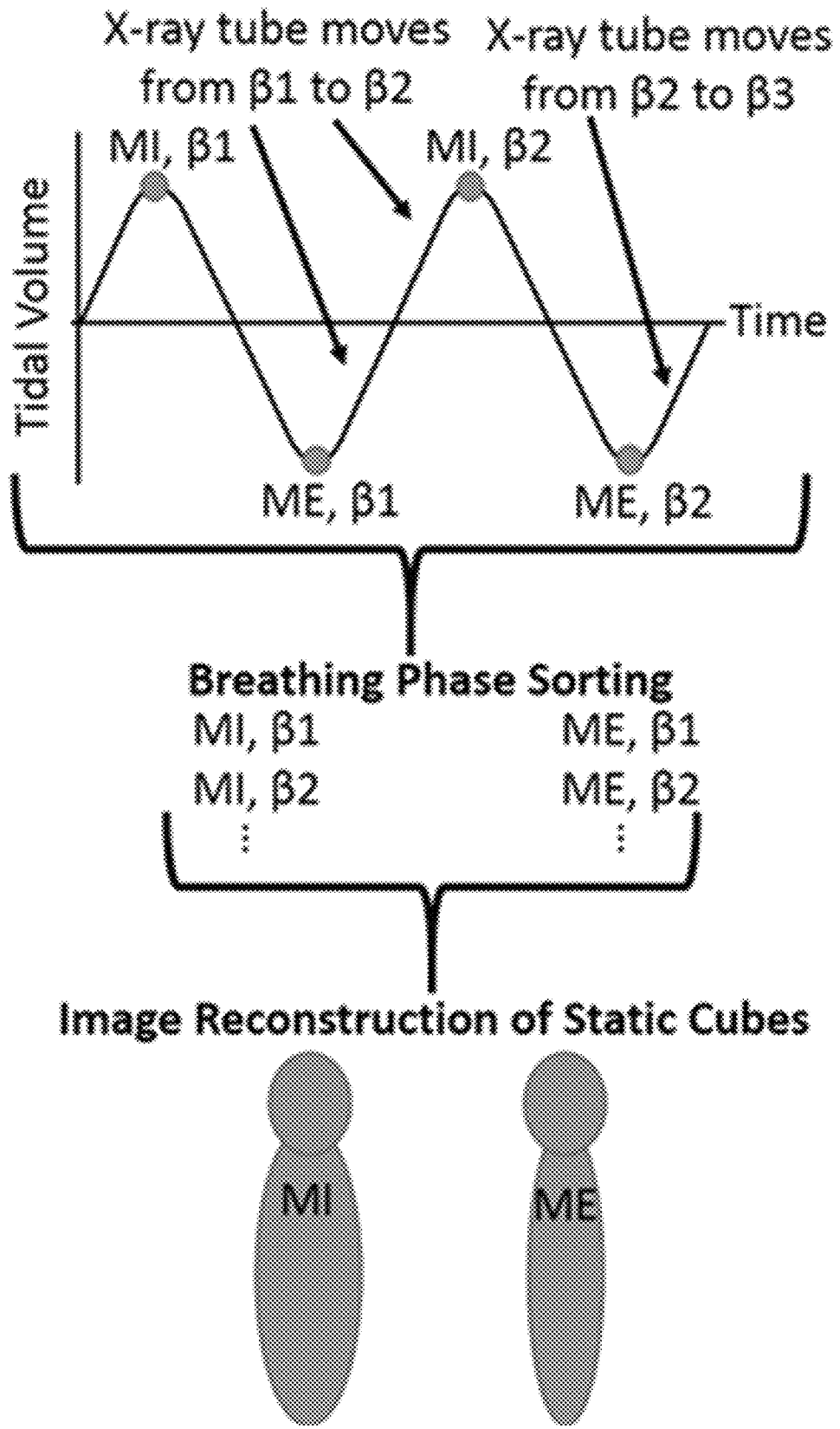
FIG. 22 is a graphic depiction of the process of creating static image cubes shown in FIG. 21 according to some embodiments of the present disclosure.

The x-ray projections acquired at each angle β are taken at the targeted breathing phases identified using the ARIMA model (Section 2.2). After the targeted breathing phases are acquired, the x-ray unit 108 moves to the next imaging angle position. FIG. 22 shows an example that only maximum inhalation and maximum exhalation are acquired by the acquisition software 104. In the example, the maximum inhalation and maximum exhalation are imaged at $\beta_1$ then the x-ray unit 108 moves to $\beta_2$ so that maximum inhalation and maximum exhalation phases can be acquired at $\beta_2$. When the targeted breathing phases are acquired at all the imaging angle positions, the images are sorted according to their respective breathing phases. Sorting x-ray images according to the breathing phase groups the projections according to the biometrically-defined six breathing phases. Although the breathing phases are acquired during different breaths, the accurate ARIMA model ensures that the tidal volume and airflow parameters are identical between x-ray projections captured at different projection angles. Note that GREX imaging defines "the same chest geometry" biometrically, such that the lung resides in "the same chest geometry" at multiple time points. GREX imaging probes the same biometric breathing phase at different angles because the ARIMA model (Section 2.2) is a fast prediction method. Chest geometry prediction errors are minimized using the short prediction horizon of the ARIMA model. The associative equivalence of each individual angle's depth information (to, in aggregate, generate real structural depth information) depends on the equivalence (consistency, within approximation tolerance) of chest geometric position across the different probed angles. As such, the breathing phase prediction accuracy ensures the successful image reconstruction.

The breathing phase-sorted projections are used to create static image cubes through the previously discussed canonical FDK image reconstruction algorithm given in Equation (1) (or a similar cone-beam geometry image reconstruction algorithm). The image reconstruction algorithm uses the breathing phase-sorted projections and creates breathing phase sorted, static image cubes. Each breathing phase will have a separate image cube. The static image cubes are called static because they represent anatomy in only one breathing phase. Static cubes that represent all of the targeted breathing phases are combined and temporally interpolated (described in Section 3.3) to create a 3D image cube movie from 3D static image cubes.

GREX imaging system 100 keeps the radiation dose to the lowest levels reasonably achievable through statistical image reconstruction. Each acquired image increases the dose of entire imaging process (a clinically undesirable consequence) but provides additional information for image reconstruction (a clinically desirable result). Traditional forms of image reconstruction, based on the Fourier transform or filtered back projection, have the tendency to display image artifacts due to an inability to handle missing information, e.g., missing projection angles, $\beta$. For example, if a projection is taken every 10° instead of 5°, there will be half as much information available for creating a static image cube, but only half the dose was delivered with the former compared to the latter. Statistical iterative image reconstruction addresses the missing information caused by having an incomplete image dataset.

There are numerous statistical image reconstruction algorithms that already exist which GREX imaging system 100 can use to complete the task of image reconstruction (e.g., to construct the static image cubes). However, GREX imaging system 100 improves on traditional statistical image reconstruction algorithms by implementing a unique feedback step and complying with the law of conservation of mass-based boundary condition.

Basic principles of physics can be applied to GREX's statistical image reconstruction because GREX images are biometrically defined by biophysical quantities that are governed by physical law. By biometrically tagging each image and the resulting image cube, as well as by collecting the continuous biometric data stream during the procedure even when not imaging the patient, the breathing dynamics of mass exchange (inhalation and exhalation) and volume change are known (making it possible to solve for the unchanging lung tissue mass that is consistent over the course of the scan). The law of conservation of mass can be applied because static image cubes can be constructed from a moving organ such as lung for the first time. This is due to the prospective prediction/triggering algorithm's speed and accuracy (Section 2.2 and 2.3) which accurately labels and acquires the same chest geometry at different moments in time. Stated differently, the tissue mass in a static image cube should not change (e.g., does not change due to the law of Conservation of Mass) from one static image cube to the next. Based on the ideal gas law, the ratio of room temperature air to air inside lung is 1.11. Given the tidal volume of the image cube from sensor data, and with the 1.11 ratio and the mass/volume air curves for deviations from room temperature, the mass of the inhaled air (in absolute terms and also in relative terms as a ratio between two different breathing phase image cubes) can be determined.

GREX imaging's conservation of mass-based boundary condition is highly useful because, for instance, the presence of air may artificially darken a voxel, thereby adversely affecting the ability of the statistical image registration algorithm to accurately determine object density. By correcting acquired projections for air volume differences and consistently isolating a quantity that should be constant (e.g., lung tissue mass) over the course of the scan, GREX imaging produces more accurate image reconstruction for generating the static image cubes.

Considering two GREX projections taken at different imaging angles but with the same biometrically defined breathing phase, the volume of air in the lung is identical, but the way the air displaces tissue might be different between the two projections and dim the brightness of a nodule in the second projection, which was affected and is erroneous, compared to the first projection. The consequence of this error is that a piece of tissue ("the nodule") that was visible in the first projection is not visible in the second projection, which will ultimately dull the intensity of "the nodule" (or cause it to be mistaken for background) in the resulting image cube. GREX imaging's law of conservation of mass boundary condition is implemented as a feedback step that would check that lung mass was conserved between the aforementioned image cube with the erroneously dim nodule and a different (correct and anatomically representative of "the nodule's" brightness) image cube from a later breathing phase. GREX imaging's feedback step corrects at the level of the erroneous image cube's second projection during reconstruction by updating the expected geometry based on a simulation using the first projection as the gold standard. In this way, GREX statistical image reconstruction would produce more accurate static image cubes.

In addition to pre-existing statistical image reconstruction algorithms, GREX's post-processing software 106 incorporates edge defining filters (discussed in Section 3.2), spatial boundary conditions (discussed in Section 3.2), and smooth transitions between breathing phases (discussed in Section 3.3) into the digital diagnostic x-ray images to improve anatomic imaging.

Section 3.2—Image Filters

A digital diagnostic x-ray image's quality depends on the x-ray unit 108 settings and the image's anatomic study site. Each patient and anatomic site has different electron densities, through which x-rays traverse to generate an image. For example, imaging the femur requires a higher x-ray energy than the x-ray energy required to image the chest because the lung is mostly comprised of air, and the femur is comprised of bone. Given that higher energy x-rays penetrate the body at to a greater extent than lower energy x-rays penetrate the body, the number of x-rays that emerge from the body to reach the flat-panel detector are different for high energy x-rays and low energy x-rays imaging the same anatomic geometry. Too many x-rays emerging from the body results in the flat panel detector's overexposure, in a manner similar to overexposure in optical photography. If the x-ray unit 108 setting is not optimal for the anatomic image study site, the image quality will be greatly reduced. In clinical practice, commercial vendors have devised imaging protocols for their digital diagnostic x-ray units that roughly estimate optimal x-ray unit settings for a selected anatomic site. But these rough estimates of optimal tube settings are not customized to address the potentially significant anatomic variations between anatomic sites within different patients (e.g. the stomach of an overweight man versus the stomach of an average weight man). Indeed, the vendor community's existing imaging protocol settings, as just rough estimates, seldom result in an optimal quality image.

If optimal x-ray unit settings or other imaging parameters are unknown prior to imaging (as currently the case within the medical community), the strategic deployment of digital image filters can improve the image quality of non-optimal x-ray unit settings. An improved image enhances the visibility of anatomic features that are poorly visible to the human eye. For example, in the coronal plane, every rib might not be visible in a digital diagnostic radiographic image. The post-processing software 106 filters the coronal plane images with an edge enhancing filter, like a Laplacian filter, to display the boundary of all ribs on the resulting image even when the rib boundary on the original image is too subtle for the human eye (e.g. the radiologist's eye) to detect. The post-processing software 106 overlays the filtered image with the original image, which highlights the enhanced (e.g., post-filtration) and previously invisible rib edges onto the original image. Image filters that will be made available for the user to apply include the Laplacian filter, Hanning filter, Butterworth filter, Parzen filter, Wiener filter, Metz filter, Ramp filter, non-linear spatial mean filter, and hybrid filters.

In some embodiments, the post-processing software 106 uses the 3D spatial position localizer 300's skin surface measurements to calculate optimal imaging parameters for images taken at each breathing phase. As a patient breathes, the electron density of the body changes as more air is inhaled and the chest circumference increases. Increasing patient diameter, decreasing distance between the patient and the x-ray unit 108, and decreasing distance between the patient and the detector panel 304 produce additional image noise in the resulting x-ray images. The 3D spatial position localizer 300 tracks the patient's skin surface position for each image in relation to the x-ray unit 108 and detector panel 304. This skin surface position tracking provides a unique measurement for digital diagnostic x-ray studies.

The digital diagnostic radiology field currently relies on scaling ion chamber-measured dose index readings to the patient's approximated body-mass index. A radiology technician currently only takes two measurements: the first measurement with a tissue density equivalent solid water cylindrical phantom with a 16 cm diameter, and the second measurement with a 32 cm diameter materially-identical phantom. The x-ray unit 108 has built-in protocols that are vendor-defined and "one size fits all (patients)" for a particular anatomic location. For example, regardless of a patient's chest diameter, the vendor provides only a single protocol with built-in imaging settings for the technologist to select. In other words, a man with a fat chest gets the same imaging settings as a man with a skinny chest.

The 3D spatial position localizer 300 of the GREX imaging system 100 produces a real-time and personalized measurement of a patient's chest diameter. The measurement will inform the technologist in selecting x-ray unit settings that are personalized for the patient. When the patient is breathing, the chest diameter is changing. A changing patient chest diameter prevents the technologist from optimally setting the imaging parameters to match the patient's chest diameter. Moreover, the real-time and personalized measurement of a patient's chest diameter can be used to remove image noise in post-processing procedures, and to simulate an x-ray image taken with optimal imaging parameters.

Figure 23:
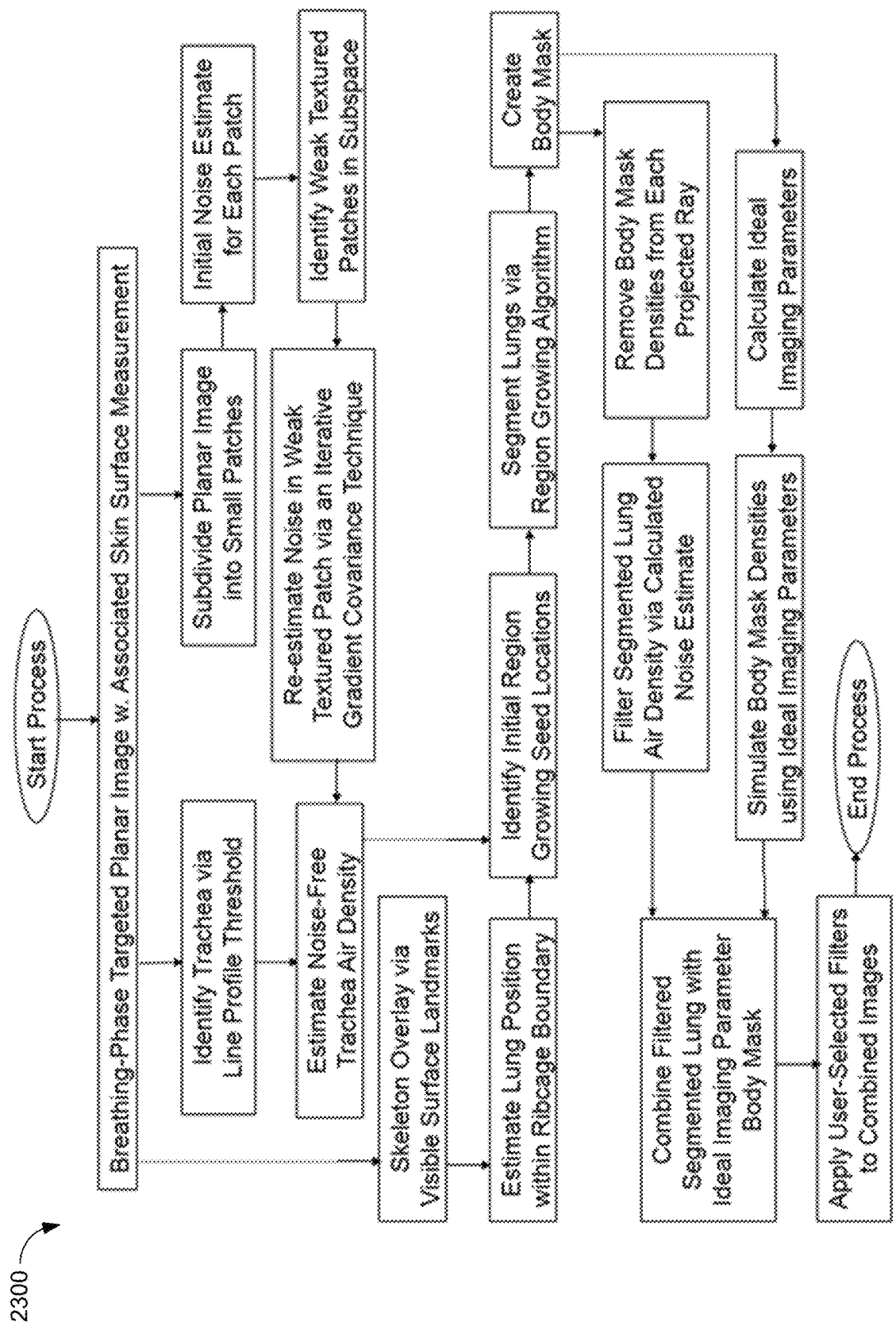
FIG. 23 is a schematic flow chart of an image filtering process according to some embodiments of the present disclosure.

FIG. 23 is a schematic flow chart of an image filtering process 2300 that calculates a noise-free lung image and simulates an image taken with optimal x-ray unit settings according to some embodiments of the present disclosure. After images are acquired as described in Section 2, the trachea is identified using line profiles of segments passing laterally (left to right) through the neck region. The neck is comprised of muscle, bone, and arteries, but the trachea stands out from all other tissues because it contains only air, which has significantly less density than tissues. The line segments will show where air is located and a small region will be identified that contains pixels assigned as air. Image noise in the x-ray image is calculated by subdividing the entire image into smaller patches. Gaussian noise is estimated independently for each patch and those with the least amount of noise are used for texture mapping. The texture mapping technique uses a gradient covariance matrix to estimate an initial texture level in each patch. A patch with the least initial noise level has the noise level re-estimated with an iterative process that continues until the noise estimate for the patch converges with additional iterations of the gradient covariance matrix. A weak textured patch is assumed to be located in air, wherein the air is residing in a location that is away from the patient, e.g., an upper corner of the x-ray image. Estimation of the patch's noise level gives the baseline noise level throughout the image. The baseline noise level that the iterative gradient covariance matrix identified is then subtracted from the entire image to obtain the noise-free air density estimate in the trachea.

The post-processing software 106 overlays a human skeleton model (which is individually scaled for each patient) onto the surface position estimate provided by the 3D spatial position localizer 300 in order to estimate the lung's initial location. The individually scaled patient skeleton is rigidly registered to the x-ray image using visible landmarks on the surface of the skin (e.g., clavicle, rotator cuff, scapula, vertebrae, etc.). After the skeleton has been rigidly registered to the x-ray image, the skeleton provides the position of the rib cage. The rib cage itself provides a boundary condition for the edge of the lungs and for the pixel values close to the trachea's noise-free air density estimate. Both the edge of the lungs (via the rib cage location) and the pixel values close to the trachea's noise-free air density estimate are automatically identified by the region growing algorithm as seed locations (from which the region growing algorithm will initiate and subsequently grow radially outward from). Region growing is a region-based segmentation method. This approach to segmentation first identifies a set of initial seed points within an image and then examines neighboring pixels of the initial seed points and determines whether the neighboring pixels should be added to the region. The process is iterated on, in the same manner as general data clustering algorithms. In other words, region growing algorithms use initial placement of seed pixels to expand outward using a statistical process that annexes "similar" pixels. The region growing algorithm will continue (to annex similar pixels) until the identified pixels are statistically dissimilar from the annexed cluster.

In practice within the GREX imaging system, the region growing algorithm "stops" (e.g., detects pixel dissimilarity) at important anatomic landmark interfaces (such as the lungs, which are bounded by the intense pixels of the rib cage). Pixels that the region growing algorithm does not identify as belonging to lung tissue will be masked (a mask image is defined as an image that enhances structures once subtracted from an original image) to form two separate images. Those two separate resulting images are (i) the segmented lungs and (ii) the remaining body tissues. In order to provide an accurate and noise-free segmented lung volume that gives the radiologist increased diagnostic visibility (e.g., a lung volume that is visually unobscured by non-lung tissue), body mask-related (e.g., non-lung and therefore visually uninformative) tissues are removed from the lung image. For example, the pixels belonging to the intercostal muscles within each simulated imaging ray projection are altogether subtracted from the segmented lung image. In addition to the aforementioned subtraction of the body mask from the lung image to yield improved lung tissue visualization, the body mask can also be used to provide a second check of the 3D spatial position localizer 300's calculated patient surface position. For example, the post-processing software 106 calculates the number of pixels that the region growing algorithm identifies as the body mask, and then calculates the body diameter at various locations along the height of the torso. This body diameter calculation should closely agree with the 3D spatial position localizer 300's estimate of the patient's body diameter. If not, it might indicate that the 3D spatial position localizer 300 needs to be re-calibrated to increase its accuracy.

If a clinical user desires a more accurate view of the body mask (e.g. for clinical or educational reasons), the body mask images are simulated with the optimal x-ray unit settings, thereby removing forms of noise and potential sources of artifacts from the body mask. The body mask and the segmented lungs could then recombine to form artifact- and noise-free x-ray images with global enhancement for clinical applications like structure contouring.

Section 3.3—Biomechanical Modeling

The biomechanical models used in the post-processing software 106 are created from the first principles of physics, namely the law of conservation of mass and the ideal gas law. The goal of the post-processing software 106's biomechanical models is to determine biophysical quantities that enhance a clinician's ability to diagnose disease. Relevant biophysical quantities include, but are not limited to, stress and strain of lung tissue elements.

A mechanical system loaded with a force produces stress. In the context of the lung, an element of a mechanical system is represented by lung tissue. Lung tissue that is visible and distinguishable in medical imaging consists of parenchyma (including alveoli sacs, alveoli walls, bronchial tubes, and blood vessels). Parenchyma is directly responsible for lung function. Suitable tissue elements for biomechanical modeling should be small enough to be homogeneous inside, but statistically stable in response to respiratory stimuli. Typical voxel sizes in lung medical imaging range from 1 $mm^3$ to 3 $mm^3$, which equates to 125 to 375 alveoli. The voxels are deemed to be nearly homogeneous in density and contain enough alveoli to provide a stable response to respiratory stimuli. The alveoli are arranged in hexagonal arrays that inflate due to distending normal stress from each shared alveolar wall. The sum of all distending normal stresses within a lung tissue element provides an estimate of the pressure experienced by the alveoli and caused by respiratory stimuli. The distending stress is counterbalanced by the recoil stress on the alveoli wall, and an equilibrium exists between the two stresses when the airflow through the tissue element is 0. Spatial translation of a lung tissue element's position, in any one direction, due to changing lung tidal volume can be modeled by the tissue element's material response to normal stress on the lung tissue element's corresponding face. In other words, the biomechanical model includes vectorized terms that describe the lung tissue element's response to increasing tidal volume, wherein the vectorized terms relate to normal stress.

Strain is defined as the response of a mechanical system to stress. From the perspective of an element of material (e.g., tissue), stress is a deforming force, and strain is a restoring force. Stress vectors on the lung tissue element's face contains two components: (i) normal stress (related to the lung tissue element's outward or inward directional motion which results in either expansion or contraction, respectively), and (ii) shear stress which is perpendicular to the normal stress and is caused by airflow-induced pressure imbalances. Note that, by definition, the perpendicular component of shear stress does not contribute to lung volume changes. An illustration of the relationship between normal stress/shear stress and tidal volume/airflow, can be found in the "airflow vs tidal volume" plot depicted in FIG. 10. Exhalation is located at the lowest tidal volume magnitude where the airflow is 0 (left-most point on the curve). During inhalation, the airflow is positive and the tidal volume is increasing (upper portion of the curve). When airflow slows, tidal volume reaches its maximum magnitude. As the tidal volume approaches maximum magnitude (right-most point on the curve), the airflow sharply decreases and the lung increasingly begins to expel air. As the lung expels more air, the tidal volume begins to decrease. The tidal volume decreases when the airflow is negative, and continues to decrease until both the tidal volume reaches residual capacity and the airflow is zero (e.g., exhalation). To summarize, a lung tissue element's motion is defined by the tidal volume and airflow respiratory stimuli. A lung tissue element's motion is caused by the normal stress and shear stress acting upon the element. Changes in the lung tissue element's shape (e.g. compression, elongation) are not modeled by stress; rather, an element's shape changes are modeled by strain.

The model creates a new diagnostic perspective within the field of medicine because medical analysis, using the model, is governed by quantitative force analysis. The balance of stress and strain forces at each voxel in the lung fundamentally assesses lung health because the lung's functional behavior (e.g., lung tissue motion) can now be both visualized and analyzed from a clinical perspective.

The first step in building the model is to identify what tissues are part of the lung and what tissues are not part of the lung. To accomplish this task, GREX imaging technology acquires multiple snapshots of the chest geometry in multiple configurations (6 distinct breathing phases). The lung is segmented based on region growing segmentation algorithm using the trachea's air density as an initial starting point for the region growing algorithm. GREX imaging system 100 uses two different deformable image registrations for building the biomechanical model: one acts on lung tissue and the other acts on non-lung tissue (e.g. chest wall, ribs, liver, heart, trachea, esophagus, etc.). The results of a region growing algorithm distinguish between lung tissue and non-lung tissue prior to the deformable image registration step.

The justification for GREX imaging system's using two different deformable registrations, one for lung and the other for non-lung, is that the motion and material properties of lung are different from those of non-lung. If just one deformable image registration is used for the totality of lung and non-lung, the registration would assign a greater weight to the non-lung tissue compared to the lung tissue. This would result in the lung tissue being assigned an unrealistically low weight, and therefore unrealistically limited extent of motion. GREX imaging technology is built to visually elucidate the subtleties of lung motion, including the subtleties of motion at the computationally complex lung surface.

One deformable image registration algorithm that can track tissue movement between images is the optical flow algorithm. FIG. 27 is a schematic flow chart of a multi-resolution 3D optical flow algorithm 2700 according to some embodiments of the present disclosure. Specifically, the 3D multi-resolution optical flow algorithm performs deformable image registration which identifies structures in two different images based on each structure's brightness or contrast or both. To that end, given that the non-lung tissues contain characteristically brighter (e.g., at least 10× denser) anatomical structures (e.g. ribs, pectoral muscles, sternum, etc.) compared to lung tissue, using a single 3D multi-resolution optical flow algorithm on both non-lung and lung regions would result in the less dense lung tissues being artificially non-prioritized within the algorithm. The computational resources of the algorithm would be preferentially allocated to the brighter contrast structures (like the ribs, for instance) that reside in non-lung tissue. An outcome like this, where computational resource allocation preferentially neglects lung tissue dynamics, is anathema to GREX imaging's purpose of visually elucidating the subtleties of lung tissue motion.

Since preferential resource allocation to high contrast structures is inherent to the 3D multi-resolution optical flow algorithm, the task of deformable image registration in the chest is divided into two separate subsidiary tasks (e.g., two internally more homogeneous regions): (i) the image registration of the lung, and (ii) the image registration of the non-lung. In some embodiments, to parse the two separate task regions from the chest as a whole, identification of the lung surface (e.g., the boundary between the lung and non-lung) is required prior to the 3D multi-resolution optical flow deformable image registration. Identification of the lung surface is fundamentally possible using the region growing algorithm, which begins inside the lung in air-filled (e.g., visually dark) regions, grows outward towards the lung surface boundary, and encounters a high pixel contrast at the lung surface boundary. Performing the region growing algorithm is the first step.

The lung is not attached to the chest wall. As a result, the lung's motion is relatively independent from the chest's motion. In other words, instead of a predictable push-pull response at the lung surface boundary, there are other types of tissue dynamics at work. For example, a horizontally adjacent chest voxel moves downward vertically, so the lung voxel moves horizontally into the space where the chest voxel previously resided.

In order to accurately model the complex motion dynamics, GREX imaging system 100 quantifies the shear force that the surfactant layer experiences at the lung surface boundary. Using two separate segmentations for lung and non-lung tissue provides the basis of force estimation. The procedure of force estimation is performed by subtracting the segmented lung pixels (e.g., remove their assigned value) from an x-ray image (performed for each reconstructed breathing phase image). The previously segmented lung will be masked from the original image which provides an image containing all remaining tissues. Each individual image's segmented chest geometry must be registered to each of the chest geometries of the other images so that the position of each lung tissue element is known across all images. The multi-resolution optical flow algorithm performs the image registration by calculating a displacement vector field that shows the displacement of every pixel between two images taken at different breathing phases. Indeed, knowing the displacement vector field allows accurate spatial accounting of all lung tissue elements in the chest geometry. Differences between the segmented lung registration's displacement vector field and the non-lung tissue's displacement vector field provide the magnitude and direction of the shear force that exists between the lung and the chest wall.

Based on observation of over 150 unique patients, the relationship between displacement and tidal volume is linear. The relationship between displacement and airflow is also linear. The multi-resolution optical flow algorithm's output is displacement vectors in a coordinate space for each of the measured tidal volume and airflow magnitudes. When the displacement vectors are calculated for all breathing phases, the result is a closed loop trajectory (as shown in FIG. 10), which serves as observations for the biomechanical model. As describe below in more detail, the biomechanical model parameters—which can include parameters that represent normal stress associated with tidal volume, normal stress associated with airflow, and shear stress associated with airflow—are solved using a QR decomposition for each lung tissue element separately. The parameters are specific to each lung tissue element (e.g., each lung tissue element has a unique solution) and collectively describe the lung tissue element's response to respiratory stimuli. The biomechanical model parameters are vectors that are globally scaled by the measured tidal volume and airflow (e.g., the tidal volume and airflow are scalar values). Relationships between the biomechanical model parameters, such as the angle between two (vectorized) parameters, may aid in diagnosing potential disease incidence in the lung. Based on the lung tissue element's unique biomechanical model vector parameters (e.g., each piece of tissue has different vector parameters), the lung tissue element's displacement is scaled to the chest geometry, wherein the chest geometry is defined by the tidal volume and airflow measurements. The biomechanical model may be calculated for each patient or shared by multiple patients.

In some embodiments, the biomechanical model approximates the motion of lung tissue to be a function of multiple factors, including the lung's tidal volume ($T_v$), airflow ($A_f$), and cardiac phase ($H_c$). These values are global values, e.g., the cardiac phase is the same for all tissue elements in the chest. Global values are treated as scalar numbers and are measured by the hardware discussed in Section 1. Note that the tidal volume, airflow, and cardiac phase are all time varying measurements. The unique stress and strain values for each tissue element is mathematically expressed by the equation below using the vectors $\vec{p}_1$, $\vec{p}_2$, $\vec{p}_3$, and $\vec{p}_4$:

$$\vec{U} - \vec{U}_0 = T_V \vec{p}_1 + A_f(\vec{p}_2 + \vec{p}_3) + H_c \vec{p}_4 \qquad (2)$$

wherein the $\vec{p}_1$ vector describes normal stress caused by tidal volume, $\vec{p}_2$ describes normal stress caused by airflow, $\vec{p}_3$ describes shear stress caused by airflow, and $\vec{p}_4$ describes tissue motion introduced by the perturbing heart motion. Altogether, the displacement ($\vec{U} - \vec{U}_0$) of tissue at any point in a closed loop trajectory is expressed as a summation of the stress, strain, and perturbing heart motion vectors scaled by the tidal volume, airflow, and cardiac phase respectively.

Figure 24:
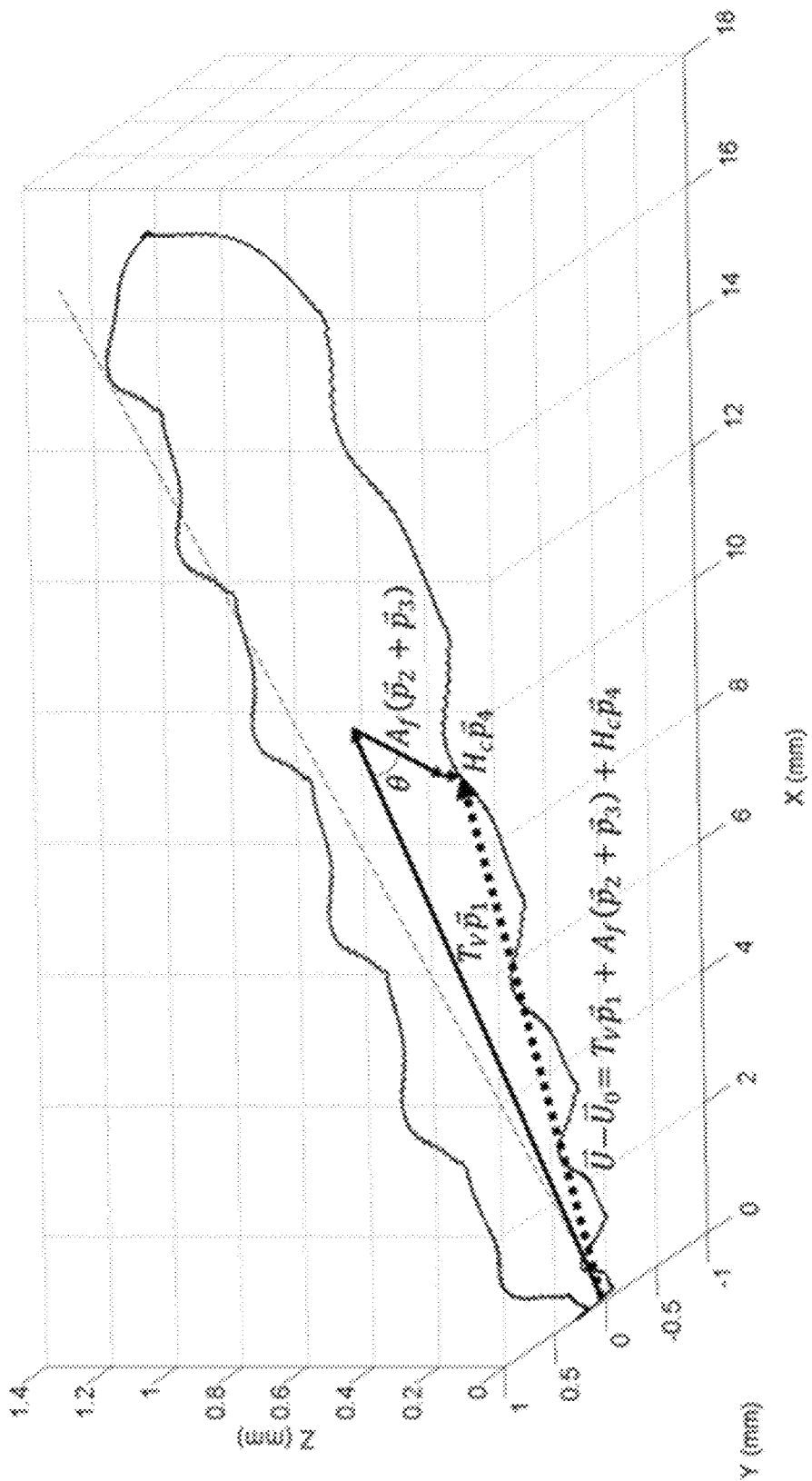
FIG. 24 depicts an exemplary closed-loop lung tissue trajectory of a piece of tissue located in the left lung, close to the heart, caused by the heart's interaction with the lung according to some embodiments of the present disclosure.

FIG. 24 depicts an exemplary closed-loop lung tissue motion trajectory of a piece of tissue located in the left lung, close to the heart, partially caused by the heart's interaction with the lung according to some embodiments of the present disclosure. Note that the wave behavior depicted in FIG. 24 arises from the heart's interaction with the lung. FIG. 24 is a schematic block diagram illustrative of how to determine the position of the piece of lung tissue moving in the closed loop lung tissue motion trajectory based on the aforementioned biomechanical model according to some embodiments of the present disclosure. FIG. 24 shows how the three vectors of the biomechanical model described in the equation above are summed together to calculate the displacement of a single tissue element from the origin to any location on the closed loop trajectory.

A major advantage of using a physiologically-based, biomechanical model to interpolate images between acquired breathing phases is the ability to use quantitative physical quantities to check the accuracy of the biomechanical model's output results. According to the ideal gas law, the ratio of lung volume change to tidal volume is 1.11 at room temperature. In other words, the ratio of room air density to lung air density is 1.11. Accordingly, the volume integral of the divergence of the normal stress vector should also be 1.11 (e.g., $\int_V (\vec{\nabla} \cdot \vec{p}_2)$ dV, where V is the total body volume). The ideal gas law provides a "sanity check", yielding useful quality assurance information on the 3D spatial position localizer 300, breathing phase sensor 110, and each interpolated image.

An example of how the GREX imaging technology's biomechanical modeling enhances diagnosis is an early stage lung tumor that is not visible to a radiologist's eye at the time of image inspection. The tumor is not visible to the radiologist because it is too small for the imaging sensitivity. Even though the tumor is not visible to the radiologist, its presence still affects the balance of forces inside the lung since a tumor's electron density is greater than healthy lung tissue's electron density. The tumor's higher electron density means that the tumor has different material and mechanical properties (e.g., different characteristic stress and strain parameters) that affect both the tumor's motion and the motion of the local area around the tumor (e.g., healthy tissue close to the tumor site). The effect of a tumor on the local healthy lung tissue can be loosely analogized to the effect mass has on the space-time continuum under the general relativity theory: when a massive object is present, the space-time around the object bends so that light behaves differently in the object's vicinity compared to the light's behavior when the mass is absent. The same analogized principle applies in the lung, such that a tumor warps the motion trajectories of adjacent healthy tissues into moving differently compared to a healthy lung's motion trajectories. The biomechanical model's displacement vector map makes changes in lung tissue composition and biomechanical properties readily apparent to medical practitioners: when a tumor is preset, the displacement vector field shows an unnatural level of vector curl and/or other altered properties. GREX imaging technology's post-processing software 106's creation of parameter maps, discussed in Section 3.4, visually displays such previously invisible, diagnostically important information for the end-user. GREX imaging technology's parameter maps are examples of the new diagnostic perspective that the GREX platform brings to medicine.

Figure 25:
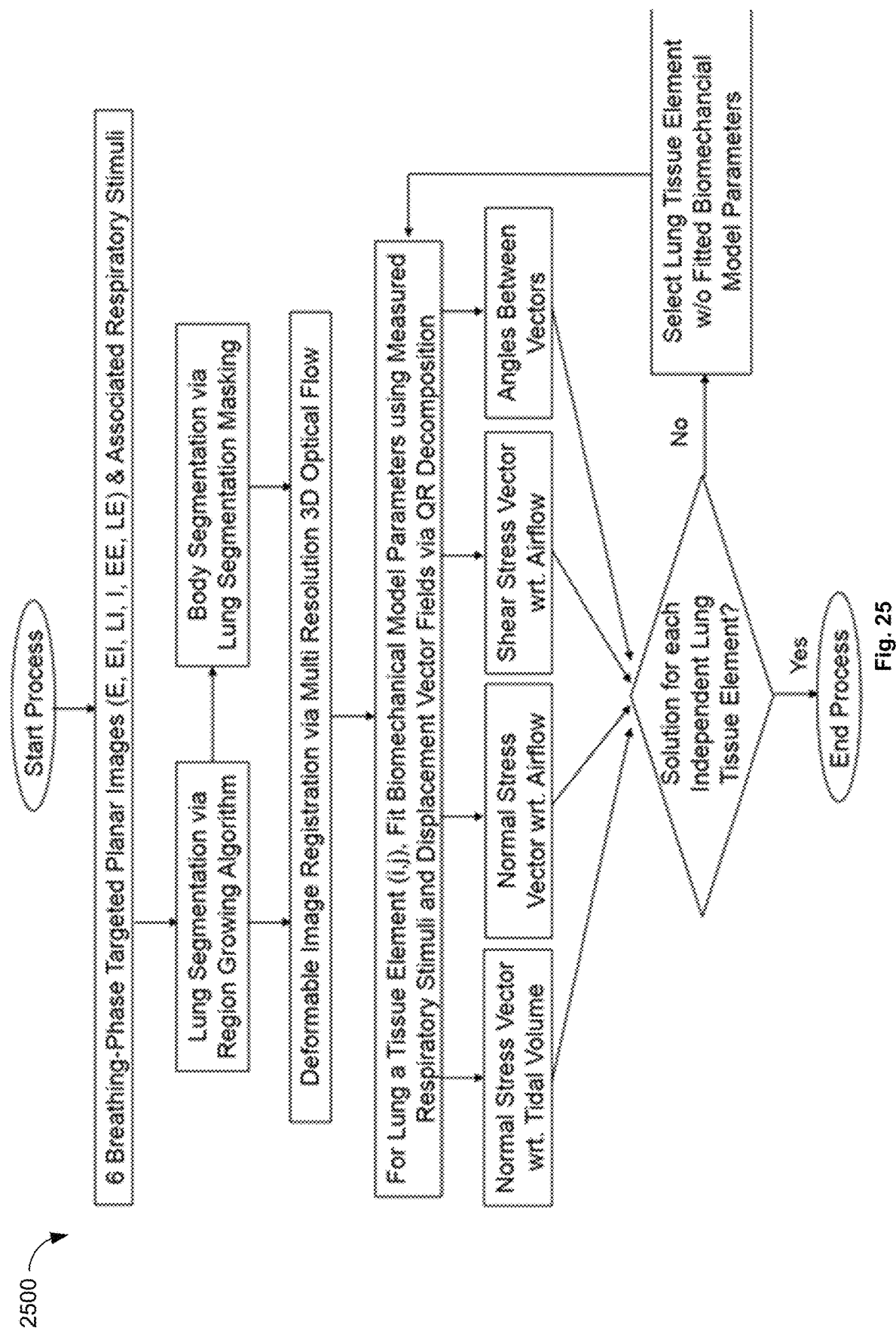
FIG. 25 is a schematic flow chart of operations of components of the biomechanical model according to some embodiments of the present disclosure.

FIG. 25 is a schematic flow chart of operations 2500 of components of the biomechanical model according to some embodiments of the present disclosure.

The biomechanical model's process provides a quantitative means for biometrically interpolating between two images (2D or 3D) acquired at different breathing phases. Equation (2) shows that the solution for the biomechanical model is the displacement between two breathing phases ($\vec{U} - \vec{U}_0$). As noted above, the displacement between two breathing phases ($\vec{U} - \vec{U}_0$) is found by performing deformable image registration to index the two breathing phases to one another, which is typically comprised of the following three steps:

Step 1: Perform region-based segmentation to delineate the structural boundary between the lung and non-lung.

Step 2: Perform intensity-based structure mapping using 3D multi-resolution optical flow to match "same" structure in two separate image cubes.

Step 3: In some embodiments, the initial estimate of the displacement between two breathing phases ($\vec{U} - \vec{U}_0$) is iteratively refined until it is optimized.

Figure 26A:
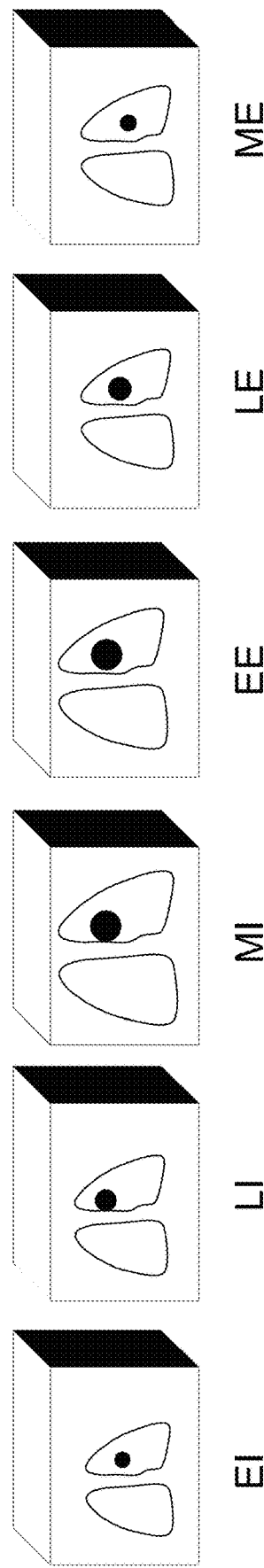
FIG. 26A is a graphic depiction of a lung tissue element's motion trajectory during a breath cycle according to some embodiments of the present disclosure.

FIG. 26A is a graphic depiction of a lung tissue element's motion trajectory during a breath cycle according to some embodiments of the present disclosure. As shown in FIG. 26A, there are 6 images per imaging angle, corresponding to six respective breathing phases of a complete breathing cycle, from left to right, early inhalation (EI), late inhalation (LI), maximum inhalation (MI), early exhalation (EE), late exhalation (LE), and maximum exhalation (ME), as depicted in FIG. 14. According to the finite strain theory, a vector joining the positions of a particle in the un-deformed configuration and the deformed configuration is called the particle's displacement vector. Using a particular voxel in the EI image cube as a reference, the six images illustrate the deformation of the reference voxel from its original position, size and shape during the breathing cycle. When the lung is filled with more and more air, the reference voxel begins to "bubble". In other words, the lung issue corresponding to the reference voxel deforms when the voxel "bubbles". The displacement between two breathing phases ($\vec{U} - \vec{U}_0$) quantifies the extent of voxel bubbling or the deformation of the corresponding lung tissue. Deformable image registration assumes that the reference voxel in the EI image cube moves to its new position in the LI image cube while deforming at the same time due to the inhalation of more air into the lung tissue. As the breathing cycle moves forward, the reference voxel keeps its motion trajectory as depicted by the MI, EE, LE, and ME image cubes, respectively. In other words, for every voxel in the reference image cube, a set of displacement vectors are computed across all the six image cubes.

Figure 26B:
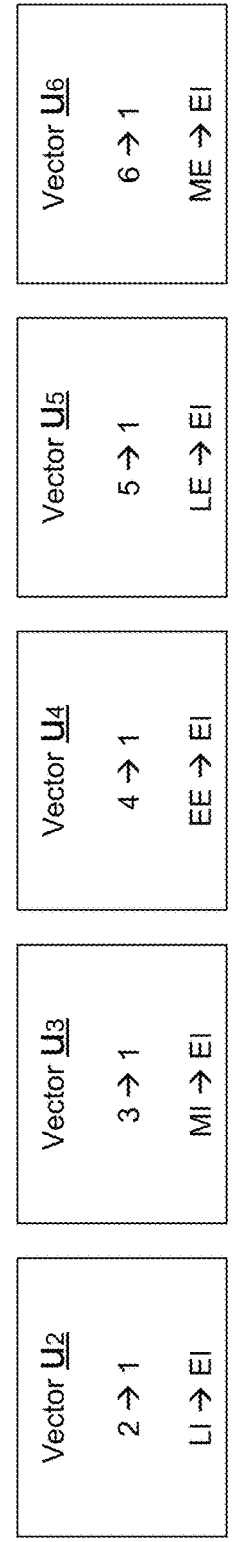
FIG. 26B is a graphic depiction of the displacement vectors between different breathing phases according to some embodiments of the present disclosure.

FIG. 26B illustrates that there are 5 deformable registrations ($2 \to 1$, $3 \to 1$, $4 \to 1$, $5 \to 1$, $6 \to 1$) between the EI image cube and the other five image cubes. These six image cubes represent the patient's chest anatomy at the six corresponding predefined breathing phases. For each voxel, there is a vector ($\vec{U}$) at an image cube corresponding to each of the six breathing phases. Assuming that the vector corresponding to the EI image cube is zero, the six displacement vectors for a given voxel can be expressed as:

[$\vec{U}_1 = 0$, $\vec{U}_2$, $\vec{U}_3$, $\vec{U}_4$, $\vec{U}_5$, $\vec{U}_6$] or denoted as [$\vec{U}_n$], wherein the parameter "n" is a time-dependent parameter corresponding to a respective breathing stage.

Similarly, for a particular breathing stage "n", the biometric data matrix including the lung's tidal volume ($T_v$), airflow ($A_f$), and cardiac phase ($H_c$) can be expressed as:

[$T_{v_n}$, $A_{f_n}$, $H_{c_n}$]$^T$ or denoted as [$B_n$].

For each voxel in the image cube, the biomechanical model for the parameter matrix, [$\vec{P}$] = [$\vec{P}_1$, $\vec{P}_2 + \vec{P}_3$, $\vec{P}_4$], can be solved for using the six displacement vectors ([$\vec{U}_1 = 0$, $\vec{U}_2$, $\vec{U}_3$, $\vec{U}_4$, $\vec{U}_5$, $\vec{U}_6$]) and the corresponding biometric data matrixes ([$T_{v_n}$, $A_{f_n}$, $H_{c_n}$]$^T$) described above. The four vectors describe the voxel's tissue properties, which govern the voxel's displacement vectors and deformations. For each voxel in the reference image cube, there is:

$$[\vec{P}]_{[B_n]} = [\vec{U}_n].$$

As noted above, there are many deformable image registration algorithms capable of performing image registration for GREX imaging, including the 3D multi-resolution optical flow algorithm. The 3D multi-resolution optical flow algorithm calculates smooth (e.g., fluid-like) transitions between images that are taken at different observed tidal volumes. The calculated displacement between two breathing phases ($\vec{U} - \vec{U}_0$) provides observed points in the tissue trajectory shown in FIG. 24. Once the parameters ($\vec{p}_1$, $\vec{p}_2$, $\vec{p}_3$, $\vec{p}_4$) of the biomechanical model are solved for via, e.g., a least-square regression, varying the tidal volume ($T_v$), airflow ($A_f$), and cardiac phase ($H_c$) produces the entire closed loop trajectory. Taking the closed loop trajectories for all tissue elements in the chest gives new image cubes that can be thought of as biometrically interpolated. As a summary, Table 1 shows each component of GREX's biomechanical model and how the component is found.

TABLE 1

Summary of GREX's biomechanical model's parameters.

| Model Component | Description | How it is Found |
|---|---|---|
| $\vec{U}$ | Coordinates of current image relative to the reference image | The static image cubes are deformably registered together via Optical Flow |
| $\vec{U}_0$ | Coordinates of reference image | |
| $T_V$ | Tidal Volume | Found via a breathing phase sensor 110 |
| $A_f$ | Airflow | Found via a breathing phase sensor 110 |
| $H_c$ | Heart phase normalized to end-diastole so that $H_c$ varies between 0 and 1 | Found via heart phase sensor 112 |
| $\vec{p}_1$, $\vec{p}_2$, $\vec{p}_3$, $\vec{p}_4$ | Tissue specific motion parameters | Found via least squares regression |

Figure 28A:
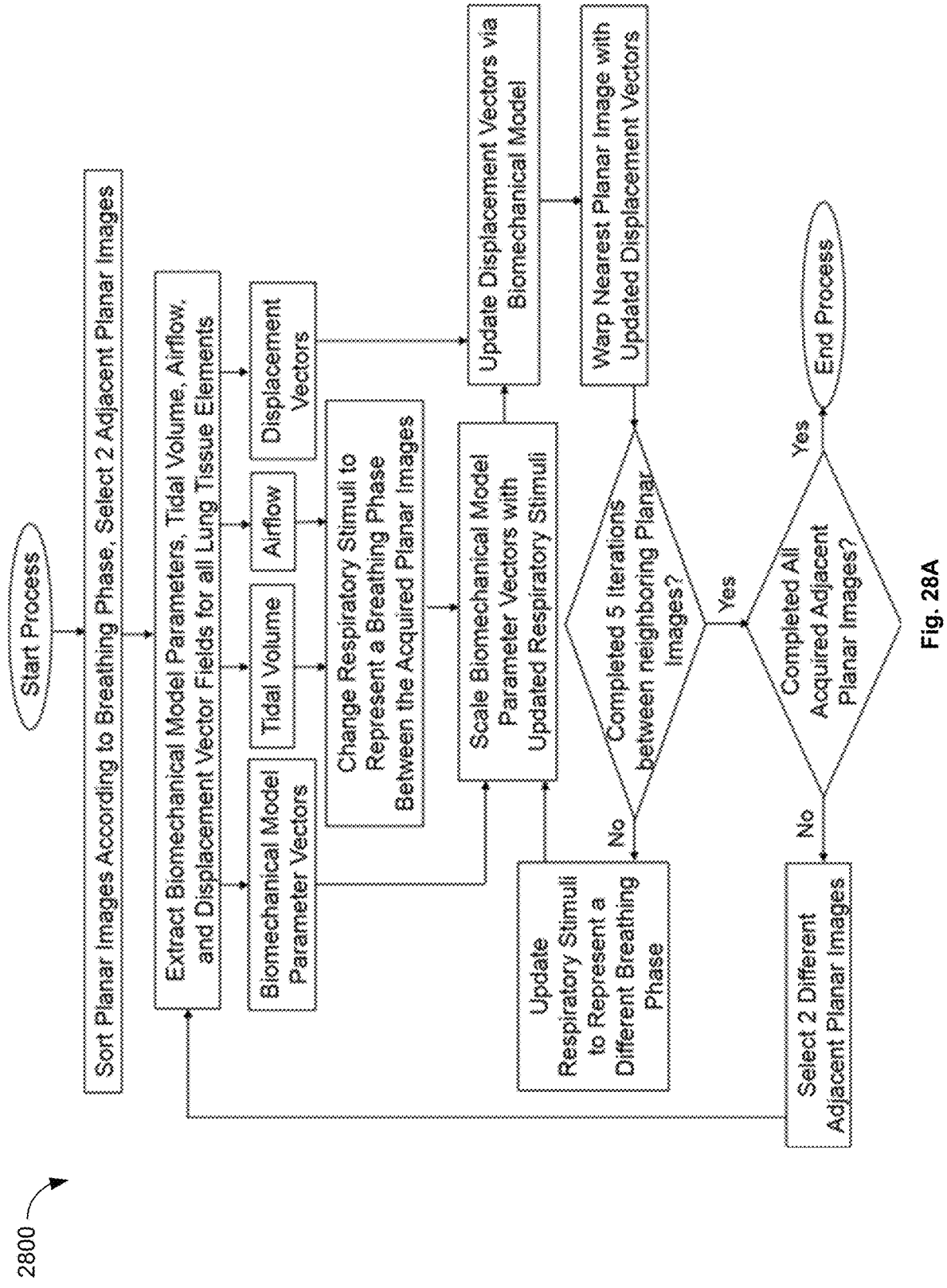
FIG. 28A is a schematic flow chart illustrative of creating a movie via biometric interpolation according to some embodiments of the present disclosure.
Figure 28B:
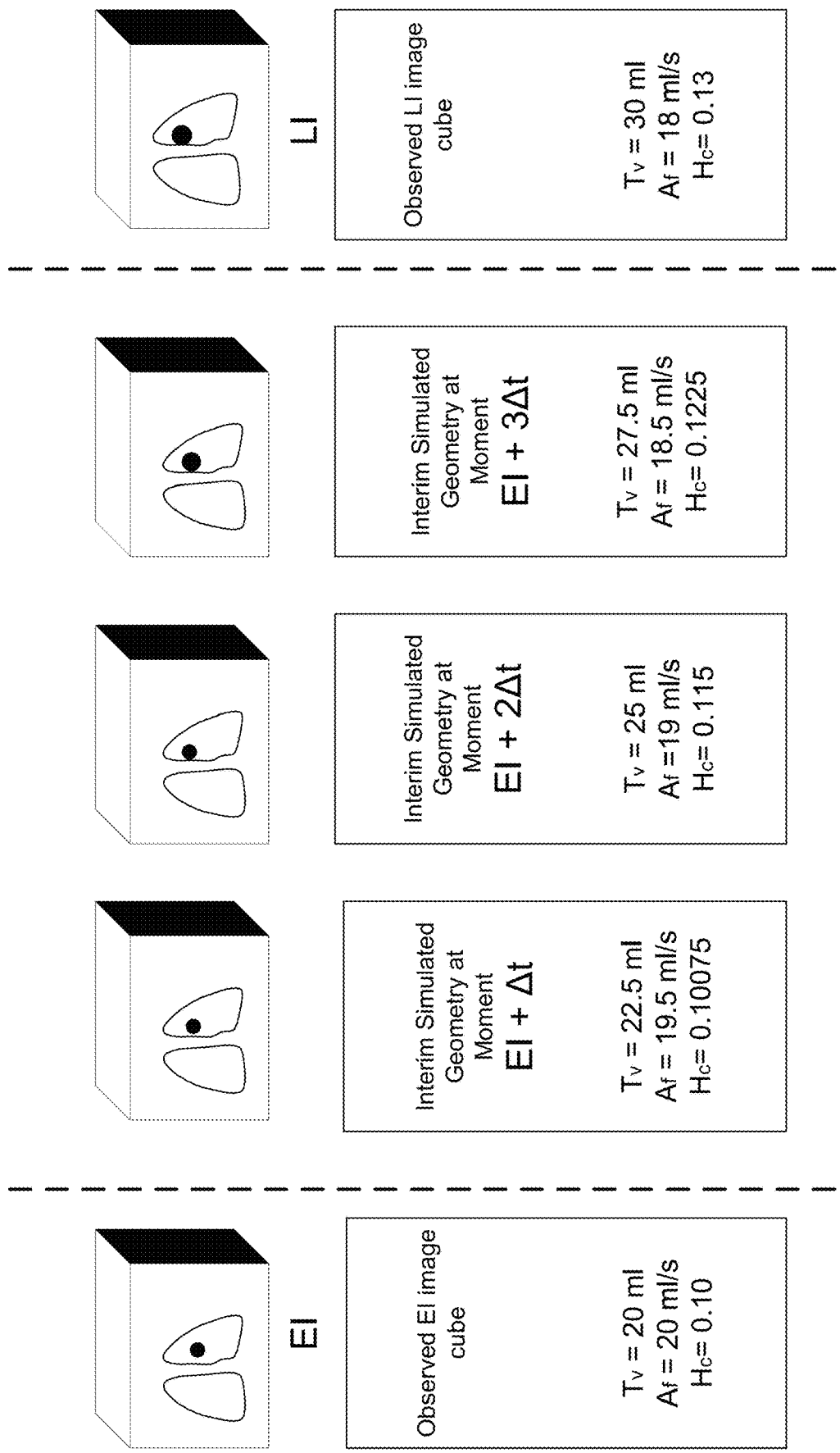
FIG. 28B is a block diagram illustrative of creating interim image cubes using the biometric data matrix according to some embodiments of the present disclosure.

The post-processing software 106's biometric interpolation between acquired image cubes populates all potential breathing phases so that a complete movie of the chest is created. Generally speaking, a movie needs at least 30 simulated images to smoothly transition between frames. FIG. 28A is a schematic flow chart 2800 illustrative of creating a movie via biometric interpolation according to some embodiments of the present disclosure. As shown in FIG. 28B, it is assumed that the biometric data matrix corresponding to the EI image cube is:

$T_v$=20 ml, ($A_f$)=20 ml/s, and $H_c$=0.10.

For each voxel in an interim simulated image cube at a particular moment of the breathing cycle, e.g., EI+$\Delta t$, EI+2$\Delta t$, EI+3$\Delta t$, etc., can be calculated using the biomechanical model for the parameter matrix, [$\vec{p}$], and a corresponding biometric data matrix for the particular moment.

Section 3.4—Parameter Maps

One of the clinical benefits of GREX imaging technology is the unique parameter maps. Using 2D plots, 2D color washes, 3D plots, and 3D vector field maps, the GREX imaging technology presents the end-user with previously unavailable information on the patient's chest health.

FIG. 29 depicts an example of a healthy patient's standard radiograph (left) and an example of a standard radiograph for a patient with a stage 1b left upper lung tumor (right as indicated with the arrow). Both figures show a standard radiograph that is currently used by the radiography field. Although the diseased left lung in the right side of FIG. 29 is an early stage lung tumor, it is not readily visible in the standard radiograph because the standard radiographs are difficult to read and only show anatomic information. In contrast, FIGS. 30A-30B depict the accompanying GREX parameter maps showing indicators of the same two patients' health situation according to some embodiments of the present disclosure. The parameter maps on the right side clearly indicate that the patient has disease in the left upper lung while the standard radiograph is ambiguous. Changing the window level and image contrast eventually shows a poorly ventilated region of the left upper lung. However, if the end-user does not take these steps, the chance of catching this early stage lung cancer tumor is low. In other words, the GREX generated parameter maps can greatly reduce the change of an end-user's risk of a missing disease.

First, let's consider the 2D color maps of $\vec{p}_1$ in FIGS. 30A-30B, which describes normal stress with respect to tidal volume. Based on the definition of $\vec{p}_1$, the end user would expect that the magnitude of $\vec{p}_1$ will be greater near the diaphragm compared to the apex of the lung (e.g., the diaphragm has greater tissue displacement than the apex of the lung when tidal volume is increased). Generally speaking, the magnitude of $\vec{p}_1$ varies smoothly throughout a healthy lung. If the gradient of $\vec{p}_1$ was calculated across the lung, the result would be a smooth function. The examples depicted in FIGS. 30A-30B show that, for both patients, although the $\vec{p}_1$ parameter is similarly distributed, the healthy patient has twice the tissue displacement as the sick patient.

Next consider the 2D color wash of ($\vec{p}_2 + \vec{p}_3$), which represents the sum of normal and shear stress associated with airflow. Generally speaking, higher parameter magnitudes occur close to regions where the bronchial tree brings air into the lung at a faster rate (mid-lung). But in a diseased lung, the presence of a tumor may substantially change the behavior of the lung's elasticity substantially such that the tumor may be visually distinguishable from the functionally healthy lung tissue distribution. In the examples shown in FIG. 30B, the presence of a lung tumor is clearly visible in the left lung because of the significant difference in magnitude. When disease affects a lung region, other lung tissue regions "pick up the slack" by ventilating healthy regions rather than diseased regions. But as shown in the left side figures of FIG. 29, the healthy lung is more elastic than the diseased lung. In other words, airflow resistance was greatly increased in the position where the tumor was located, thereby highlighting the tumor's presence and providing quantitative analysis on the tumor's effect on the patient's ability to properly ventilate during respiration. The ratio between the parameter associated with tidal volume and the parameters associated with airflow dramatically shows that the left upper lung has a considerably different pattern than the healthy patient. Physically, higher percentages are interpreted as the tissue moving in a more circular pattern than the example tissue trajectory shown in FIG. 24. The histograms of the total observed motion component attributed to tidal volume ($T_V \vec{p}_1$) and airflow ($A_f(\vec{p}_2 + \vec{p}_3)$) located below the 2D color washes also displays a clear indicator of disease in the left lung. Healthy lungs have a bimodal distribution of $A_f(\vec{p}_2 + \vec{p}_3)$ but when disease is present in one lung, the overall distribution pattern is different in both lungs. GREX imaging technology may involve Bayes processes to leverage patient interviews (information voluntarily provided by the patient before the exam) with the distribution of the biomechanical model's parameter histograms to better classify disease etiology. In sum, consistent indicators of lung disease (e.g., of a tumor's presence, as shown in FIGS. 30A-30B) across multiple new GREX parameters greatly aids in early detection and disease diagnosis.

Section 3.5—Diagnostic Disease Pointers

Lung cancer, chronic obstructive pulmonary disease (COPD), lower respiratory tract infection, and tuberculosis all have disease pointers that may be visible in existing digital diagnostic x-ray imaging. However, diagnostic disease pointers are not always visible at early disease stages. But as shown in FIGS. 29 and 30, the GREX parameters have the potential of serving as diagnostic disease pointers at early disease stages. If the healthcare team only considered the standard radiographs the lung cancer presence may not have been detected because the lung cancer tumor is not large enough to clearly present in the standard radiograph. GREX imaging uses biometric signals in conjunction with multiple biometrically-targeted radiographs to leverage previously unavailable information on how the lung moves to diagnose disease. The GREX process directly addresses the problem with early lung cancer, that lung cancer tends to have poor specificity in digital diagnostic x-ray images. The existing sensitivity limitations of digital diagnostic x-ray-based diagnoses is addressed through biometrically-informed imaging using the patient's unique and disease indicating breathing information. Clinicians can observe diagnostic insights as early as disease onset and continue monitoring the patient as the disease progresses through lung tissue motion visualization and the parameter maps. Machine learning and finite element analysis techniques will be applied to discover subtle patterns or base-line changes in lung function to assist the ability of an end-user to detect disease at the very onset giving patients higher survival chances and more options for treatment.

Another diagnostic example of where GREX would disrupt the diagnostic community is in classifying lung disease etiology. The presentation of asbestos caused lung disease and cigarette caused lung disease are different in biopsies. Asbestos is a naturally silicate minerals that consists of long, thin fibrous crystals, composed of millions of microscopic fibers. Inhaled asbestos fibers penetrate the alveoli and eventually forms a dense web that compromises the alveolar function which decreases lung function. The dense webs collect cancerous tissues and is named mesothelioma. Standard radiographs can only identify mesothelioma by the plaque buildup, which presents as dense consolidation (fuzziness) in the lung image. GREX may detect the subtle presence of asbestos through the parameter maps before an end-user could visually identify the presence of asbestos. As the web if asbestos is forming, the elasticity of the lung is reduced locally. The small local reduction in elasticity will be visible in the parameter maps (2D color washes, parameter ratios, and histograms). For example, in tissue that has lost elasticity, the tissue's trajectory during breathing will be more circular than elliptical. This means that the ratio between the $\vec{p}_1$ and $(\vec{p}_2+\vec{p}_3)$ magnitudes would be higher than healthy tissue. Consulting the color map would clearly show a region of the lung that is displaying a pattern indicative of disease.

Inhaled particles (non-fiber) would display completely differently than the fibrous asbestos particles. Inhaled particles deposit within the lungs, reducing lung function by "clogging" airways, forming scar tissue, and forming tumors but not webs. GREX will show the beginning of particulate deposition by detecting minute local changes in lung motion dynamics that are inconsistent with healthy characteristics. Cigarettes contain tar and radon, which adhere to the alveoli and drastically changes lung function. GREX can track the reducing lung function and give end-users a unique tool to better demonstrate to a patient how destructive the smoking habit is. COPD is another disease that can be elucidated with parameter maps more effectively than the current clinical methods. COPD is currently detected with spirometry testing and standard radiography. Neither of these methods are particularly sensitive and do not detect COPD at the earliest onset. Detecting disease at the earliest possible time can give patients more opportunity to take advantage of preventative medicine and change bad habits before the it is too late.

Section 3.6—Movie Presentation

The point of the movie presentation graphic user interface (GUI) is to provide a clean and intuitive canvas for displaying the planar movie and 3D movie results. All functions like rotate view, pause movie, and ruler are placed into bins that are represented with tabs across the top of the screen. Selecting a function changes the tooltip to show the user what function is in use. The GUI is designed to be light weight so that the GUI will function even with older computer systems. Finally, the movie presentation GUI will work in conjunction with the annotation/contouring, possible disease pointers, and cloud computing platform.

Medical personnel end-users prefer to directly highlight and place notes on medical images rather than attaching additional documents to the images. Medical end-users clamor for the ability to include image annotation ("attention-grabbing" arrows and treatment notes) and anatomic contouring (drawing a virtual line around an anatomic structure) to imaging studies. Medical end-users are often members of large, multi-disciplinary care teams that collaboratively treat a patient. The following example describes the current workflow and technological capabilities of a clinical care team:

Once an imaging study is performed on a lung cancer patient, the image is read by a radiologist, prescribed radiation treatment orders by a radiation oncologist, and used as a basis for surgical intervention by an operating surgeon. Specifically, the radiologist draws a contour around the tumor site and passes the contoured image to a radiation oncologist.

The radiation oncologist then writes instructions for the radiation treatment and/or tumor resection surgery based on the image.

Using the radiology contour and the radiation oncology tumor resection instructions, the surgeon resects the tumor.

The post-processing software 106 provides tools for end-users to annotate and contour directly on the moving images, which streamlines healthcare workflow. This user-friendly capability enhances healthcare workflow and reduces the probability of medical mistakes. The interactive nature of our user interface means that treatment instructions and/or medical concerns are now plainly visible to all users, and the relevant clinical notes are displayed correctly in the corresponding anatomical region of interest.

Figure 31A:
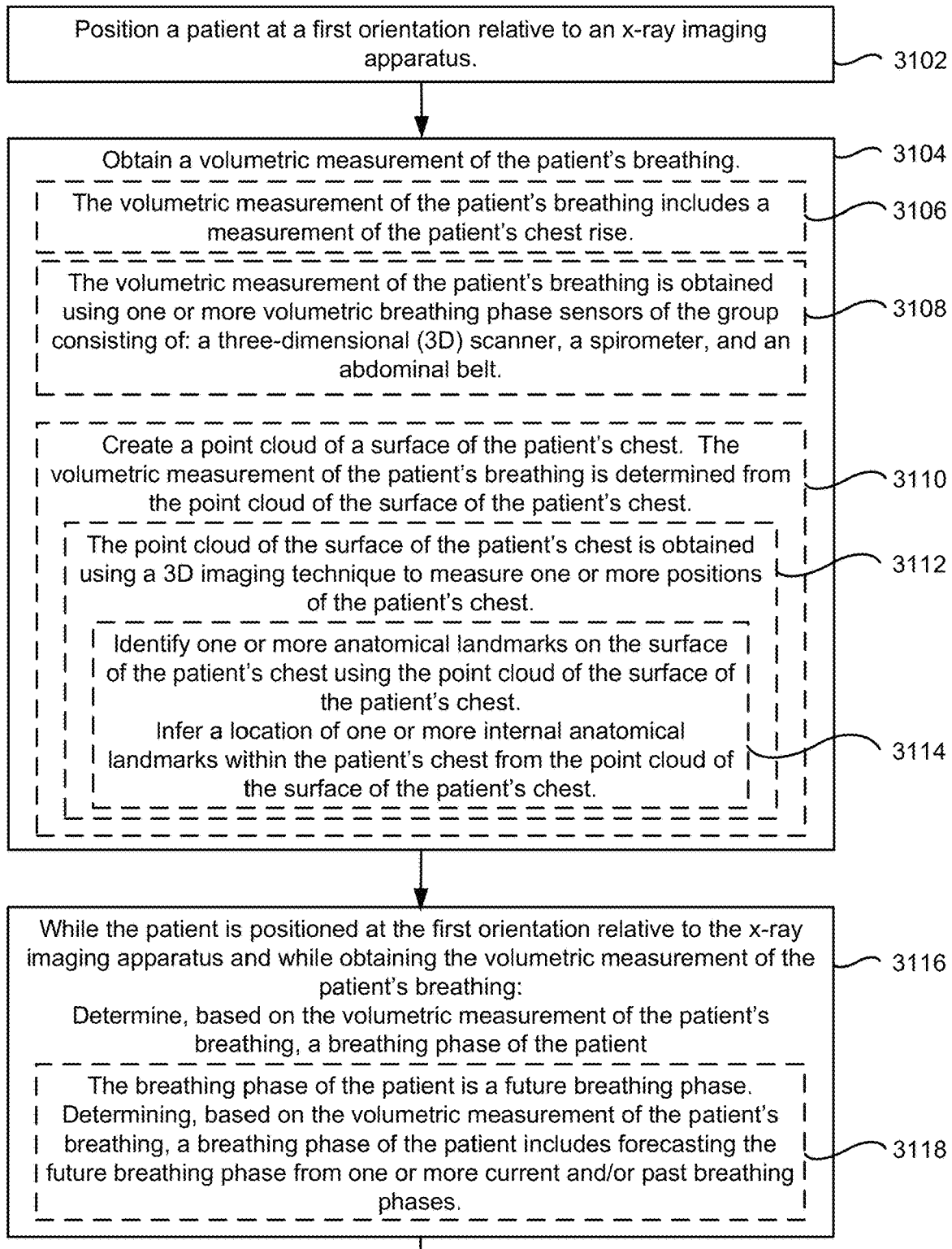
FIGS. 31A-31B are flow diagrams for a method of imaging a patient's lung according to some embodiments of the present disclosure.
Figure 31B:
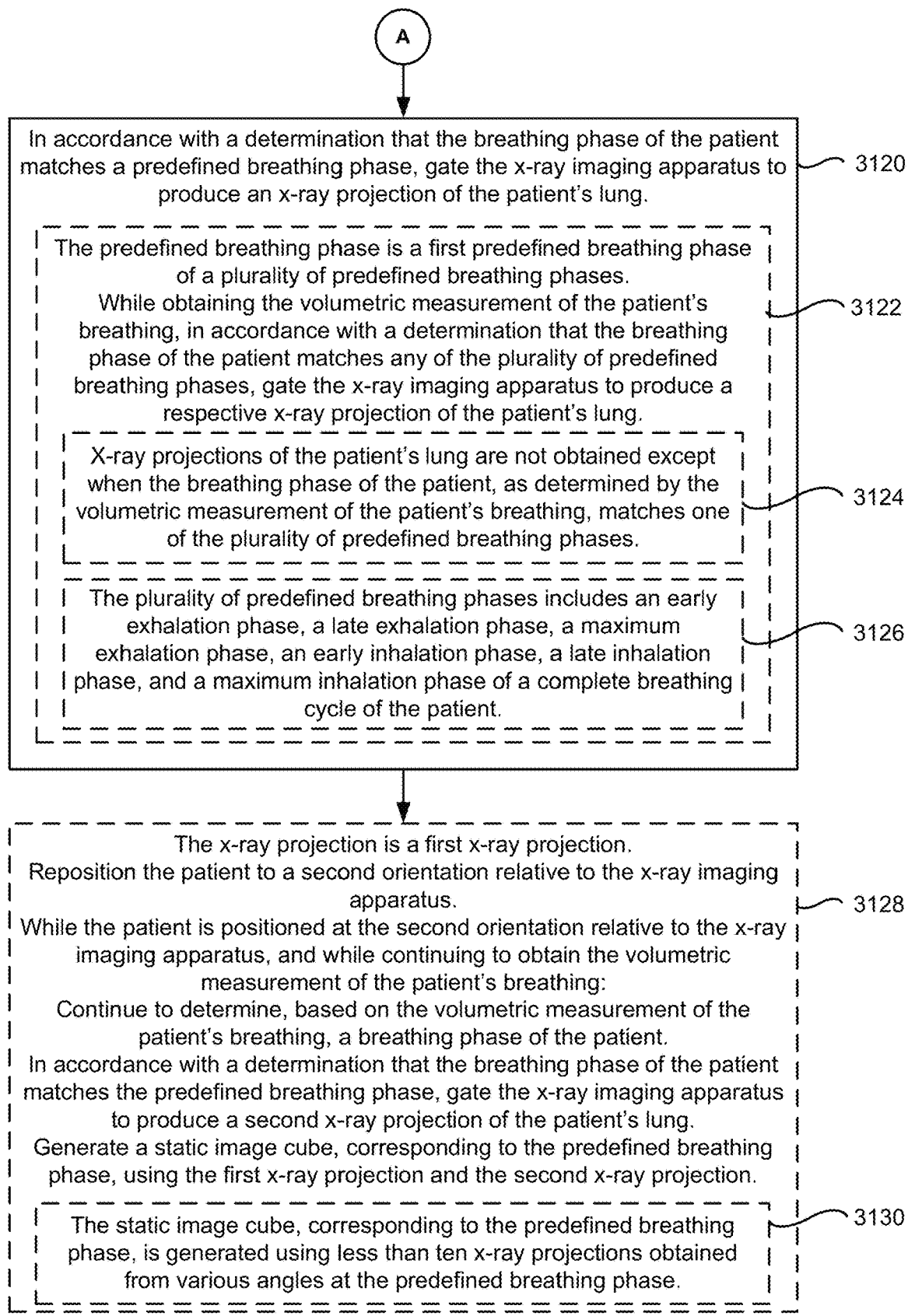

FIGS. 31A-31B are flow charts illustrating a method 3100 of imaging a patient's lung. In some embodiments, any or all of the operations described below can be performed without human intervention (e.g., without intervention by a technician). In some embodiments, method 3100 is performed by or using any of the apparatuses described herein (e.g., the GREX imaging system 100 shown in FIG. 1). Some operations of method 3100 are performed by a computer system that includes one or more processors and memory storing instructions which, when executed by the one or more processors, cause the one or more processors to perform the operations of method 3100. Some operations in method 3100 are, optionally, combined and/or the order of some operations is, optionally, changed.

The method includes positioning (3102) the patient at a first orientation relative to an x-ray imaging apparatus (e.g., GREX imaging system, FIG. 1). In some embodiments, method 3100 is performed at a legacy medical imaging system that is modified to perform certain operations described below. In some embodiments, positioning the patient at the first orientation includes moving (e.g., rotating) the patient to the first orientation (e.g., as discussed with reference to FIG. 35), while the x-ray imaging system (e.g., the x-ray unit and detector panel) remain at a fixed position. For example, in some embodiments, the patient is seated in or standing on a patient positioning fixture (PPF), such as PFF 3501 described with reference to FIG. 35. In some embodiments, positioning the patient at the first orientation relative to the x-ray imaging apparatus includes rotating the patient positioning fixture. For example, in some embodiments, at the beginning of method 3100, the patient positioning fixture is rotated such that the sagittal plane of the patient is positioned at a predefined angle with respect to an optical axis of the x-ray imaging apparatus (e.g., an axis along which the x-ray imaging apparatus transmits x-rays). In some embodiments, the predefined angle is selected from the group consisting of −45 degrees, −22.5 degrees, 0 degrees, 22.5 degrees, and 45 degrees.

In some embodiments, positioning the patient at the first orientation includes moving (e.g., rotating) the x-ray imaging system, while the patient remains at a fixed position (e.g., as discussed with reference to FIG. 17).

In some embodiments, while the patient is positioned at the first orientation relative to the x-ray imaging apparatus, the patient positioning fixture maintains the patient in a fixed position (e.g., stabilizes the position of the patient) such that three-dimensional images of the patient's lung can be reconstructed (e.g., as described throughout this disclosure) based on a "stationary object" assumption.

The method includes obtaining (3104) a volumetric measurement of a patient's breathing (e.g., as the patient is breathing normally; the patient need not hold his or her breath). In some embodiments, the volumetric measurement of the patient's breathing is a measurement (e.g., a direct measurement) of the patient's lung volume (e.g., instantaneous lung volume) or a derivative of the patient's lung volume (e.g., a flow-rate). In some embodiments, as explained in greater detail below, the volumetric measurement of the patient's breathing is a measurement that can be converted to the patient's tidal volume (e.g., by measuring chest rise and fall). The term tidal volume, as used herein, means a difference between a current lung volume and a predefined baseline (e.g., a volume during maximum exhalation of a normal breath without extra effort applied, a volume during maximum inhalation of a normal breath without extra effort applied, or any other suitable fiducial volume).

In some embodiments, the volumetric measurement of the patient's breathing is a geometrical (spatial or positional) measurement of the patient's breathing.

In some embodiments, the volumetric measurement of the patient's breathing includes (3106) a measurement of the patient's chest rise (and/or chest fall). In some embodiments, the volumetric measurement of the patient's breathing is obtained using (3108) one or more volumetric breathing phase sensors (e.g., breathing phase sensor 110, FIG. 1) of the group consisting of: a three-dimensional (3D) scanner, a spirometer, and an abdominal belt. In some embodiments, the method further includes creating (3110) a point cloud of a surface of the patient's chest. The volumetric measurement of the patient's breathing is determined from the point cloud of the surface of the patient's chest.

In some embodiments, the 3D point cloud is used to determine the volumetric measurement of the patient's breathing without generating a mesh reconstruction of the patient's chest (e.g., the raw output of the 3D point cloud is used to generate the volumetric measurement of the patient's breathing without first generating a mesh). In some embodiments, the point cloud of the surface of the patient's chest is obtained using (3112) a 3D imaging technique to measure one or more positions of the patient's chest. For example, the 3D imaging technique comprises a laser scanning technique such as light detection and ranging (LIDAR). Such laser scanning techniques are beneficial because some lasers can accurately measure positions of the patient's chest even while the patient is wearing a modesty garment (e.g., the patient dons a LIDAR-transparent garment while undergoing method 3100).

In some embodiments, the method 3100 further includes identifying (3114) one or more anatomical landmarks on the surface of the patient's chest (e.g., externally-visible landmarks, such as a clavicle, trachea, sternal notch, sternum, xiphoid process, spine, or humorous) using the point cloud of the surface of the patient's chest. The method further includes inferring a location of one or more internal anatomical landmarks within the patient's chest from the point cloud of the surface of the patient's chest (e.g., a location of the patient's lung). In some embodiments, the method includes generating a reconstruction of the patient (e.g., a generating a computer model for the patient, also referred to as a "virtual patient"). In some embodiments, generating the reconstruction of the patient includes generating a reconstruction of the internal anatomy of the patient. In some embodiments, the reconstruction of the internal anatomy of the patient includes a computer model (e.g., a 3D model) of tissue densities. In some embodiments, the reconstruction includes or is used to determine absorption cross-sections (e.g., x-ray absorption cross-sections) at a plurality of locations within the body. In some embodiments, the reconstruction of the patient is used to determine an x-ray dose to be delivered (e.g., for each image) by the x-ray imaging apparatus.

The method includes, while the patient is positioned at the first orientation relative to the x-ray imaging apparatus, and while obtaining the volumetric measurement of the patient's breathing, determining (3116), based on the volumetric measurement of the patient's breathing, a breathing phase of the patient (e.g., in real-time, as the patient is breathing normally). In some embodiments, the breathing phase of the patient is defined by the volume of the lung. Thus, in some embodiments, determining a breathing phase of the lung includes determining a volume of the lung.

In some embodiments, operations 3102 et seq. are performed as part of an imaging period of method 3100. Method 3100 further includes, prior to the imaging period, undergoing a training period during which information about the patient's normal breathing is obtained. For example, during the training period, volumetric measurements of the patient's breathing are obtained at regular intervals over a plurality of cycles of the patient's breathing (e.g., 15, 20, 50 cycles of the patient's breathing, each corresponding to one breath). The volumetric measurements from the training period are then used to associate specific volumetric measurements with specific breathing phases. For example, a volumetric measurement corresponding to a tidal volume of 400 ml may be associated with maximum inhalation, a volumetric measurement corresponding to a tidal volume of 0 ml may be associated with maximum exhalation, and so on. In addition, statistics about the patient's breathing (e.g., a histogram) can be obtained during the training period, and used to verify that breaths taken during imaging are "normal" breaths (e.g., not overly deep breaths or otherwise anomalous breaths).

During the imaging period, in some embodiments, the breathing phase of the patient that is determined is (3118) a future (e.g., predicted) breathing phase. That is, in some embodiments, determining, based on the volumetric measurement of the patient's breathing, the breathing phase of the patient includes forecasting the future breathing phase from one or more current and/or past breathing phases. For example, the forecasting is based on a time-series of breathing phases. In some embodiments, forecasting the future breathing phase from the one or more current and/or past breathing phases includes generating an autoregressive integrated moving average (ARIMA) model. In some embodiments, the forecasting uses data from the training period.

The method includes, in accordance with a determination that the breathing phase of the patient matches a predefined breathing phase (e.g., that the volume of the lung matches a predefined lung volume), gating (3120) the x-ray imaging apparatus to produce an x-ray projection (sometimes called a projection image) of the patient's lung. In some embodiments, an x-ray projection is an image taken at a particular angle (e.g., determined by the orientation of the patient with respect to the x-ray imaging apparatus). In some embodiments, an x-ray projection is obtained using a single x-ray exposure. In some embodiments, the method includes, in accordance with a determination that the breathing phase of the patient does not match a predefined breathing phase, forgoing gating the x-ray imaging apparatus (e.g., forgoing exposing the patient to x-ray radiation).

In some embodiments, the method includes determining, from the volumetric measurement of the patient's breathing, whether a current breath is an irregular breath. The method further includes, in accordance with a determination that the current breath is an irregular breath, forgoing gating (e.g., obtaining) the x-ray imaging apparatus (e.g., continuing to wait for a suitable breath at which to obtain the x-ray projection for the breathing phase).

In some embodiments, the predefined breathing phase is (3122) a first predefined breathing phase of a plurality of predefined breathing phases. In some embodiments, the method further includes, while obtaining the volumetric measurement of the patient's breathing, in accordance with a determination that the breathing phase of the patient matches any of the plurality of predefined breathing phases, gating the x-ray imaging apparatus to produce a respective x-ray projection of the patient's lung. In some embodiments, x-ray projections (e.g., x-ray measurements) of the patient's lung are not obtained (3124) except when the breathing phase of the patient, as determined by the volumetric measurement of the patient's breathing, matches one of the plurality of predefined breathing phases, thus lowering the total amount of x-ray exposure of the patient.

In some embodiments, the plurality of predefined breathing phases includes (3126) an early exhalation phase, a late exhalation phase, a maximum exhalation phase, an early inhalation phase, a late inhalation phase, and a maximum inhalation phase of a complete breathing cycle of the patient (e.g., as shown and described with reference to FIG. 14). In some embodiments, an x-ray projection is obtained for each of the plurality of predefined breathing phases while the patient is positioned at the first orientation relative to the x-ray imaging apparatus.

In some embodiments, the x-ray projection is (3128) a first x-ray projection and the method further includes repositioning the patient to a second orientation relative to the x-ray imaging apparatus (e.g., by rotating the patient or rotating the x-ray imaging system). In some embodiments, the method includes, while the patient is positioned at the second orientation relative to the x-ray imaging apparatus, and while continuing to obtain the volumetric measurement of the patient's breathing, continuing to determine, based on the volumetric measurement of the patient's breathing, a breathing phase of the patient. In some embodiments, the method includes, in accordance with a determination that the breathing phase of the patient matches the predefined breathing phase, gating the x-ray imaging apparatus to produce a second x-ray projection of the patient's lung.

In some embodiments, the method further includes generating a static image cube, corresponding to the predefined breathing phase, using the first x-ray projection and the second x-ray projection (e.g., as described with reference to FIG. 21). In some embodiments, a static image cube is a three-dimensional reconstruction of a volume of the patient's lung. In some embodiments, an x-ray projection is obtained for each of the plurality of predefined breathing phases while the patient is positioned at each of a plurality of orientations (including the first orientation and the second orientation) relative to the x-ray imaging apparatus. In some embodiments, the plurality of orientations includes at least 5 orientations (e.g., −45 degrees, −22.5 degrees, 0 degrees, −22.5 degrees, and 45 degrees). In some embodiments, the plurality of orientations includes more than 5 orientations (e.g., 6, 7, 8, or more orientations). In some embodiments, x-ray projections are not obtained except for each of the plurality of predefined breathing phases while the patient is positioned at each of a plurality of orientations (including the first orientation and the second orientation) relative to the x-ray imaging apparatus. Thus, when x-ray projections are obtained at five orientations and for six different breathing phases, a total of thirty x-ray projections are obtained (e.g., the x-ray imaging apparatus is gated, as described above, to obtain only these images).

As described elsewhere in this document, these thirty x-ray projections can be used to reconstruct a biomechanical model of how the lung moves in 3D. In some embodiments, the static image cube (e.g., as described with reference to FIG. 21), corresponding to the predefined breathing phase, is generated using (3130) less than ten x-ray projections obtained from various angles at the predefined breathing phase.

One of skill in the art will recognize that method 3100 can be applied to other types of movement besides lung motion due to breathing. For example, in some embodiments, a method includes positioning a patient at a first orientation relative to an x-ray imaging apparatus. The method further includes obtaining a 3D measurements of a portion of the patient's body (e.g., a 3D measurement of a location of the portion of the patient's body). The method further includes, while the patient is positioned at the first orientation relative to the x-ray imaging apparatus, and while obtaining the 3D measurements of the portion of the patient's body: determining, based on the 3D measurements of the portion of the patient's body, that triggering criteria are met for triggering exposure to radiation by the x-ray imaging apparatus; and in accordance with a determination that the triggering criteria are met, gating the x-ray imaging apparatus to produce an x-ray image of the patient. In some embodiments, the x-ray image is an image of the portion of the patient's body (e.g., the patient's leg, abdomen, skull, etc.). In some embodiments, the triggering criteria include a criterion that is met when the 3D measurement of the portion of the patient's body indicates that the portion of the patient's body is at a predefined location (e.g., with respect to the imaging apparatus). In some embodiments, the method includes, in accordance with a determination that triggering criteria are not met, forgoing gating the x-ray imaging apparatus (e.g., forgoing exposing the patient to x-ray radiation). Furthermore, in some embodiments, method 3100 is applicable to other types of imaging that are not strictly based on x-rays, for example positron emission tomography (PET) imaging or MM imaging.

In addition, it should be understood that method 3100 can be applied to radiation therapy as well as radiation imaging. For example, in some embodiments, a method includes positioning a patient at a first orientation relative to a radiation therapy source. The method further includes obtaining a 3D measurements of a portion of the patient's body (e.g., a 3D measurement of a location of the portion of the patient's body). The method further includes, while the patient is positioned at the first orientation relative to the radiation therapy source, and while obtaining the 3D measurements of the portion of the patient's body: determining, based on the 3D measurements of the portion of the patient's body, that triggering criteria are met for triggering exposure to radiation by the radiation therapy source; and in accordance with a determination that the triggering criteria are met, gating the radiation therapy source to expose the patient to radiation (e.g., expose the portion of the patient's body to radiation). In some embodiments, the triggering criteria include a criterion that is met when the 3D measurement of the portion of the patient's body indicates that the portion of the patient's body is at a predefined location (e.g., with respect to the imaging apparatus). In some embodiments, the method includes, in accordance with a determination that triggering criteria are not met, forgoing exposing the patient to radiation.

It should be understood that the particular order in which the operations in FIGS. 31A-31B have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein are also applicable in an analogous manner to method 3100 described above with respect to FIGS. 31A-31B. Such process are described, for example, with reference to FIG. 2, FIG. 6, FIG. 8, FIG. 11, FIG. 13, FIG. 15, FIG. 21, FIG. 23, FIG. 25, FIG. 27, FIGS. 28A-28B, FIGS. 32A-32B, FIGS. 33A-33C, and FIGS. 34A-34C. For brevity, these details are not repeated here.

Figure 32A:
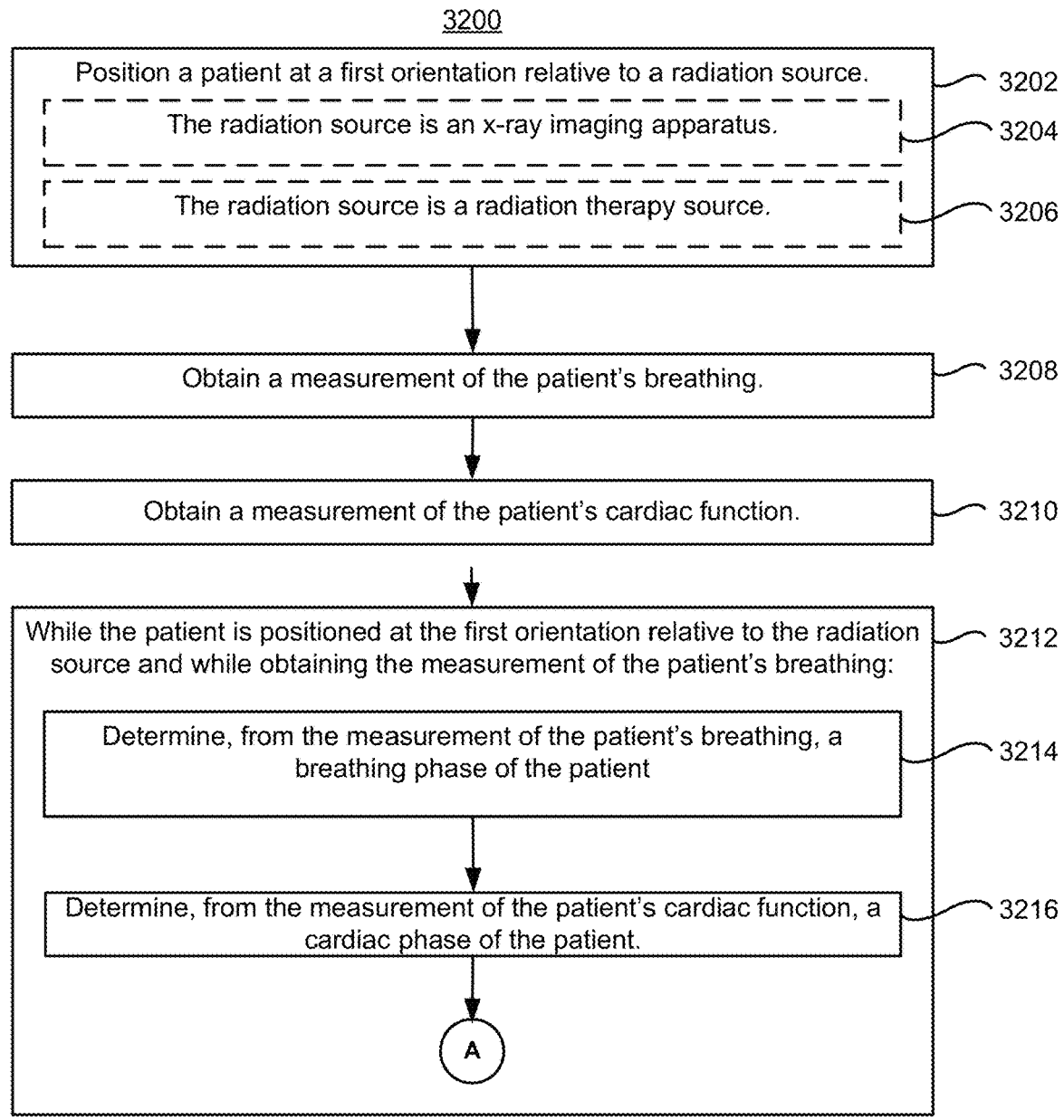

FIGS. 32A-32B are flow charts illustrating a method 3200 for gating a radiation source at coincidence of a patient's breathing phase and cardiac phase. In some embodiments, any or all of the operations described below can be performed without human intervention (e.g., without intervention by a technician). In some embodiments, method 3200 is performed by or using any of the apparatuses described herein (e.g., the GREX imaging system 100 shown in FIG. 1). Some operations of method 3200 are performed by a computer system that includes one or more processors and memory storing instructions which, when executed by the one or more processors, cause the one or more processors to perform the operations of method 3200. Some operations in method 3200 are, optionally, combined and/or the order of some operations is, optionally, changed.

Figure 35:
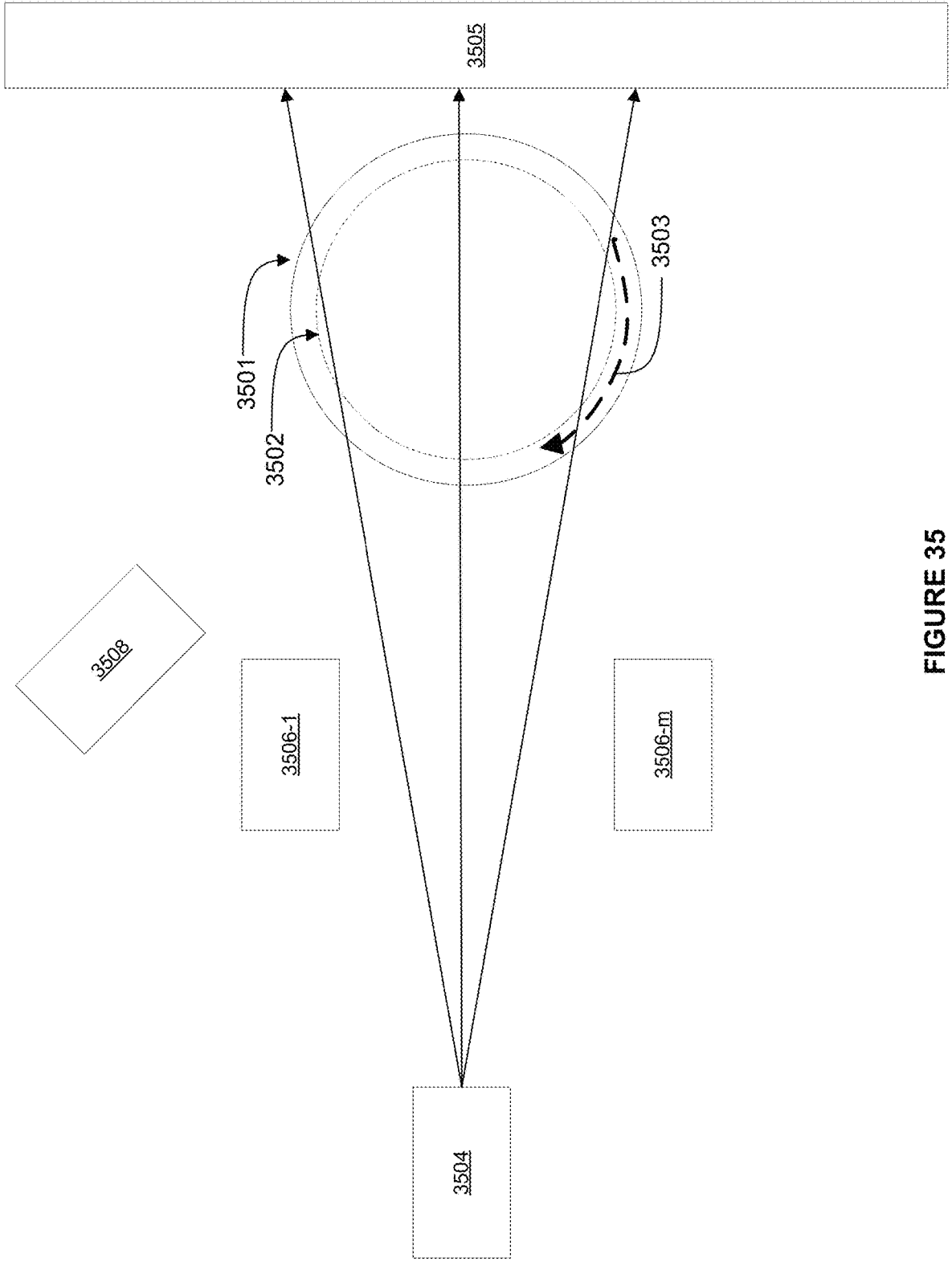
FIG. 35 depicts an exemplary patient positioning fixture (PPF) (e.g., a rotatable chair) for supporting a patient in accordance with some embodiments.

The method includes positioning (3202) the patient at a first orientation relative to a radiation source. In some embodiments, the radiation source is (3204) an x-ray imaging apparatus. In some embodiments, the radiation source is (3206) a radiation therapy source. For example, as shown in FIG. 3 and FIG. 35, the patient (e.g., patient 3502) is positioned in a first position relative to radiation source 3504 (e.g., an x-ray unit 108). In some embodiments, as described with reference to operation 3102 (FIG. 31A), positioning the patient includes moving (e.g., rotating) the patient, whereas in some embodiments positioning the patient includes moving (e.g., rotating) the x-ray apparatus (e.g., the x-ray source and detector).

The method includes obtaining (3208) a measurement of the patient's breathing (e.g., using a breathing phase sensor). In some embodiments, the measurement of the patient's breathing is a volumetric measurement of the patient's breathing, described above with reference to operation 3104 (FIG. 31A). In some embodiments, the measurement of the patient's breathing is a non-volumetric measurement of the patient's breathing (e.g., a timing-based measurement of the patient's breathing).

The method includes obtaining (3210) a measurement of the patient's cardiac function. In some embodiments, one or more sensors are used (3304) for measuring the patient's cardiac function. In some embodiments, an electrocardiogram (ECG) is used for measuring the patient's cardiac function (e.g., a 3-lead or a 12-lead ECG). In some embodiments, the method includes obtaining a plurality of measurements of the patient's cardiac function that provides a time-series of electrical signals that control movement of the patient's heart.

Returning to the imaging phase, the method includes, while the patient is positioned at the first orientation relative to the radiation source and while obtaining the measurement of the patient's breathing (3212), determining (3214), from the measurement of the patient's breathing, a breathing phase of the patient and determining (3216), from the measurement of the patient's cardiac function, a cardiac phase of the patient (e.g., in real-time). For example, in some embodiments, the cardiac phase of the patient is determined using a zero instruction set computer (ZISC) processor, as described with reference to FIG. 36. The ZISC processor is capable of identifying, within a single cardiac cycle or fraction of a cardiac cycle, that a predefined landmark in the cardiac cycle has occurred (e.g., the S-wave or T-wave).

In some embodiments, the method further includes, before gating the radiation source to expose the patient to radiation (operation 3222, below), obtaining (3218) measurements of the patient's cardiac function from a plurality of cardiac cycles of the patient. In some embodiments, the method includes, using the measurements of the patient's cardiac function from the plurality of cardiac cycles, determining an average interval between a predefined cardiac phase and a beginning of the predefined window of the cardiac cycle. For example, the predefined window of the cardiac cycle represents the interval between the top of the R wave and the beginning of the gating window. For example, in some embodiments, operations 3202 et seq. are performed as part of an imaging period of method 3200.

Method 3200 further includes, prior to the imaging period, undergoing a training period during which information about the patient's cardiac function is obtained. For example, during the training period, ECG measurements of the patient's cardiac function are obtained at regular intervals over a plurality of cardiac cycles (e.g., 15, 20, 50 cardiac cycles, where one cycle corresponds to one complete period of heart motion, such as from one T-wave to the next T-wave). The ECG measurements from the training period are then used to predict quiescent periods of heart movement during the imaging phase, as described below.

In some embodiments, the measurements from the plurality of cardiac cycles of the patient are (3220) waveform measurements (e.g., ECG measurements) of the plurality of cardiac cycles and the method includes validating, as statistically stable, the waveform measurements of the plurality of cardiac cycles.

The method further includes gating (3222) the radiation source to expose the patient to radiation based on a determination that the breathing phase of the patient matches a predefined breathing phase and a determination that the cardiac phase of the patient matches a predefined window of the cardiac cycle. In some embodiments, when the radiation source is gated, the patient's lung is exposed to radiation. In some embodiments, the predefined cardiac window corresponds to a quiescent period of heart movement (e.g., a period of time during the cardiac cycle during which the heart movement is minimal, as described with reference to FIG. 12). In some embodiments, the radiation source is gated within the same cardiac cycle as the determined cardiac phase. In this manner, by gating the exposure of the patient's lung based on a coincidence of breathing phase and a predefined cardiac phase window, a precise area of the lung (e.g., a precise region of lung tissue) is exposed to radiation without perturbation or motion due to heart movement.

In some embodiments, the radiation source is an x-ray imaging apparatus. Gating the radiation source to expose the patient to radiation comprises (3224) gating the x-ray imaging apparatus to produce an x-ray projection of the patient's lung. In some embodiments, as described with reference to method 3100, FIGS. 31A-31B, x-ray projections can be obtained in this manner for a plurality of orientations of the patient with respect to the x-ray imaging source and a plurality of breathing phases. These x-ray projections can then be used to produce a movie of lung motion and/or a biophysical model of the lung (e.g., by relating motion of lung tissue to biophysical parameters, such as stress, strain, elasticity and so on). In some embodiments, in accordance with method 3200, these images are acquired within the predefined cardiac window, to minimize perturbation or motion of the lung due to heart movement.

In some embodiments, the radiation source is a radiation therapy source. Gating the radiation source to expose the patient to radiation comprises (3226) gating the radiation therapy source to irradiate a region of the patient's lung at a therapeutic dose. In these circumstances, it is important to provide as much of the radiation dose as possible to diseased tissue (e.g., cancerous tissue), and as little as possible to healthy tissue. Method 3200 improves radiation therapy devices by delivering more accurate doses to diseased tissue while minimizing radiation provided to healthy tissue.

In some embodiments, determining that the cardiac phase of the patient matches the predefined window of the cardiac cycle includes predicting (3228) the predefined window of the cardiac cycle by, in real-time, detecting (e.g., using BEMP card shown in FIG. 36) the predefined cardiac phase and waiting a length of time corresponding to the average interval between the predefined cardiac phase and the beginning of the predefined window of the cardiac cycle. For example, in some embodiments, a peak of the T-wave is detected and an average interval from the T-wave to the ideal gating window is waited, at which point the radiation source is gated.

It should be understood that the particular order in which the operations in FIGS. 32A-32B have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein are also applicable in an analogous manner to method 3100 described above with respect to FIGS. 32A-32B. Such process are described, for example, with reference to FIG. 2, FIG. 6, FIG. 8, FIG. 11, FIG. 13, FIG. 15, FIG. 21, FIG. 23, FIG. 25, FIG. 27, FIGS. 28A-28B, FIGS. 31A-31B, FIGS. 33A-33C, and FIGS. 34A-34C. For brevity, these details are not repeated here.

Figure 33B:
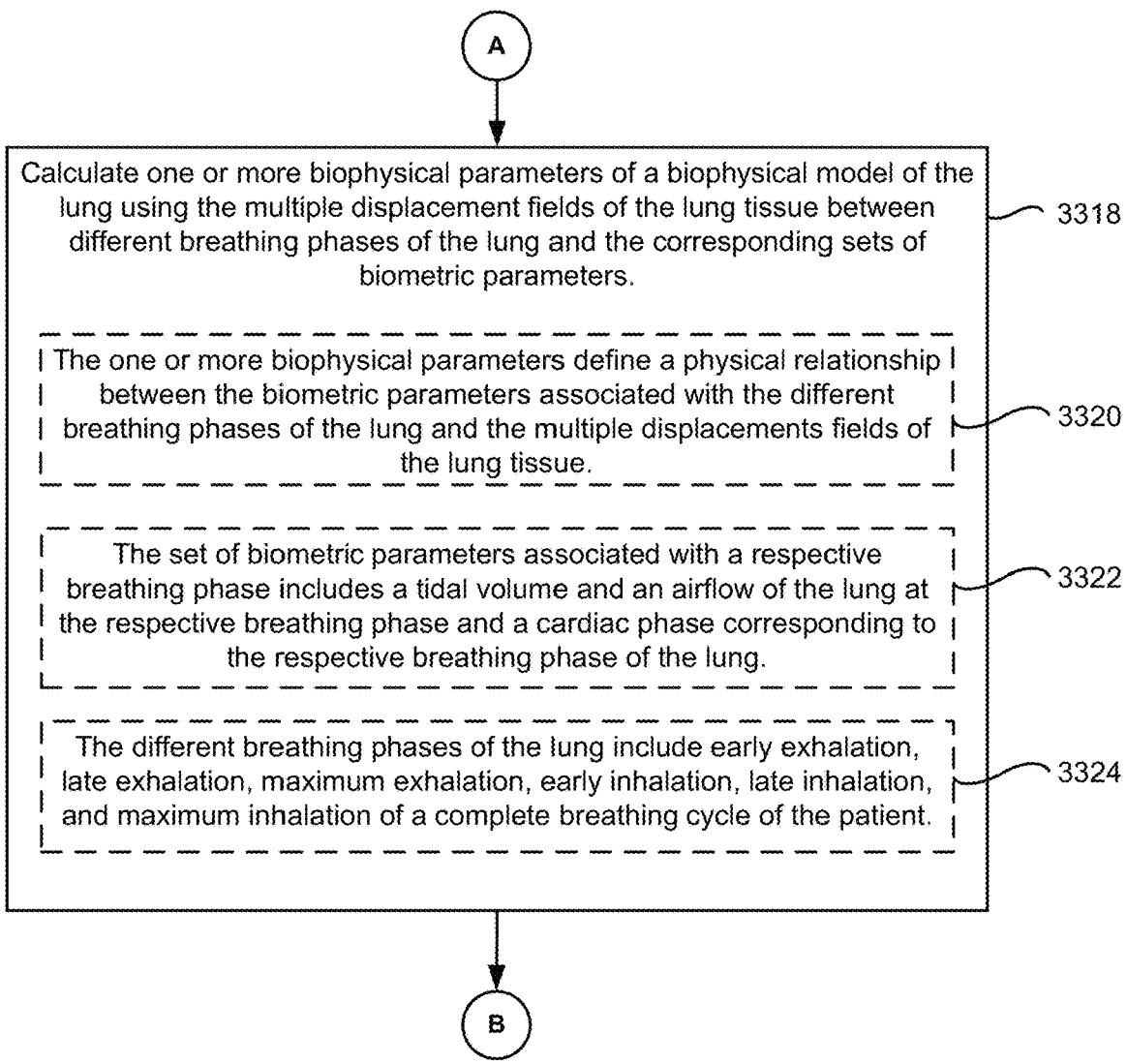
Figure 33C:
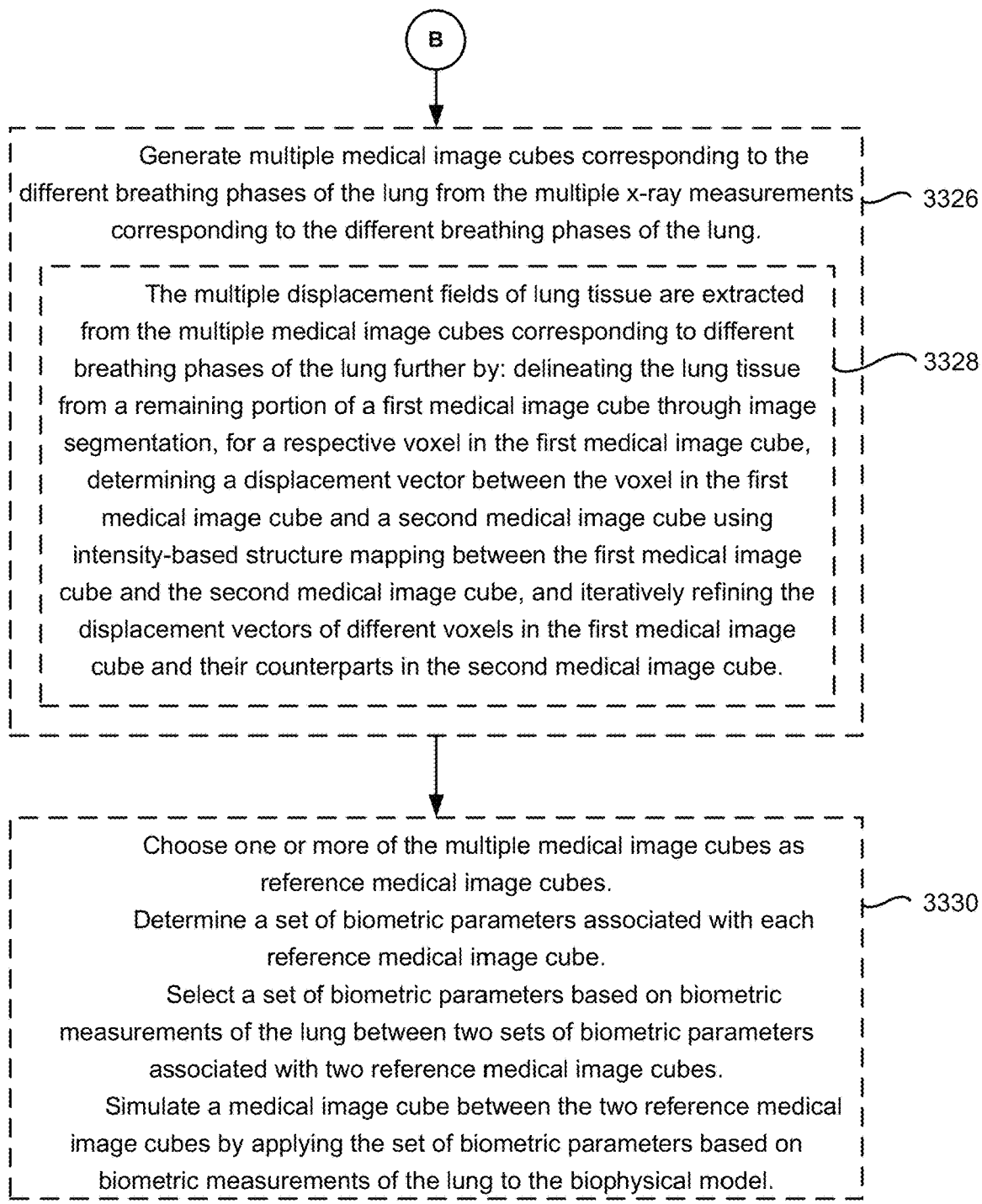

FIGS. 33A-33C are flowcharts of a method 3300 for generating a model of mechanical properties of lung by fitting data from registered images, in accordance with some embodiments. In some embodiments, any or all of the operations described below can be performed without human intervention (e.g., without intervention by a technician). In some embodiments, method 3300 is performed by or using any of the apparatuses described herein (e.g., the GREX imaging system 100 shown in FIG. 1). Some operations of method 3300 are performed by a computer system that includes one or more processors and memory storing instructions which, when executed by the one or more processors, cause the one or more processors to perform the operations of method 3300. Some operations in method 3300 are, optionally, combined and/or the order of some operations is, optionally, changed.

The method includes extracting (3302) multiple displacement fields of lung tissue from the multiple x-ray measurements (e.g., x-ray images, also referred to as x-ray projections) corresponding to different breathing phases of the lung. Each displacement field represents movement of the lung tissue from a first breathing phase to a second breathing phase and each breathing phase has a corresponding set of biometric parameters. In some embodiments, the x-ray measurements are x-ray projections (also called x-ray projection images) obtained in accordance with method 3100 and/or method 3200. In some embodiments, extracting displacement fields from the lung tissue includes identifying a portion of lung tissue in one or more first x-ray projections from a first breathing phase as corresponding to the same portion of lung tissue in one or more second x-ray projections from to a second breathing phase, and determining the displacement of the portion of lung tissue from the first breathing phase to the second breathing phase (e.g., as described with reference to FIG. 28B). In some embodiments, the identifying is performed using a deformable image registration algorithm, as discussed above.

In some embodiments, the multiple x-ray measurements comprise multiple x-ray images, including an x-ray image obtained for the first breathing phase for each of a plurality of orientations of an x-ray imaging apparatus with respect to the patient, thereby forming a plurality of x-ray images corresponding to the first breathing phase and a plurality of x-ray images corresponding to the second breathing phase. In some circumstances, at least one of the x-ray images corresponding to the first breathing phase was obtained during from a different breathing cycle of the patient than a different x-ray image corresponding to the first breathing phase (e.g., the images were obtained during the same phase, but different breaths). In some embodiments, the method includes grouping the multiple x-ray images by breathing phase.

In some embodiments, the method includes extracting multiple vector fields, for which displacement fields are one example.

In some embodiments, one or more sensors are used (3304) for measuring biometric signals of the patient as one or more sequences of time series, including one or more of a 3D spatial position localizer (e.g., 3D spatial localizer 300, FIG. 3), a breathing phase sensor, and a cardiac phase sensor. In some embodiments, the 3D spatial position localizer is configured (3306) for measuring the patient's real-time body movement caused by respiration and heartbeats and outputting them as time series. In some embodiments, the breathing phase sensor is configured (3308) for measuring one or more physiologic metrics related to the patient's breathing, including a tidal volume and its first-order time derivative. In some embodiments, the cardiac phase sensor is configured (3310) for measuring periodic and stationary electrical signals generated by the patient's heart (e.g., an ECG signal). For example, the cardiac phase sensor measures periodic and stationary electrical signals with characteristic features that correspond to the heartbeat phase.

In some embodiments, the biometric signals of the patient measured by the one or more sensors are used for triggering (3312) an x-ray unit to acquire an x-ray image of the patient at a specific breathing and cardiac phase (e.g., as described with reference to method 3200).

In some embodiments, the x-ray unit includes (3314) a clock and the biometric signals of the patient measured by the one or more sensors are synchronized with the x-ray unit's clock. In some embodiments, respective values of the biometric signals are recorded to be associated with the acquired x-ray image.

In some embodiments, the biometric signals of the patient measured during a training window are used (3316) for building an optimized breathing prediction model for predicting a desired breathing phase at which an x-ray unit is triggered to capture an x-ray image of the patient.

The method includes calculating (3318) one or more biophysical parameters of a biophysical model of the lung using the multiple displacement fields of the lung tissue between different breathing phases of the lung and the corresponding sets of biometric parameters. In some embodiments, calculating the one or more biophysical parameters includes calculating one or more derivatives of the displacement field (e.g., a curl, gradient, etc.). In some embodiments, the biophysical parameters are biomechanical parameters (e.g., stress, strain, elastic modulus, elastic limit, etc.). In some embodiments, the one or more biophysical parameters define (3320) a physical relationship between the biometric parameters associated with the different breathing phases of the lung and the multiple displacement fields of the lung tissue. In some embodiments, the set of biometric parameters associated with a respective breathing phase includes (3322) a tidal volume and an airflow of the lung at the respective breathing phase and a cardiac phase corresponding to the respective breathing phase of the lung. In some embodiments, the physical relationship between the biometric parameters associated with the different breathing phases of the lung and the multiple displacement fields of the lung tissue is defined as follows:

$$\vec{U} - \vec{U}_0 = T_V \vec{p}_1 + A_f (\vec{p}_2 + \vec{p}_3) + H_c \vec{p}_4$$

The $\vec{p}_1$ vector describes normal stress caused by tidal volume, $\vec{p}_2$ describes normal stress caused by airflow, $\vec{p}_3$ describes shear stress caused by airflow, and $\vec{p}_4$ describes tissue motion introduced by heart motion, the displacement ($\vec{U} - \vec{U}_0$) of tissue at any point in a closed loop trajectory is expressed as a summation of the stress, strain, and perturbing heart motion vectors scaled by the tidal volume ($T_v$), airflow ($A_f$), and cardiac phase ($H_c$) respectively.

In some embodiments, the different breathing phases of the lung include (3324) early exhalation, late exhalation, maximum exhalation, early inhalation, late inhalation, and maximum inhalation of a complete breathing cycle of the patient.

In some embodiments, the method further includes displaying a visual representation of the biophysical parameters. For example, FIGS. 30A-30B provide examples in which the biophysical parameter is the ratio of $\vec{p}_1$ to ($\vec{p}_2 + \vec{p}_3$). In some embodiments, displaying the visual representation includes displaying an image of the lung, wherein a color of a location within the image of the lung corresponds to the biophysical parameter (e.g., an image of the lung is displayed using a color map of the biophysical parameter). Displaying such visual representation improves the x-ray imaging apparatus itself by increasing the accuracy of diagnoses. For example, it is much easier to see that the patient's left lung is diseased in FIG. 30B than with conventional radiographs, as shown in FIG. 29.

In some embodiments, the method further includes generating (3326) multiple medical image cubes corresponding to the different breathing phases of the lung from the multiple x-ray measurements corresponding to the different breathing phases of the lung (e.g., as described with reference to FIG. 21). In some embodiments, the multiple displacement fields of lung tissue are extracted (3328) from the multiple medical image cubes corresponding to different breathing phases of the lung further by delineating the lung tissue from a remaining portion of a first medical image cube through image segmentation and, for a respective voxel in the first medical image cube, determining a displacement vector between the voxel in the first medical image cube and a second medical image cube using intensity-based structure mapping between the first medical image cube and the second medical image cube. The multiple displacement fields of lung tissue are extracted from the multiple medical image cubes corresponding to different breathing phases of the lung further by iteratively refining the displacement vectors of different voxels in the first medical image cube and their counterparts in the second medical image cube.

In some embodiments, the method further comprises choosing (3330) one or more of the multiple medical image cubes as reference medical image cubes, determining a set of biometric parameters associated with each reference medical image cube, selecting a set of biometric parameters based on biometric measurements of the lung between two sets of biometric parameters associated with two reference medical image cubes, and simulating a medical image cube between the two reference medical image cubes by applying the set of biometric parameters based on biometric measurements of the lung to the biophysical model.

It should be understood that the particular order in which the operations in FIGS. 33A-33C have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein are also applicable in an analogous manner to method 3100 described above with respect to FIGS. 32A-32B. Such process are described, for example, with reference to FIG. 2, FIG. 6, FIG. 8, FIG. 11, FIG. 13, FIG. 15, FIG. 21, FIG. 23, FIG. 25, FIG. 27, FIGS. 28A-28B, FIGS. 31A-31B, FIGS. 32A-32B, and FIGS. 34A-34C. For brevity, these details are not repeated here.

Figure 34B:
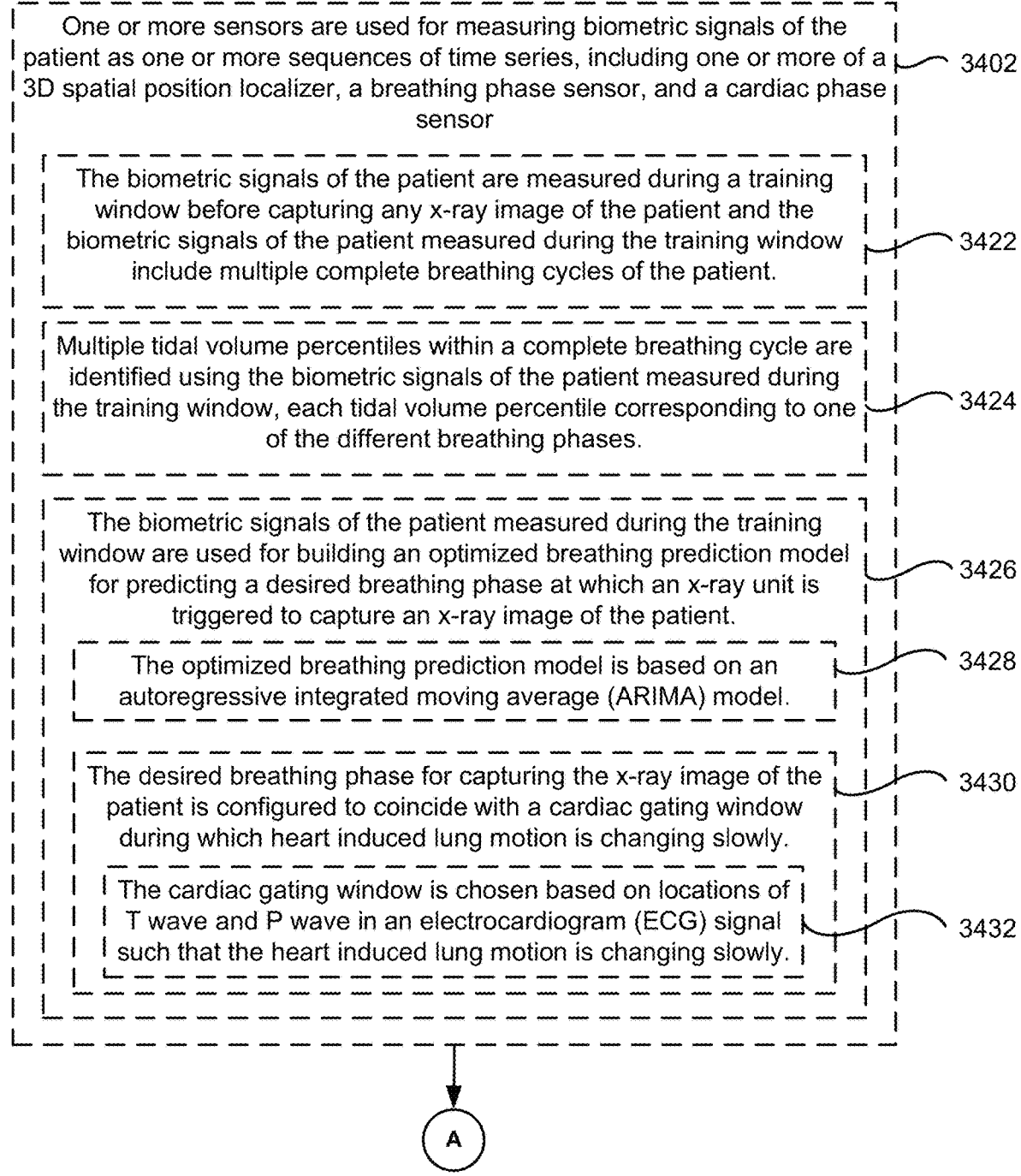
Figure 34C:
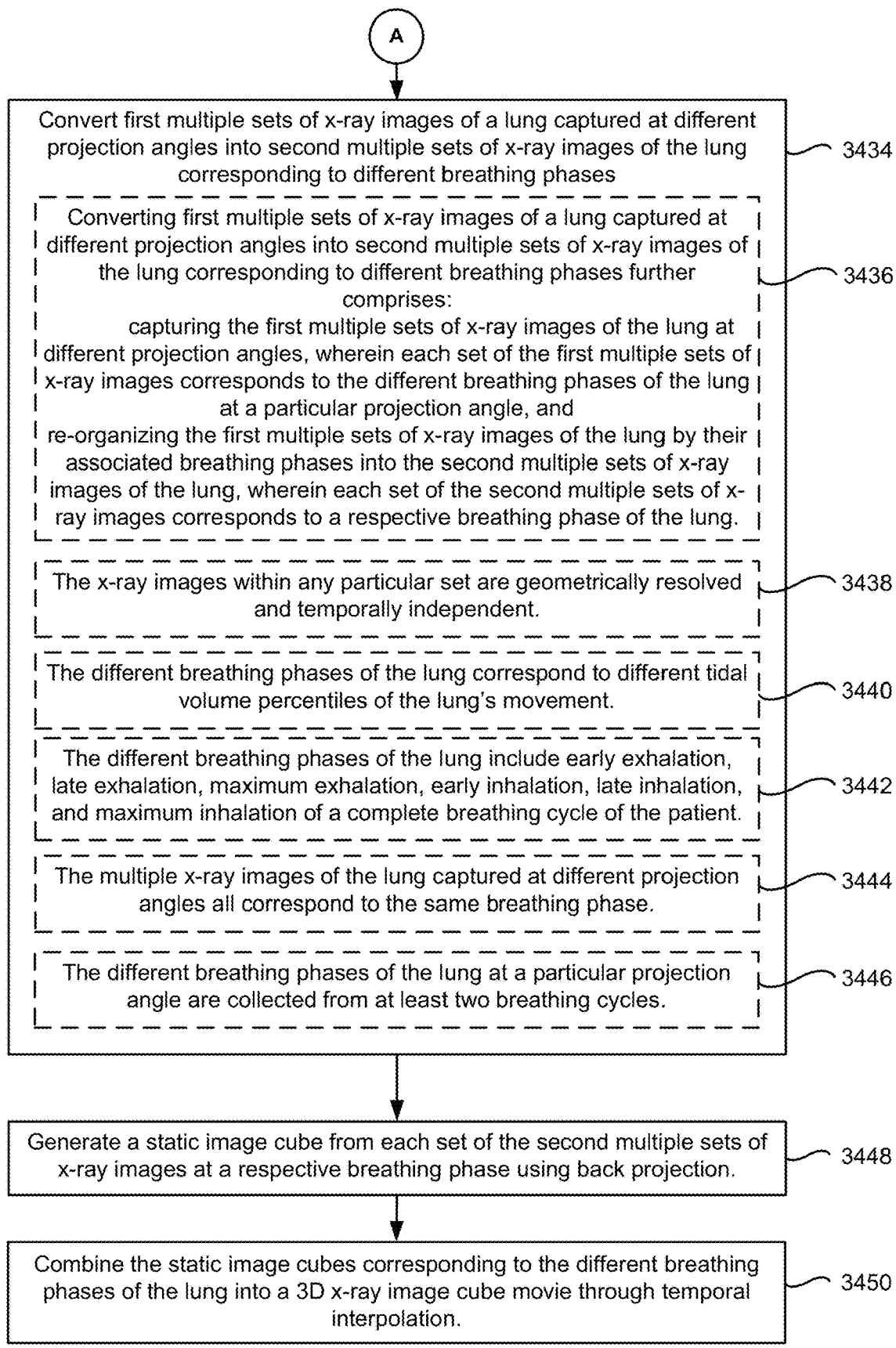

FIGS. 34A-34C are flowcharts illustrating a method 3400 for generating a 3D x-ray image cube movie from 2D x-ray images of a patient. In some embodiments, any or all of the operations described below can be performed without human intervention (e.g., without intervention by a technician). In some embodiments, method 3300 is performed by or using any of the apparatuses described herein (e.g., the GREX imaging system 100 shown in FIG. 1). Some operations of method 3400 are performed by a computer system that includes one or more processors and memory storing instructions which, when executed by the one or more processors, cause the one or more processors to perform the operations of method 3300. Some operations in method 3400 are, optionally, combined and/or the order of some operations is, optionally, changed.

In some embodiments, one or more sensors are used (3402) for measuring biometric signals of the patient as one or more sequences of time series, including one or more of a 3D spatial position localizer, a breathing phase sensor, and a cardiac phase sensor (e.g., as described above with reference to method 3100 and method 3200).

In some embodiments, the method further comprises identifying (3406) a cardiac phase gating window using one or more cardiac phase sensor measurements, predicting a breathing phase using one or more breathing phase sensor measurements, identifying a coincidence between the cardiac phase gating window and the predicted breathing phase for generating an x-ray imaging pulse, and tagging an x-ray image corresponding to the x-ray imaging pulse with the breathing phase, the cardiac phase, and 3D spatial position localizer measurements (e.g., as described above with reference to method 3200).

In some embodiments, the 3D spatial position localizer is configured (3408) for measuring the patient's real-time body movement caused by respiration and heartbeats and outputting them as time series (e.g., as described above with reference to method 3100 and method 3200).

In some embodiments, the breathing phase sensor is configured (3410) for measuring one or more physiologic metrics related to the patient's breathing, including a tidal volume and its first-order time derivative. For example, the rate of tidal volume changes over time or airflow.

In some embodiments, the cardiac phase sensor is configured (3412) for measuring periodic and stationary electrical signal generated by the patient's heart, with characteristic features that correspond to the cardiac phase.

In some embodiments, two distinct filters are used (3414) to remove signal drift and noise from biometric signals of the patient after being synchronized with an x-ray unit's clock.

In some embodiments, the biometric signals of the patient measured by the one or more sensors are used (3416) for triggering an x-ray unit to acquire an x-ray image of the patient at a specific breathing and cardiac phase.

In some embodiments, the x-ray unit includes (3418) a clock. The biometric signals of the patient measured by the one or more sensors are synchronized with the x-ray unit's clock and the respective values of the biometric signals are recorded to be associated with the acquired x-ray image.

In some embodiments, the biometric signals of the patient are measured (3422) during a training window (e.g., a training period) before capturing any x-ray image of the patient and the biometric signals of the patient measured during the training window include multiple complete breathing cycles of the patient (e.g., as described above with reference to method 3100 and method 3200).

In some embodiments, multiple tidal volume percentiles within a complete breathing cycle are identified (3424) using the biometric signals of the patient measured during the training window, each tidal volume percentile corresponding to one of the different breathing phases.

In some embodiments, the biometric signals of the patient measured during the training window are used (3426) for building an optimized breathing prediction model for predicting a desired breathing phase at which an x-ray unit is triggered to capture an x-ray image of the patient.

In some embodiments, the optimized breathing prediction model is (3428) based on an autoregressive integrated moving average (ARIMA) model.

In some embodiments, the desired breathing phase for capturing the x-ray image of the patient is configured (3430) to coincide with a cardiac gating window during which heart induced lung motion is changing slowly.

In some embodiments, the cardiac gating window is chosen (3432) based on locations of T wave and P wave in an electrocardiogram (ECG) signal such that the heart induced lung motion is changing slowly.

The method includes converting (3434) first multiple sets of x-ray images of a lung captured at different projection angles into second multiple sets of x-ray images of the lung corresponding to different breathing phases.

In some embodiments, converting first multiple sets of x-ray images of a lung captured at different projection angles into second multiple sets of x-ray images of the lung corresponding to different breathing phases further comprises (3436) capturing the first multiple sets of x-ray images of the lung at different projection angles. Each set of the first multiple sets of x-ray images corresponds to the different breathing phases of the lung at a particular projection angle. In some embodiments, converting first multiple sets of x-ray images of a lung captured at different projection angles into second multiple sets of x-ray images of the lung corresponding to different breathing phases further comprises re-organizing the first multiple sets of x-ray images of the lung by their associated breathing phases into the second multiple sets of x-ray images of the lung. Each set of the second multiple sets of x-ray images corresponds to a respective breathing phase of the lung.

In some embodiments, the x-ray images within any particular set are (3438) geometrically resolved and temporally independent.

In some embodiments, the different breathing phases of the lung correspond (3440) to different tidal volume percentiles of the lung's movement.

In some embodiments, the different breathing phases of the lung include (3442) early exhalation, late exhalation, maximum exhalation, early inhalation, late inhalation, and maximum inhalation of a complete breathing cycle of the patient.

In some embodiments, n the multiple x-ray images of the lung captured at different projection angles all correspond (3444) to the same breathing phase.

In some embodiments, the different breathing phases of the lung at a particular projection angle are collected (3446) from at least two breathing cycles.

The method includes generating (3448) a static image cube from each set of the second multiple sets of x-ray images at a respective breathing phase using back projection.

The method includes combining (3450) the static image cubes corresponding to the different breathing phases of the lung into a 3D x-ray image cube movie through temporal interpolation.

It should be understood that the particular order in which the operations in FIGS. 34A-34C have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein are also applicable in an analogous manner to method 3100 described above with respect to FIGS. 34A-34C. Such process are described, for example, with reference to FIG. 2, FIG. 6, FIG. 8, FIG. 11, FIG. 13, FIG. 15, FIG. 21, FIG. 23, FIG. 25, FIG. 27, FIGS. 28A-28B, FIGS. 31A-31B, FIGS. 32A-32B, and FIGS. 33A-33C. For brevity, these details are not repeated here.

FIG. 35 depicts an exemplary patient positioning fixture (PPF) 3501 (e.g., a rotatable chair) for supporting a patient 3502 in accordance with some embodiments. In some embodiments, PPF 3501 rotates (e.g., along rotation 3503) to position the patient 2502 at a plurality of angles (e.g., orientations) with respect to radiation source 3504 (e.g., an x-ray imaging system or a radiation therapy system). For example, the PPF moves in such a way as to move the patient to the desired position (e.g., the patient does not need to move independently) so that the radiation device 3504 is enabled to capture x-ray images of the patient at various angles. In some embodiments, the patient 3502 rotates (e.g., along rotation 3502) to achieve the plurality of angles without rotating the PPF 3501. In some embodiments, the PPF 3501 and/or the patient 3205 are automatically rotated and/or moved (e.g., using a motor) to a desired position. In some embodiments, a technician rotates and/or moves patient 3502. In some embodiments, a flat panel detector unit 3505 is positioned behind the patient relative to the radiation device 3504.

In some embodiments, one or more cameras 3506-1 to 3506-$m$ are used to detect objects within a predefined area (e.g., a room) surrounding PPF 3501. For example, the camera(s) 3506 capture if an object will collide with the PPF 3501 as the PPF 3501 is moved around (and rotated within) the predefined area. In some implementations, a method for collision avoidance between PPF 3501 (and patient 3502) is provided.

In some embodiments, one or more 3D imaging sensors (e.g., LIDAR sensors or structured light sensors) are used to geometrically monitor the breathing of the patient 3502, as described with reference to method 3100.

Figure 36:
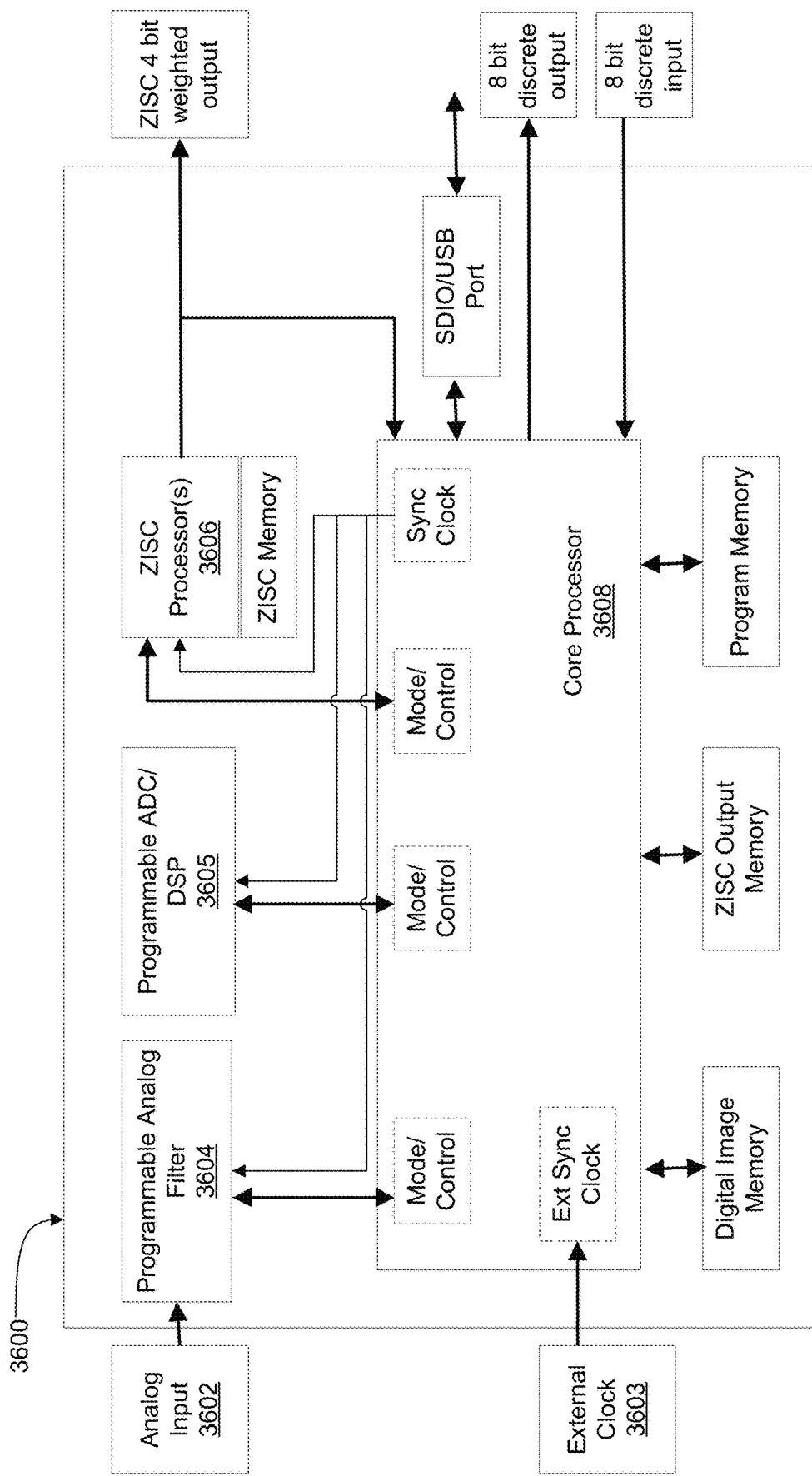
FIG. 36 depicts an exemplary biological event monitoring process (BEMP) card, in accordance with some embodiments.

FIG. 36 depicts an exemplary biological event monitoring process (BEMP) card 3600. BEMP card 3600 includes a programmable analog filter; a programmable analog to digital converter (ADC)/digital signal processor (DSP) 3605; and a zero instruction set computer (ZISC) processor 3606. The BEMP card 3600 receives an analog input signal 3602, which comprises a biometric signal of the patient. In some embodiments, the analog input 3602 comprises an ECG signal. In some embodiments, the analog input is a 3-lead ECG signal or a 12-lead ECG signal. The ZISC processor 3606 detects predefined patterns in the analog input in real-time. For example, the ZISC processor(s) 3606 detects an R wave in an ECG signal to predict when the next quiescent period of the patient's cardiac cycle will be (e.g., in the TP interval). In some embodiments, the ZISC processor 3606 outputs the ZISC 4 bit weighted output that can be used to trigger a radiation source (e.g., an x-ray imaging system or a radiation therapy system). In some embodiments, a clock signal 3603 for the BEMP card 3600 is provided from an external source, such as the radiation source, so that the BEMP card 3600 can be synchronized to the radiation source.

The computational techniques discussed throughout the post-processing software 106 section are computationally resource-intensive. Many community hospitals and small clinics do not have access to the computer hardware necessary to create the movies, calculate the biomechanical models, and present results with a fast, smooth experience for the end-user. The post-processing software 106's functions are performed in the cloud so that the end-user can have access to the post-processing software 106's powerful visualization tools on a treatment console, office desktop, or work laptop.

Figure 37A:
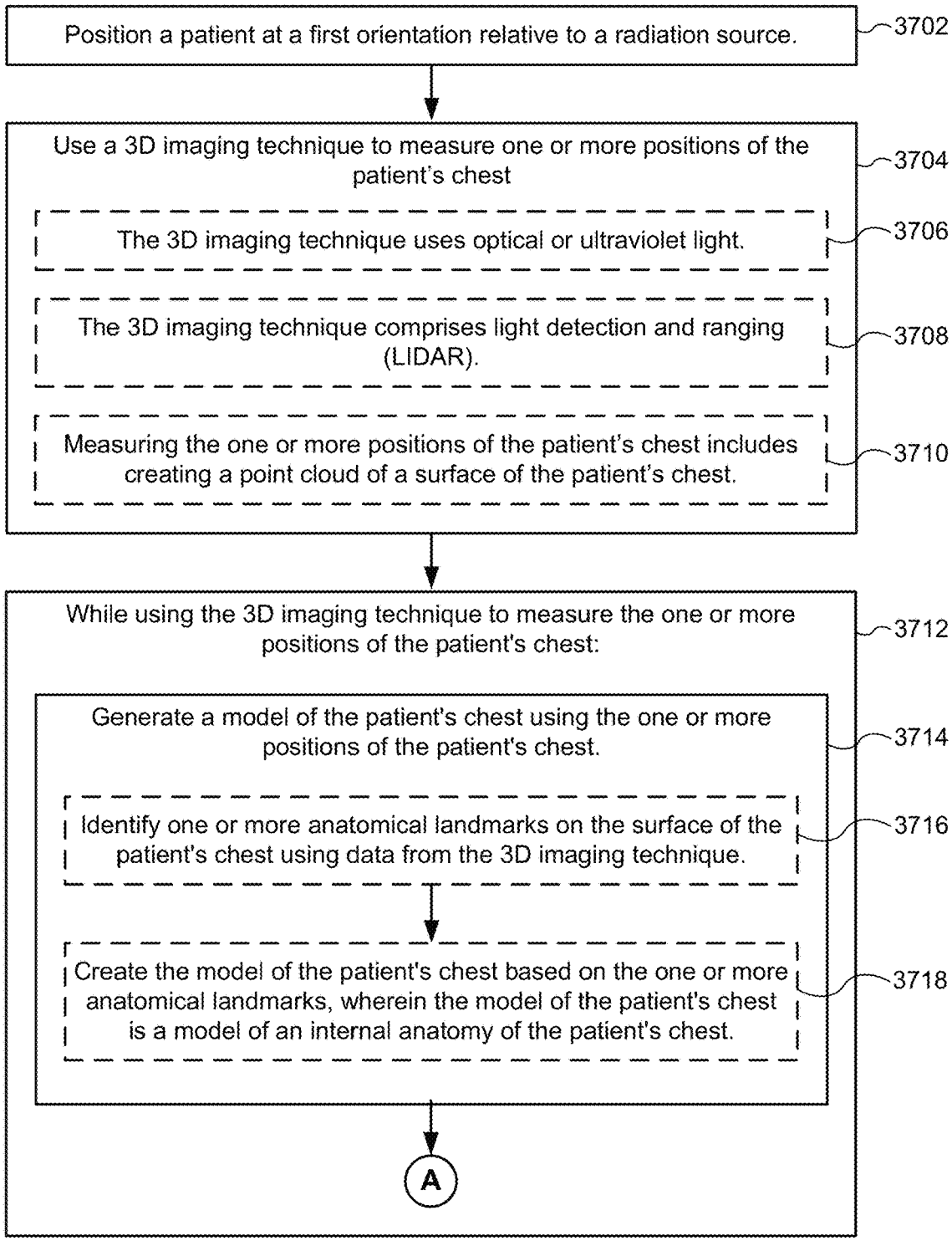
FIGS. 37A-37B are flow diagrams illustrating a method for determining a dose of radiation to which to expose a patient, in accordance with some embodiments.
Figure 37B:
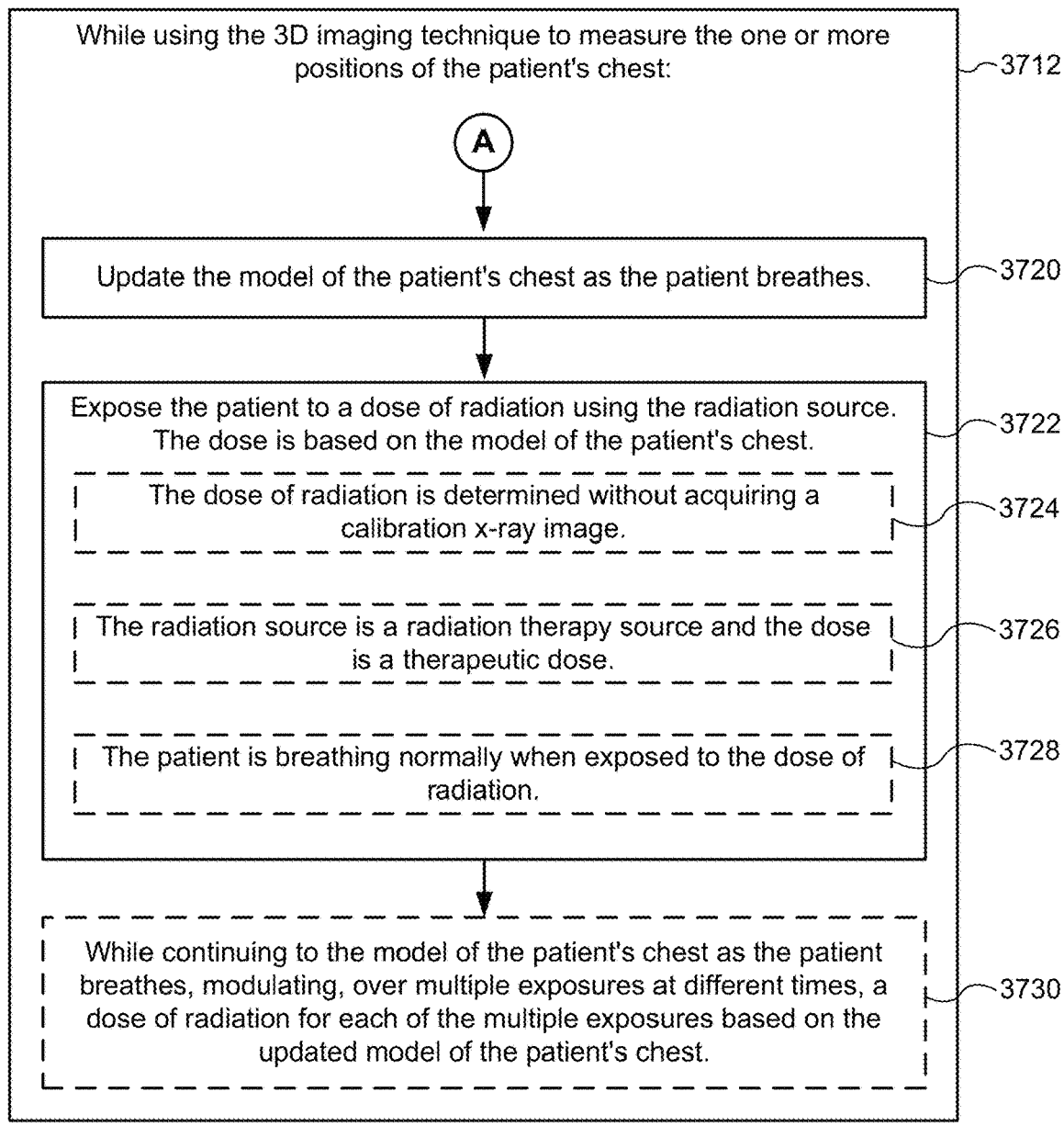

FIGS. 37A-37B are flowcharts illustrating a method 3700 for determining a dose of radiation to which to expose a patient, in accordance with some embodiments. In some embodiments, any or all of the operations described below can be performed without human intervention (e.g., without intervention by a technician). In some embodiments, method 3700 is performed by or using any of the apparatuses described herein (e.g., the GREX imaging system 100 shown in FIG. 1). Some operations of method 3700 are performed by a computer system that includes one or more processors and memory storing instructions which, when executed by the one or more processors, cause the one or more processors to perform the operations of method 3700. Some operations in method 3700 are, optionally, combined and/or the order of some operations is, optionally, changed.

Note that, in some embodiments, method 3700 is performed during an imaging protocol or phase (e.g., rather than a calibration protocol or phase). Further, while specific embodiments are described below with respect to modeling and irradiating the patient's chest, it should be understood that method 3700 may be used, in accordance with other embodiments, to model and irradiate a first portion of the patient's body other than the patient's chest.

Method 3700 includes positioning (3702) a patient at a first orientation relative to a radiation source. In some embodiments, the radiation source is an x-ray imaging source. Positioning a patient relative to a radiation source is described in greater detail throughout this disclosure, for example with reference to the GREX imaging system show in FIG. 1. For brevity, those details are not repeated here.

Method 3700 further includes using (3704) a 3D imaging technique to measure one or more positions of the patient's chest (e.g., one or more positions of a skin surface of the patient's chest). As noted above, in some embodiments, the 3D imaging technique is used to measure a first portion of the patient's body that is not the patient's chest (e.g., the patient's abdomen, skull, leg, foot). In some embodiments, the 3D imaging technique uses (3706) (e.g., is based on) optical or ultraviolet light (e.g., is a non-x-ray imaging technique). In some embodiments, the 3D imaging technique uses sound (e.g., is a sonic or ultrasonic 3D imaging technique). In some embodiments, the 3D imaging technique using a 3D imaging detector that is distinct from an x-ray detector used for x-ray imaging. In some embodiments, the 3D imaging technique is not a computed tomography (CT) technique. In some embodiments, the 3D imaging technique uses a frequency of light that does not penetrate the surface of a human body. In some embodiments, the dose of radiation has a first frequency of light and the 3D imaging technique uses a second frequency of light different from the first frequency of light (e.g., at least an order of magnitude different). In some embodiments, the 3D imaging technique is a multispectral imaging technique. In some embodiments, the 3D imaging technique does not rely on transmission of radiation through the patient chest (e.g., the 3D imaging technique is performed using a light source and a detector (e.g., a camera) that images a surface of the patient that is illuminated by the light source). In some embodiments, the frequency of light does penetrate a garment worn by the patient during the method (e.g., does penetrate a modest garment). In some embodiments, the 3D imaging technique acquires images of the surface of the patient's chest and measures the one or more positions of the patient's chest using the images of the surface of the patient's chest. In some embodiments, the 3D imaging technique comprises (3708) light detection and ranging (LIDAR).

In some embodiments, measuring the one or more positions of the patient's chest includes (3710) creating a point cloud of a surface of the patient's chest (e.g., as described with reference to FIG. 38A).

In some embodiments, method 3700 includes, while using the 3D imaging technique to measure the one or more positions of the patient's chest (3712), performing the operations described with reference to 3714-3730.

The method includes generating (3714) a model of the patient's chest (e.g., of the shape of the surface of the patient's chest, or, more generally, a model of the first portion of the patient's body) using the one or more positions of the patient's chest. In some embodiments, generating the model of the patient's chest includes identifying (3716) one or more anatomical landmarks on the surface of the patient's chest using data from the 3D imaging technique and creating (3718) the model of the patient's chest (e.g., a spatial distribution of the density of the patient's chest) based on the one or more anatomical landmarks, wherein the model of the patient's chest is a model of an internal anatomy of the patient's chest. In some embodiments, updating the model of the patient's chest as the patient breathes includes updating positions of the one or more anatomical landmarks and updating the model of the internal anatomy based on the updated positions of the one or more anatomical landmarks. In some embodiments, the model of the internal anatomy of the patient's chest includes a plurality of model points corresponding to regions inside the patient's chest, and each model point of the plurality of model points is associated with an x-ray cross-section (e.g., based on an a corresponding electron density of bodily tissue that is determined to be associated with the model point, e.g., using data from the Medical Internal Radiation Dose (MIRD) Anatomic Database).

The method includes updating (3720) the model of the patient's chest as the patient breathes (e.g., repeatedly performing some or all of the operations described with reference generating the model of the patient's chest, so that the model of the patient's chest is a real-time or near-real-time model of the patient's chest as the patient breathes).

The method includes exposing (3722) the patient to a dose of radiation using the radiation source. In some embodiments, the dose of radiation is applied to the patient's chest (or, more generally, to the first portion of the patient's body).

The dose is based on the model of the patient's chest (e.g., one or more exposure parameters, such as a magnitude and/or duration of the dose, is based on the model of the patient's chest for a current breathing phase corresponding to a time that the patient is exposed to the dose of radiation). In some embodiments, the method includes determining the dose based on the model of the patient's chest (e.g., automatically, without human intervention). In some embodiments, the dose of radiation is determined without acquiring (3724) a calibration x-ray image. In some embodiments, the dose of radiation is determined in accordance with the x-ray cross-sections of the model points along a path of the radiation. In some embodiments, the dose is determined based on the x-ray cross-sections (e.g., electron densities) along a vector through the model of the patient's chest. where the vector is along a direction of propagation of the radiation from the radiation source (e.g., the vector is a beams-eye view through the patient, connecting the radiation source to the x-ray imaging detector).

In some embodiments, the radiation source is (3726) a radiation therapy source and the dose is a therapeutic dose. In some embodiments, the radiation source is an x-ray imaging source and the dose is a diagnostic dose (e.g., a dose sufficient to provide a predefined signal-to-noise ratio in resulting images).

In some embodiments, the patient is (3728) breathing normally when (e.g., while) exposed to the dose of radiation (e.g., the patient is not holding his or her breath).

In some embodiments, method 3700 includes while using the 3D imaging technique to measure the one or more positions of the patient's chest and while continuing to update the model of the patient's chest as the patient breathes, modulating (3730), over multiple exposures at different times, a dose of radiation for each of the multiple exposures based on the updated model of the patient's chest (e.g., by modulating a current in a linear accelerator used to produce the dose of radiation). To that end, in some embodiments, the dose of radiation is a first dose of radiation of a plurality of doses of radiation to which the patient is exposed. In some embodiments, the patient is exposed to the first dose of radiation at a first breathing phase and the first dose of radiation is based on the model of the patient's chest at the first breathing phase. In some embodiments, the method includes exposing the patient to a second dose of radiation at a second breathing phase distinct from the first breathing phase, where the second dose of radiation is based on the updated model at the second breathing phase. In some circumstance, the second dose of radiation is obtained while the patient is positioned at the first orientation relative to the radiation source, and the second dose of radiation is further based on the first orientation (e.g., based on a vector through the model of the patient's chest). In some circumstance, the second dose of radiation is obtained while the patient is positioned at a second orientation relative to the radiation source, and the second dose of radiation is further based on the second orientation (e.g., based on a vector through the model of the patient's chest).

Note that method 3700 can be used to determine radiation parameters for any of the radiation exposures described herein. For example, method 3700 may be combined with any of the other methods described herein to determine a dose and/or length of exposure of radiation. Thus, for example, biophysical models of patient's lung can be generated, as described with reference to method 3300, with appropriate dosage.

Figure 38A:
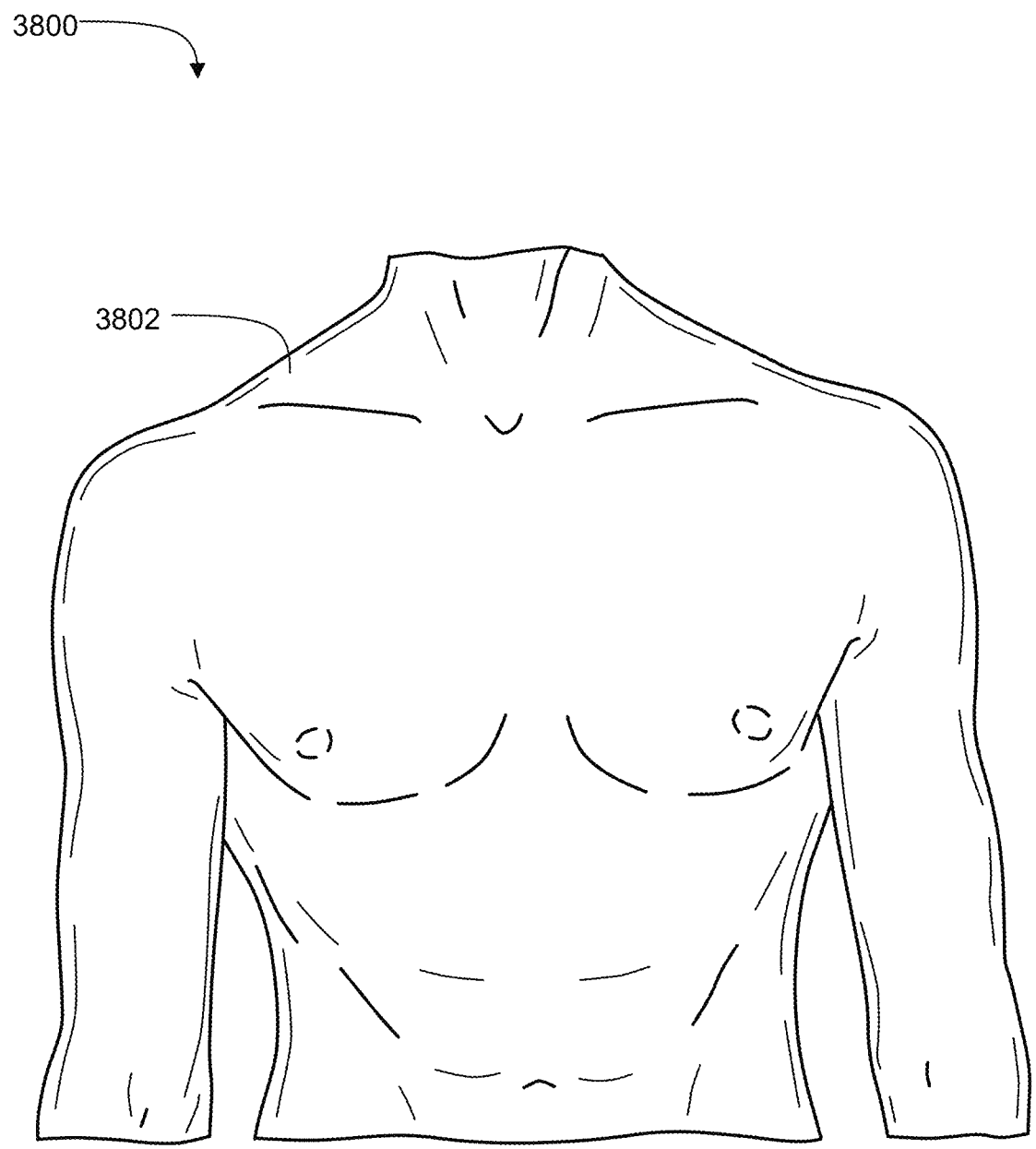
FIGS. 38A-38C illustrate a process for generating a model of a patient's chest, in accordance with some embodiments.
Figure 38B:
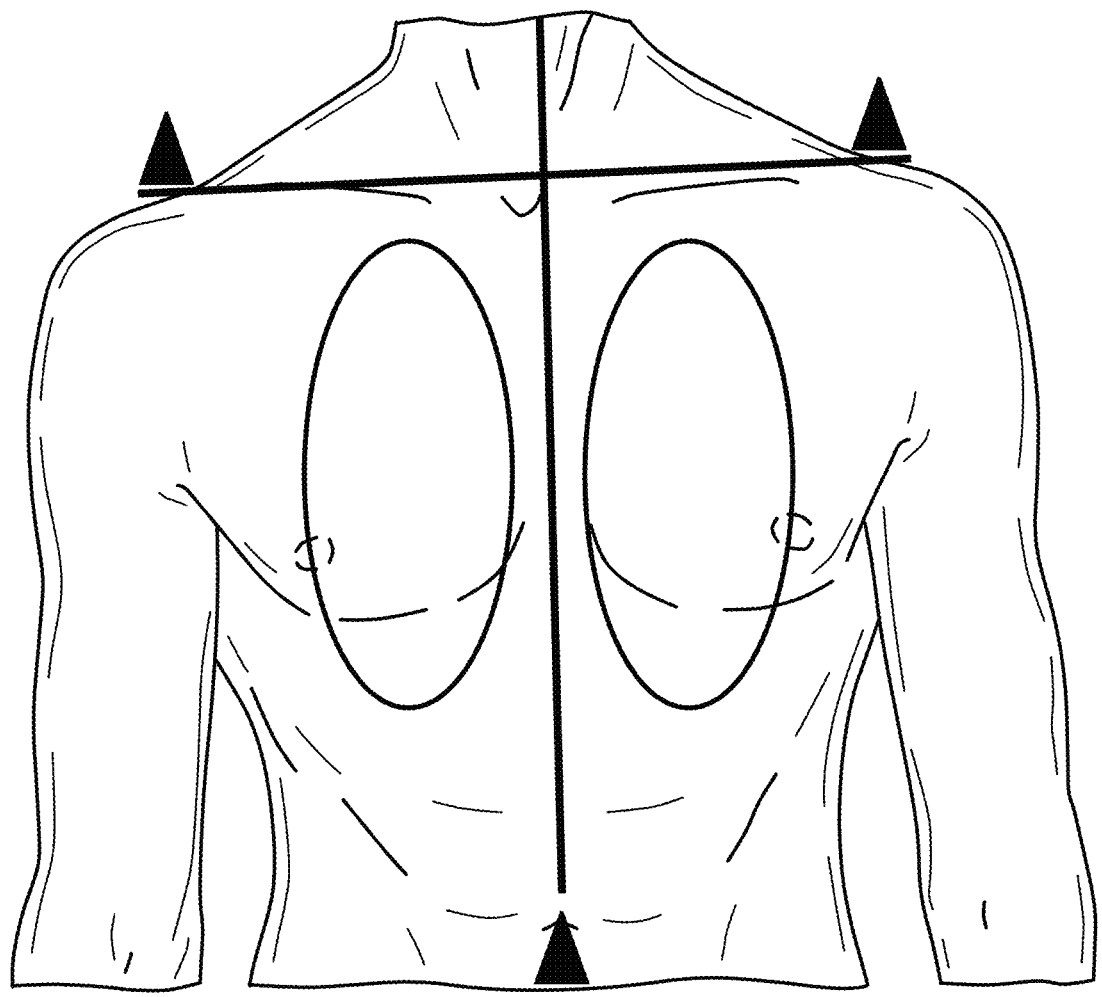
Figure 38C:
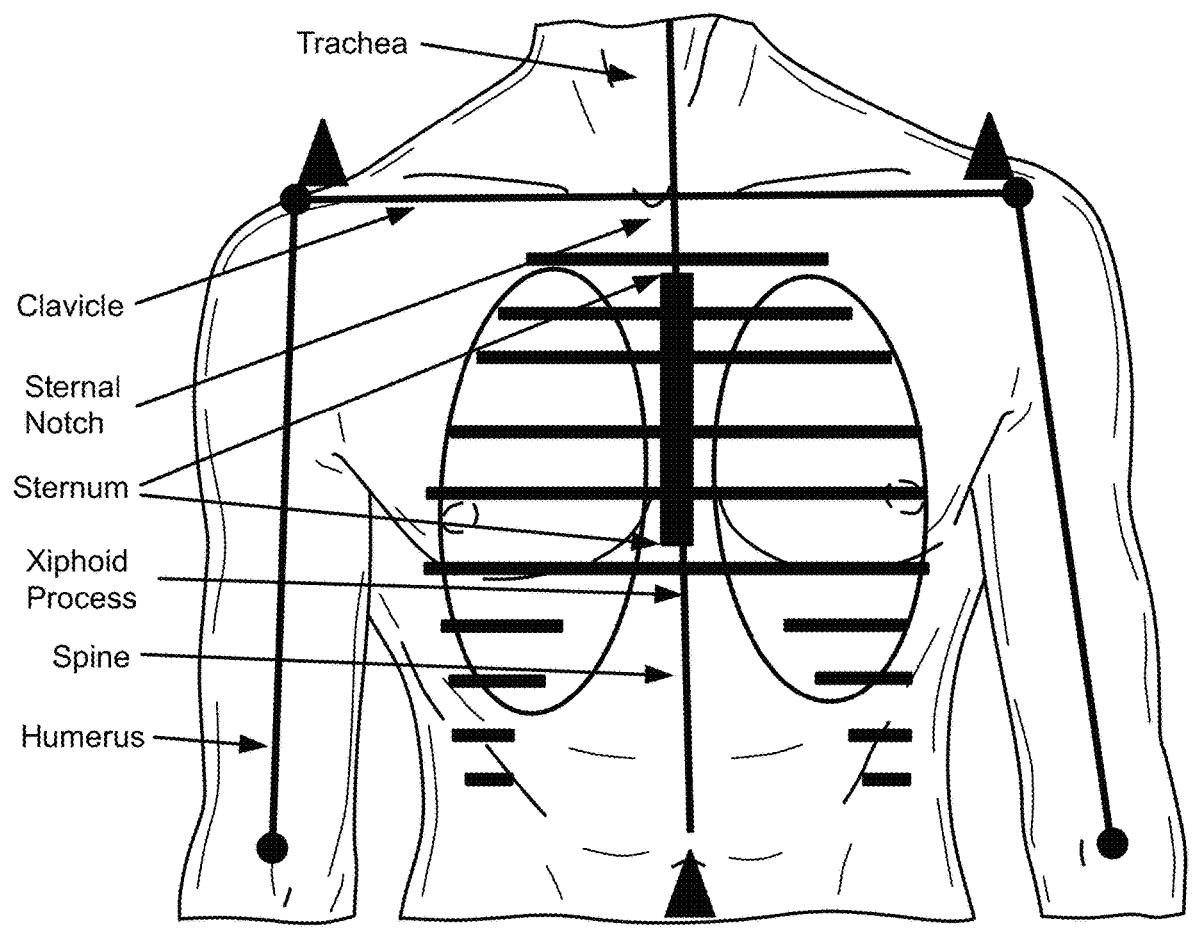

FIGS. 38A-38C illustrate a process for generating a model of a patient's chest, in accordance with some embodiments. FIG. 38A illustrates the result of measurements of positions on a patient 3800's chest, using a 3D imaging technique (e.g., such as LIDAR). For example, in some embodiments, the measurements of the positions of the patient's chest (e.g., skin surface positions) are used to create a point cloud 3802 of a surface of the patient's chest. As shown in FIG. 38B, one or more anatomical landmarks (such as the patient 3800's navel and/or a portion of the patient 3800's clavical) can be identified from the point cloud. In some embodiments, as shown in FIG. 38C, the model (e.g., 3D or internal model) of the patient's chest is based on the one or more anatomical landmarks. For example, in some embodiments, creating the model of the patient's chest includes scaling (e.g., "rigging") a known skeletal and/or soft-tissue structure based on the positions of the anatomical landmarks. For example, creating the model of the patient's chest includes generating model points with x-ray cross-sections corresponding to the following bones: the clavicle, sternal notch, sternum, xiphoid process, spine, humerus, and others.

Reference throughout this specification to "an embodiment," "some embodiments," "one embodiment", "another example," "an example," "a specific example," or "some examples," means that a particular feature, structure, material, or characteristic described in connection to the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method of x-ray imaging, comprising:
positioning a patient at a first orientation relative to an x-ray imaging source;
using a 3D imaging technique, distinct from x-ray imaging, to measure one or more positions of the patient's chest;
while using the 3D imaging technique to measure the one or more positions of the patient's chest:
generating a model of the patient's chest using the one or more positions of the patient's chest;
updating the model of the patient's chest as the patient breathes; and
obtaining an x-ray image of the patient's chest, including exposing the patient to a dose of radiation using the x-ray imaging source that is calculated using the model of the patient's chest.

2. The method of claim 1, wherein the 3D imaging technique uses optical or ultraviolet light.

3. The method of claim 1 wherein the 3D imaging technique comprises light detection and ranging (LIDAR).

4. The method of claim 1, wherein the dose of radiation is determined without acquiring a calibration x-ray image.

5. The method of claim 1, wherein generating the model of the patient's chest includes:
identifying one or more anatomical landmarks on the surface of the patient's chest using data from the 3D imaging technique; and
creating the model of the patient's chest based on the one or more anatomical landmarks, wherein the model of the patient's chest is a model of an internal anatomy of the patient's chest.

6. The method of claim 1, wherein the patient is breathing normally when exposed to the dose of radiation.

7. The method of claim 1, wherein measuring the one or more positions of the patient's chest includes creating a point cloud of a surface of the patient's chest.

8. The method of claim 1, further comprising obtaining multiple x-ray images of the patient's chest using multiple exposures at different times, including modulating, over the multiple exposures at different times, the dose of radiation based on the model of the patient's chest in real-time.

9. The method of claim 8, wherein the multiple exposures at different times includes a plurality of exposures with the patient positioned at the first orientation relative to the x-ray imaging source.

10. The method of claim 8, wherein the multiple exposures at different times includes a plurality of exposures with the patient positioned at a second orientation, distinct from the first orientation, relative to the x-ray imaging source.

11. The method of claim 8, wherein the modulating the dose of radiation includes modulating a number of photons used to obtain respective x-ray images.

12. The method of claim 1, wherein a magnitude or duration of the dose is based on the model of the patient's chest.

13. The method of claim 1, wherein:
the x-ray image is a first x-ray image that has a first magnitude, and
the method further comprises:
at a later time after obtaining the first x-ray image of the patient's chest, exposing the patient to a second dose of radiation using the x-ray imaging source that is calculated using the model of the patient's chest, wherein the second dose has a second magnitude that is different from the first magnitude.

14. The method of claim 1, wherein:
the x-ray image is a first x-ray image that has a first duration, and
the method further comprises:
at a later time after obtaining the first x-ray image of the patient's chest, exposing the patient to a second dose of radiation using the x-ray imaging source that is calculated using the model of the patient's chest, wherein the second dose has a second duration that is different from the first duration.

15. The method of claim 1, wherein the x-ray image is obtained at a mid-inhalation or mid-exhalation breathing phase of the patient.

16. A system, comprising:
one or more processors; and
memory storing instructions which, when executed by the one or more processors, cause the one or more processors to perform a set of operations, including:
positioning a patient at a first orientation relative to an x-ray imaging source;
using a 3D imaging technique, distinct from x-ray imaging, to measure one or more positions of the patient's chest;
while using the 3D imaging technique to measure the one or more positions of the patient's chest:

generating a model of the patient's chest using the one or more positions of the patient's chest;

updating the model of the patient's chest as the patient breathes; and obtaining an x-ray image of the patient's chest, including exposing the patient to a dose of radiation using the x-ray imaging source that is calculated using the model of the patient's chest.

17. The system of claim 16, wherein the 3D imaging technique uses optical or ultraviolet light.

18. The system of claim 16, wherein the 3D imaging technique comprises light detection and ranging (LIDAR).

19. The system of claim 16, wherein the dose of radiation is determined without acquiring a calibration x-ray image.

20. The system of claim 16, wherein generating the model of the patient's chest includes:

identifying one or more anatomical landmarks on the surface of the patient's chest using data from the 3D imaging technique; and creating the model of the patient's chest based on the one or more anatomical landmarks, wherein the model of the patient's chest is a model of an internal anatomy of the patient's chest.

21. The system of claim 16, wherein the patient is breathing normally when exposed to the dose of radiation.

22. The system of claim 16, wherein measuring the one or more positions of the patient's chest includes creating a point cloud of a surface of the patient's chest.

23. The system of claim 16, wherein the memory further comprises instructions for obtaining multiple x-ray images of the patient's chest using multiple exposures at different times, including modulating, over the multiple exposures at different times, the dose of radiation based on the model of the patient's chest in real-time.

24. The system of claim 16, wherein a magnitude or duration of the dose is based on the model of the patient's chest.

25. The system of claim 16, wherein:

the x-ray image is a first x-ray image that has a first magnitude, and the set of operations further comprises:

at a later time after obtaining the first x-ray image of the patient's chest, exposing the patient to a second dose of radiation using the x-ray imaging source that is calculated using the model of the patient's chest, wherein the second dose has a second magnitude that is different from the first magnitude.

26. The system of claim 16, wherein:

the x-ray image is a first x-ray image that has a first duration, and the set of operations further comprises:

at a later time after obtaining the first x-ray image of the patient's chest, exposing the patient to a second dose of radiation using the x-ray imaging source that is calculated using the model of the patient's chest, wherein the second dose has a second duration that is different from the first duration.

27. The system of claim 16, wherein the x-ray image is obtained at a mid-inhalation or mid-exhalation breathing phase of the patient.

28. A non-transitory computer-readable storage medium storing instructions, which, when executed by a system that includes one or more processors, cause the one or more processors to perform a set of operations, including:

positioning a patient at a first orientation relative to an x-ray imaging source;

using a 3D imaging technique, distinct from x-ray imaging, to measure one or more positions of the patient's chest;

while using the 3D imaging technique to measure the one or more positions of the patient's chest:

generating a model of the patient's chest using the one or more positions of the patient's chest;

updating the model of the patient's chest as the patient breathes; and obtaining an x-ray image of the patient's chest, including exposing the patient to a dose of radiation using the x-ray imaging source that is calculated using the model of the patient's chest.

* * * * *